(12) United States Patent
Sheets et al.

(10) Patent No.: US 7,566,818 B2
(45) Date of Patent: Jul. 28, 2009

(54) SECOND TC COMPLEX FROM XENORHABDUS

(75) Inventors: Joel Jay Sheets, Zionsville, IN (US); Weiting W. Ni, Carmel, IN (US); Scott Alan Bevan, Indianapolis, IN (US); Ignacio Mario Larrinua, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 11/314,892

(22) Filed: Dec. 21, 2005

(65) Prior Publication Data

US 2008/0104731 A1    May 1, 2008

(51) Int. Cl.
*A01H 5/00* (2006.01)
*A01H 5/10* (2006.01)
*C12N 1/21* (2006.01)
*C12N 15/82* (2006.01)
*C12N 15/31* (2006.01)

(52) U.S. Cl. ............... 800/301; 800/298; 800/295; 435/69.1; 435/252.3; 435/418; 536/23.7

(58) Field of Classification Search ............ None
See application file for complete search history.

(56) References Cited

U.S. PATENT DOCUMENTS

| 5,972,687 | A | * | 10/1999 | Smigielski et al. | ........ 435/252.3 |
| 6,630,619 | B1 | | 10/2003 | East | ........... 800/302 |
| 6,887,980 | B2 | | 5/2005 | Chen et al. | ............ 530/350 |
| 7,071,386 | B2 | * | 7/2006 | Bintrim et al. | ............ 800/301 |
| 2004/0194164 | A1 | | 9/2004 | Bintrim et al. | ............ 800/279 |
| 2005/0155104 | A1 | | 7/2005 | Apel-Birkhold et al. | .... 800/279 |

OTHER PUBLICATIONS

Lazar et al (Molecular and Cellular Biology, Mar. 1988, vol. 8, No. 3, pp. 1247-1252.*
Broun et al. Science, Nov. 13, 1998, vol. 282, pp. 1315-1317.*
Morgan et al. Applied and Environmental Microbiology (2001), vol. 67:2062-2069.*

* cited by examiner

*Primary Examiner*—Medina A Ibrahim
(74) *Attorney, Agent, or Firm*—Donald R. Stuart

(57) ABSTRACT

The subject invention relates to novel *Xenorhabdus* toxin complex (TC) proteins and genes that encode these proteins. More specifically, the subject invention relates to TC genes and proteins obtainable from *Xenorhabdus* strain Xwi.

9 Claims, 2 Drawing Sheets

Xeno Toxin Complex 1

Xeno Toxin Complex 2

FIG. 2

SECOND TC COMPLEX FROM XENORHABDUS

Figure 1:
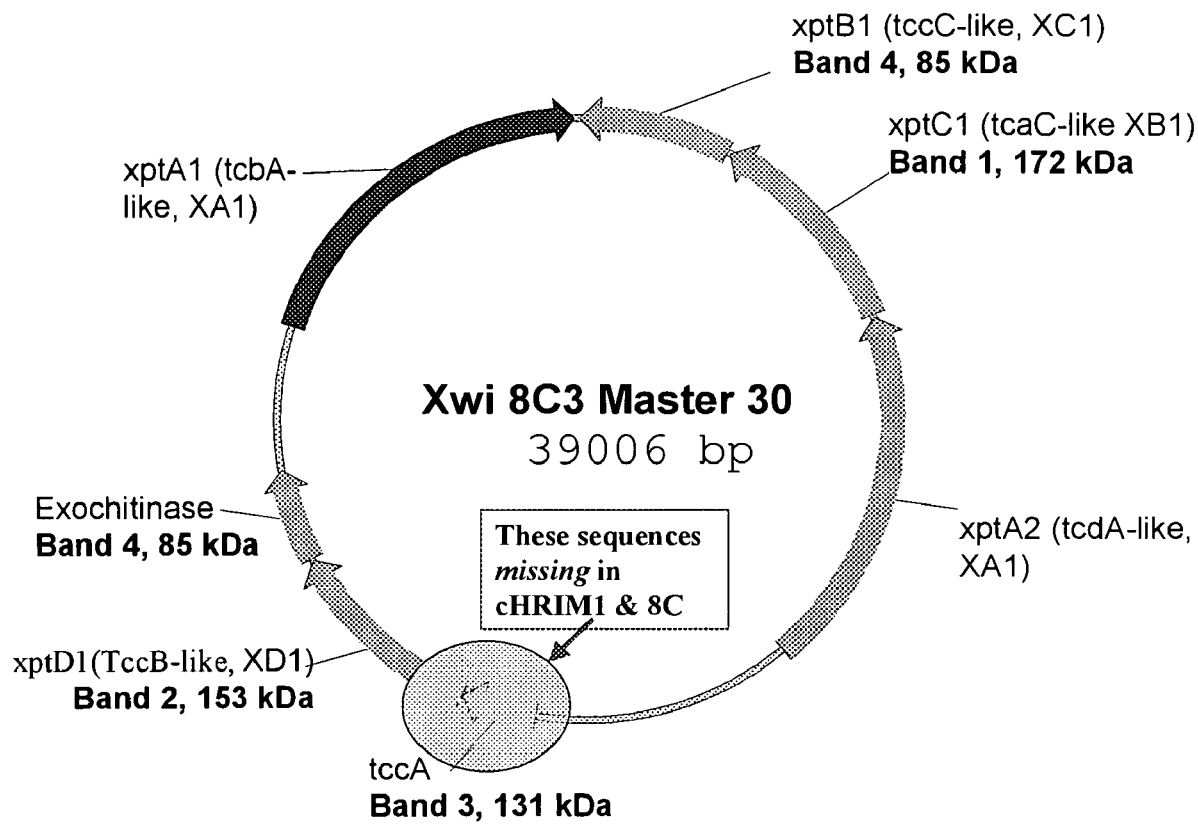

The present invention relates to a novel toxin complex (TC) protein obtainable from *Xenorhabdus* and to novel insecticidal combinations comprising this protein and other TC proteins.

BACKGROUND OF THE INVENTION

There is a great need for developing genes that can be expressed in plants in order to provide transgenic insecticidal plants that effectively control various insects. Recently, considerable attention has been given to toxin complex (TC) genes, obtainable from a variety of organisms, including *Photorhabdus*, *Xenorhabdus*, *Paenibacillus*, *Serratia*, and *Pseudomonas*.

There has been substantial progress in the cloning of genes encoding insecticidal toxins from both *Photorhabdus luminescens* and *Xenorhabdus nematophilus*. Toxin-complex encoding genes from *P. luminescens* were examined first. See WO 98/08932. Parallel genes were more recently cloned from *X. nematophilus*. Morgan et al., *Applied and Environmental Microbiology* 2001, 67:20062-69; WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25-280 kDa. See WO 97/17432, WO 98/08932, and R. H. ffrench-Constant and Bowen, 57 *Cell. Mol. Life Sci.* 828-833 (2000).

Genomic libraries of *P. luminescens* were screened with DNA probes and with monoclonal and/or polyclonal antibodies raised against the toxins. Four tc loci were cloned: tca, tcb, tcc and tcd. The tca locus is a putative operon of three open reading frames (ORFs), tcaA, tcaB, and tcaC, transcribed from the same DNA strand, with a smaller terminal ORF (tcaZ) transcribed in the opposite direction. The tcc locus also is comprised of three ORFs putatively transcribed in the same direction (tccA, tccB, and tccC). The tcb locus is a single large ORF (tcbA), and the tcd locus is composed of two ORFs (tcdA and tcdB); tcbA and tcdA, each about 7.5 kb, encode large insect toxins. TcdB has some level of homology to TcaC. It was determined that many of these gene products were cleaved by proteases. For example, both TcbA and TcdA are cleaved into three fragments termed i, ii and iii (e.g. TcbAi, TcbAii and TcbAiii). Products of the tca and tcc ORFs are also cleaved. See WO 98/08932 and R. H. french-Constant and D. J. Bowen, *Current Opinions in Microbiology,* 1999, 12:284-288.

Bioassays of the Tca toxin complexes revealed them to be highly toxic to first instar tomato hornworms (*Manduca sexta*) when given orally ($LD_{50}$ of 875 ng per square centimeter of artificial diet). R. H. french-Constant and Bowen 1999. Feeding was inhibited at Tca doses as low as 40 ng/cm$^2$. Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Microbiology,* 1999, 12:284-288.

WO 99/42589 and U.S. Pat. No. 6,281,413 disclose TC ORFs from *Photorhabdus luminescens*. WO 00/30453 and WO 00/42855 disclose TC proteins from *Xenorhabdus*.

While the exact molecular interactions of the TCs with each other, and their mechanism(s) of action, are not currently understood, it is known, for example, that the Tca toxin complex (comprised of TcaA, TcaB, and TcaC) of *Photorhabdus* is toxic to *Manduca sexta*. In addition, some TC proteins are known to have "stand alone" insecticidal activity, while other TC proteins are known to potentiate or enhance the activity of the stand-alone toxins. It is known that the TcdA protein is active, alone, against *Manduca sexta*, but that TcdB and TccC, together, can be used (in conjunction with TcdA) to greatly enhance the activity of TcdA. TcbA is the other main, stand-alone toxin from *Photorhabdus*. The activity of this toxin (TcbA) can also be greatly enhanced by TcdB- together with TccC-like proteins.

| Photorhabdus TC protein | Photorhabdus strain W14 nomenclature | Some homology to: |
|---|---|---|
| TcaA | Toxin C | TccA |
| TcaB | | TccB |
| TcaC | | TcdB |
| TebA | Toxin B | |
| TccA | Toxin D | TcdA N terminus |
| TccB | | TcdA C terminus |
| TccC | | |
| TcdA | Toxin A | TccA + TccB |
| | | or |
| | | TcaA + TcaB |
| TcdB | | TcaC |

TcaA, TcaB, TccA, and TccB are referred to as "small toxins", as distinguished from the "large toxins" TcbA and TcdA. The pair TcaA+TcaB in Toxin C is analogous to the large toxin TcdA in Toxin A; and in the pair TccA+TccB in Toxin D is likewise analogous to the large toxin TcdA. N. R. Waterfield, et al., "The tc genes of *Photorhabdus*: a growing family," TRENDS IN MICROBIOLOGY, Vol. 9, pp 185-191 (2001).

Some *Photorhabdus* TC proteins have some level of sequence homology with other *Photorhabdus* TC proteins. As indicated above, TccA has some level of homology with the N terminus of TcdA, and TccB has some level of homology with the C terminus of TcdA. Furthermore, TcdA is about 280 kDa, and TccA together with TccB are of about the same size, if combined, as that of TcdA. Though TccA and TccB are much less active on SCR than TcdA, TccA and TccB from *Photorhabdus* strain W14 are called "Toxin D." "Toxin A" (TcdA), "Toxin B" (Tcb or TcbA), and "Toxin C" (TcaA and TcaB) are also indicated above.

Furthermore, TcaA has some level of homology with TccA and likewise with the N terminus of TcdA. Still further, TcaB has some level of homology with TccB and likewise with the N terminus of TcdA. TcdB has a significant level of similarity to TcaC.

Relatively recent cloning efforts in *Xenorhabdus nematophilus* also appear to have identified novel insecticidal toxin genes with homology to the *P. luminescens* tc loci. See, e.g., WO 98/08388 and Morgan et al, *Applied and Environmental Microbiology* 2001, 67:20062-69. In R. H. ffrench-Constant and D. J. Bowen *Current Opinions in Microbiology,* 1999, 12:284-288, cosmid clones were screened directly for oral toxicity to another lepidopteran, *Pieris brassicae*. One orally toxic cosmid clone was sequenced. Analysis of the sequence in that cosmid suggested that there are five different ORF's with similarity to *Photorhabdus* tc genes; orf2 and orf5 both have some level of sequence relatedness to both tcbA and tcdA, whereas orf1 is similar to tccB, orf3 is similar to tccC and orf4 is similar to tcaC. Importantly, a number of these predicted ORFs also share the putative cleavage site documented in *P. luminescens*, suggesting that active toxins may also be proteolytically processed.

Five typical TC proteins from *Xenorhabdus* have heretofore been identified: XptA1, XptA2, XptB1, XptC1, and XptD1. XptA1 and XptA2 were known to have stand-alone toxin activity. The XptA2 protein was known to have some degree of similarity to the TcdA protein. XptB1 and XptC1 are *Xenorhabdus* potentiators that were known to enhance the activity of either (or both) of the XptA toxins. XptD1 was known to have some level of homology with TccB, and XptC1 was known to have some level of similarity to TcaC. XptB1 has some level of similarity to TccC.

United States Patent Application 20040194164 of Scott B. Bintrim et al. on "*Xenorhabdus* TC proteins and genes for pest control" discloses a set of novel *Xenorhabdus* TC proteins and genes obtainable from the Xwi strain of *Xenorhabdus nematophilus*. It also provides an exochitinase obtainable from from the Xwi strain of *Xenorhabdus nematophilus*.

TC proteins and genes have more recently been described from other insect-associated bacteria such as *Serratia entomophila*, an insect pathogen. Waterfield et al., TRENDS in Microbiology, Vol. 9, No. 4, April 2001.

TC proteins and lepidopteran-toxic Cry proteins have very recently been discovered in *Paenibacillus*. See U.S. Ser. No. 60/392,633 (Bintrim et al.), filed Jun. 28, 2002. Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus*," Antonie Van Leeuwenhoek 64:253-260). Some species in this genus are known to be pathogenic to honeybees (*Paenibacillus larvae*) and to scarab beetle grubs (*P. popilliae* and *P. lentimorbus*.) *P. larvae*, *P. popilliae*, and *P. lentimorbus* are considered obligate insect pathogens involved with milky disease of scarab beetles (D. P. Stahly et al. (1992), "The genus *Bacillus*: insect pathogens," p. 1697-1745, In A. Balows et al., ed., The Procaryotes, $2^{nd}$ Ed., Vol. 2, Springer-Verlag, New York, N.Y.).

Although some *Xenorhabdus* TC proteins have been found to "correspond" (have a similar function and some level of sequence homology) to some of the *Photorhabdus* TC proteins, the "corresponding" proteins share only about 40% (approximately) sequence identity with each other. This is also true for the more recently discovered TC proteins from *Paenibacillus* (those proteins and that discovery are the subject of co-pending U.S. Ser. No. 60/392,633).

Some TC proteins have stand alone insecticidal activity, but it is known that this activity can be enhanced when such proteins are used in combination with other TC proteins. In this regard, three relevant classes of TC proteins have heretofore been identified: Class A proteins, Class B proteins, and Class C proteins. A protein belonging to one of these classes is referred to hereinafter as a "Protein A", a "Protein B", or a "Protein C". Proteins are assigned to Class A, Class B, or Class C based on sequence similarity, as discussed in greater detail hereinafter. Class A proteins have stand alone insecticidal activity. Typical examples of Class A proteins are the "large toxins" TcdA, TcdA2, TcdA4, and TcBA from *Photorhabdus luminescens*, $XptA1_{Xwi}$ and $XptA2_{Xwi}$ from *Xenorhabdus nematophilus*, and SepA from *Serratia entomophila*. Class A proteins should also be understood to include the small toxin pairs that correspond to the large toxins, e.g. TcaA+TcaB in Toxin C and TccA+TccB in Toxin D. Class B and Class C proteins lack significant stand alone insecticidal activity, and have been referred to as potentiators. Typical Class B proteins are TcdB1, TcdB2, TcaC from *Photorhabdus luminescens*, $XptC1_{Xwi}$ *Xenorhabdus nematophilus*, $PptB1_{1529}$ from *Paenibacilluss* spp., and SepB from *Serratia entomophila*. Typical Class C proteins are TccC2 from *Photorhabdus luminescens*, $XptB1_{Xwi}$ from *Xenorhabdus nematophilus*, and $XptC1_{Xb}$ from *Xenorhabdus bovienii*. It has repeatedly been found that use of a Protein A in combination with a Protein B and a Protein C substantially enhances insecticidal activity over that obtained with the Protein A alone.

United States Patent Application Publication 2004/0208907 demonstrates that the activity of a Protein A can be potentiated by a Protein B and Protein C even if the Protein B and/or Protein C originates from an entirely distinct species from the one that produces the Protein A.

In light of concerns about insects developing resistance to a given pesticidal toxin, and in light of other concerns—some of which are discussed above, there is a continuing need for the discovery of new insecticidal toxins and other proteins that can be used to control insects.

BRIEF SUMMARY OF THE INVENTION

The present invention provides the novel toxin complex (TC) protein complex XTC-2 comprising XptB1 (SEQ ID NO:11), XptC1 (SEQ ID NO:10), XptD1 (SEQ ID NO:2), XptE1 (SEQ ID NO:4), and an exochitinase of SEQ ID NO:6.

The invention also provides a novel toxin complex (TC) protein, $XptE1_{Xwi}$ and DNA sequences encoding it. $XptE1_{Xwi}$ complements the previously known $XptD1_{Xwi}$ in a similar fashion to the pair TcaA+TcaB. That is, the $XptD1_{Xwi}$+ $XptE1_{Xwi}$ pair provides the equivalent of a "large toxin" lass A protein.

The invention also provides insecticidal compositions comprising $XptE1_{Xwi}$, and methods of controlling insects using it.

More specifically, the invention provides an isolated protein that has toxin activity against an insect, wherein said protein has at least 50% sequence identity with the amino acid sequence of SEQ ID NO:4($XptE1_{Xwi}$).

The invention also provides insecticidal compositions comprising, in combination, a protein having the amino acid sequence of SEQ ID NO:2 ($XptD1_{Xwi}$), a protein having the amino acid sequence of SEQ ID NO:4 ($XptE1_{Xwi}$), a Protein B, and a Protein C, wherein said Protein B is a 130-180 kda toxin complex potentiator having an amino acid sequence at least 40% identical to a sequence selected from the group consisting of:

SEQ ID NO:7 (TcdB1), SEQ ID NO:8 (TcdB2), SEQ ID NO:9 (TcaC), SEQ ID NO:10 ($XptC1_{Xwi}$), SEQ ID NO:11 ($XptB1_{Xb}$), SEQ ID NO:12 (PptB1(orf5)), and SEQ ID NO:13 (SepB); and said Protein C is a 90-120 kDa toxin complex potentiator having an amino acid sequence at least 35% identical to a sequence selected from the group consisting of:

SEQ ID NO:14 (TccC1), SEQ ID NO:15 (TccC2), SEQ ID NO:16 (TccC3), SEQ ID NO:17 (TccC4), SEQ ID NO:18 (TccC5), SEQ ID NO:19 ($XptB1_{Xwi}$), SEQ ID NO:20 ($XptC1_{Xb}$), SEQ ID NO:21 (PptC1 (orf 6 long)), SEQ ID NO:22 (PptC1 (orf 6 short)), SEQ ID NO:23 (SepC).

FIG. 1 is a map of Cosmid 8C3 (Cosmid 8C3 was provided by HRI). The complete sequences of xptA1, xptA2, xptB1, xptC1 and the exochitinase genes were obtained from this cosmid. Note that the xptE1 gene is missing completely from this cosmid, but was obtained from XTC-2.

Figure 2:
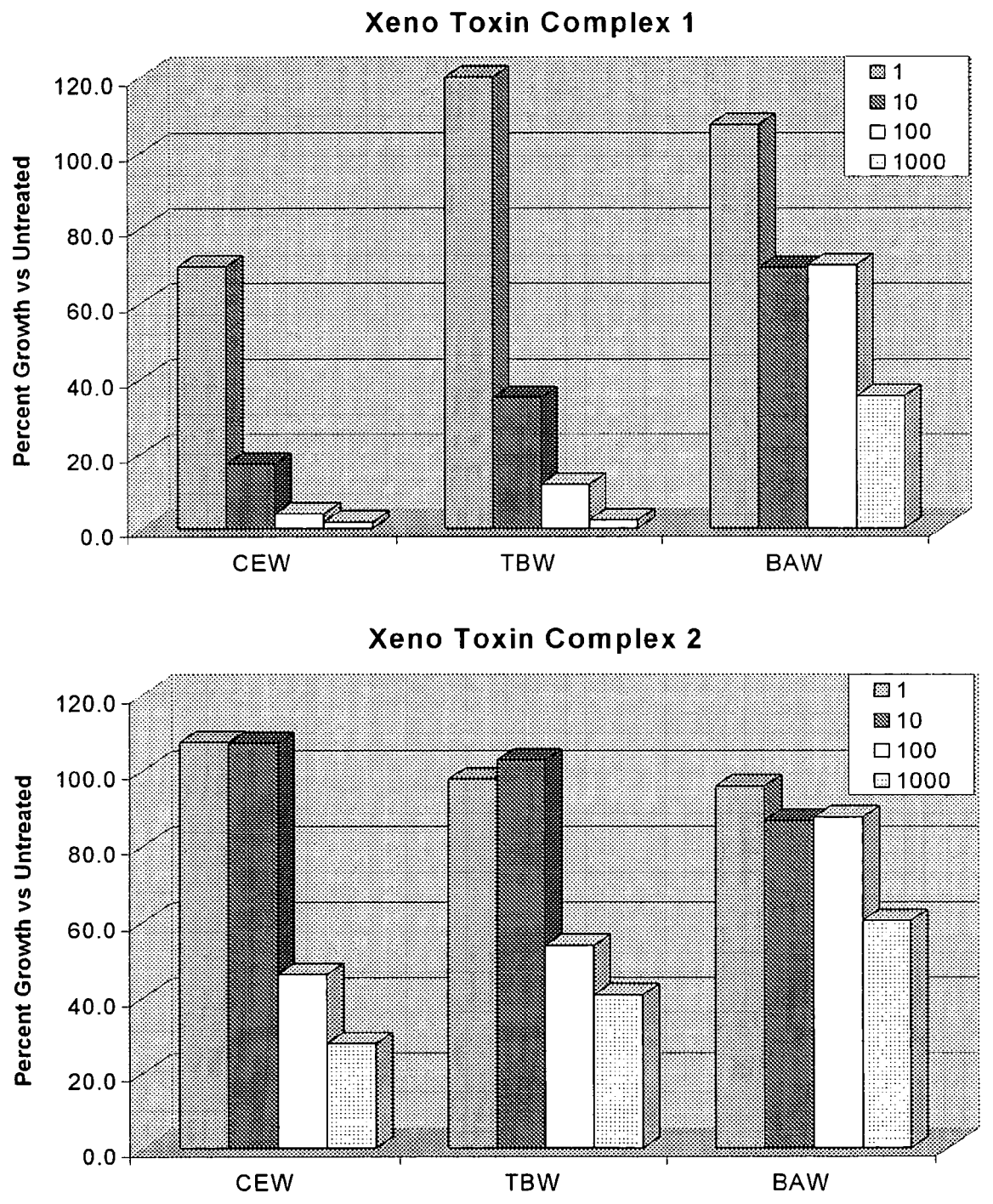

FIG. 2 shows bar graphs with bioassay data for XTC-2.

BRIEF DESCRIPTION OF THE SEQUENCES

SEQ ID NO:1 is the DNA sequence for xptD1$_{Xwi}$.
SEQ ID NO:2 is the amino acid sequence for XptD1$_{Xwi}$.
SEQ ID NO:3 is the DNA sequence for xptE1$_{Xwi}$.
SEQ ID NO:4 is the amino acid sequence for XptE1$_{Xwi}$.
SEQ ID NO:5 is the DNA sequence for the exochitinase from Xwi.
SEQ ID NO:6 is the amino acid sequence for the exochitinase from Xwi.
SEQ ID NO:7 is the amino acid sequence for TcdB1.
SEQ ID NO:8 is the amino acid sequence for TcdB2.
SEQ ID NO:9 is the gene and amino acid sequence for TcaC from GENBANK Accesion No. AF346497.1.
SEQ ID NO:10 is the amino acid sequence for XptC1$_{Xwi}$ (1,493 amino acids).
SEQ ID NO:11 is the amino acid sequence for XptB1$_{Xb}$ (1506 amino acids).
SEQ ID NO:12 is the amino acid sequence for PptB1$_{1529}$ (*Paenibacillus* ORF5) (1445 amino acids).
SEQ ID NO:13 is the amino acid sequence for the SepC protein (1428 amino acids).
SEQ ID NO:14 is the gene and protein sequence for TccC1 from GENBANK Accession No. AAC38630.1.
SEQ ID NO:15 is the amino acid sequence for TccC2 from GENBANK Accession No. AAL18492.
SEQ ID NO:16 is the amino acid sequence for TccC3.
SEQ ID NO:17 is the amino acid sequence for TccC4$_{W-14}$.
SEQ ID NO:18 is the gene and amino acid sequence for TccC5 from GENBANK Accession No. AF346500.2.
SEQ ID NO:196 is the amino acid sequence for XptB1$_{Xwi}$.
SEQ ID NO:20 is the amino acid sequence for XptC1$_{Xb}$ (962 amino acids).
SEQ ID NO:21 is an alternate (long) amino acid sequence for PptC1$_{1529L}$.
SEQ ID NO:22 is an alternate (short) amino acid sequence for PptC1$_{1529S}$.
SEQ ID NO:23 is the amino acid sequence for the Sep C protein.

DEFINITIONS

Isolated polynucleotides and isolated proteins. As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Xenorhabdus* protein, exemplified herein, produced by a plant is an "isolated protein."

Toxin activity against an insect. By toxin activity against an insect it is meant that a protein function as an orally active insect control agent (alone or in combination with other proteins), as demonstrated by its ability to disrupt or deter insect activity, growth, and/or feeding. Toxin activity may or may not cause death of the insect. When an insect comes into contact with an effective amount of a "toxin" of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Complete lethality to feeding insects is preferred but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

Sequence identity. Unless otherwise specified, as used herein percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. To obtain gapped alignments for comparison purposes, Gapped BLAST is used as described in Altschul et al (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above.

Hybridizes under stringent conditions. As used herein "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes was performed by standard methods (see, e.g., Maniatis, T., E. F. Fritsch, J. Sambrook [1982] *Molecular Cloning. A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25E C below the melting temperature (Tm) of the DNA hybrid in 6× SSPE, 5× Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266-285):

$$Tm=81.5E\ C+16.6\ \text{Log}[Na+]+0.41\ (\%\ G+C)-0.61(\%\ \text{formamide})-600/\text{length of duplex in base pairs}.$$

Washes are typically carried out as follows:

(1) Twice at room temperature for 15 minutes in 1× SSPE, 0.1% SDS (low stringency wash).

(2) Once at Tm-20EC for 15 minutes in 0.2× SSPE, 0.1% SDS (moderate stringency wash).

For oligonucleotide probes, hybridization was carried out overnight at 10-20EC below the melting temperature (Tm) of the hybrid in 6× SSPE, 5× Denhardt's solution, 0.1% SDS, 0.1 mg/ml denatured DNA. Tm for oligonucleotide probes was determined by the following formula:

$$Tm\ (E\ C)=2(\text{number }T/A\text{ base pairs})+4(\text{number }G/C\text{ base pairs})$$

(Suggs, S. V., T. Miyake, E. H. Kawashime, M. J. Johnson, K. Itakura, and R. B. Wallace [1981] *ICN-UCLA Symp. Dev.*

*Biol. Using Purified Genes*, D. D. Brown [ed.], Academic Press, New York, 23:683-693).

Washes were typically carried out as follows:

(1) Twice at room temperature for 15 minutes 1× SSPE, 0.1% SDS (low stringency wash).

(2) Once at the hybridization temperature for 15 minutes in 1× SSPE, 0.1% SDS (moderate stringency wash).

In general, salt and/or temperature can be altered to change stringency. With a labeled DNA fragment>70 or so bases in length, the following conditions can be used:

| | |
|---|---|
| Low: | 1 or 2x SSPE, room temperature |
| Low: | 1 or 2x SSPE, 42E C. |
| Moderate: | 0.2x or 1x SSPE, 65E C. |
| High: | 0.1x SSPE, 65E C. |

Protein B. Protein B refers to a 130-180 kDa toxin complex potentiator having an amino acid sequence at least 40% identical to a sequence selected from the group consisting of: SEQ ID NO:7 (TcdB1), SEQ ID NO:8 (TcdB2), SEQ ID NO:9 (TcaC), SEQ ID NO:10 ($XptC1_{Xwi}$), SEQ ID NO:11 ($XptB1_{Xb}$), SEQ ID NO:12 (PptBp1(orf5)), and SEQ ID NO:13(SepB).

Protein C. Protein C refers to a 90-120 kDa toxin complex potentiator having an amino acid sequence at least 35% identical to a sequence selected from the group consisting of: SEQ ID NO:14 (TccC1), SEQ ID NO:15 (TccC2), SEQ ID NO:16 (TccC3), SEQ ID NO:17 (TccC4), SEQ ID NO:18 (TccC5), SEQ ID NO:19 ($XptB1_{Xwi}$), SEQ ID NO:20 ($XptC1_{Xb}$), SEQ ID NO: 21 (PptC1(orf 6 long)), SEQ ID NO:22 (PptC1(orf 6 short)), SEQ ID NO:23 (SepC).

Potentiator. Potentiator protein refers to a TC "Protein B" or "Protein C."

Associating a toxic protein with a material to be protected can be achieved by, e.g. applying the toxic protein to the material, admixing it with the material, and, in the case of transgenic plant material, by causing the plant cells to express the toxic protein.

Effective amount of a toxic protein means an amount that provides toxic activity against an insect.

DETAILED DESCRIPTION OF THE INVENTION

EXAMPLE 1

We describe here the purification and characterization of a novel lepidopertan-active protein toxin complex termed *Xenorhabdus* Toxin Complex 2 (XTC-2) isolated from *Xenorhabdus nematophilus* (Xwi strain). We determined XTC-2 to be comprised of five different proteins, $XptC1_{Xwi}$ (a 170 kDa "B" type protein), $XptD1_{Xwi}$ (a 140 kDa protein), $XptE1_{Xwi}$ (a 130 kDa protein), $XptB1_{Xwi}$ (112 kDa "C" type protein) and an exochitinase. The molecular weight of XTC-2 was estimated to be between 1,150-1,300 kDa based upon migration on native polyacrylamide gel electrophoresis (PAGE) and elution volume from size exclusion chromatography. Based upon its estimated molecular weight and the size of the individual protein subunits, we determined that multiple copies of the subunits are most likely present in the complete native protein. When fed to insects in a top load diet bioassay, XTC-2 results in inhibition of larval growth, with fifty percent inhibition of growth ($GI_{50}$) occurring with approximately 1 ng/cm$^2$ of applied material when tested against corn earworm larvae (CEW, *Helicoverpa zea*,) and 10-70 ng/cm$^2$ vs tobacco budworm larvae (TBW, *Heliothis virescens*). The toxin complex has weak activity against beet army worm (BAW, *Spodoptera exigua*), and did not inhibit growth of southern corn rootworm larvae (SCR, *Diahrotica undecimpunctata howardi*) at protein concentrations as high as 1,000 ng/cm$^2$. This limited spectrum of insect bioassays demonstrates that XTC-2 has activity against lepidopteran insects, but further bioassays would be needed to fully characterize its spectrum of insect activity.

Methods

Materials. Aqueous solutions were prepared using Milli-Q purified water. All solvents used were HPLC grade. All other chemicals were analytical grade from commercial supply houses. Bovine serum albumin (BSA) Fraction V (cat. #A7906), and the general protease inhibitors for bacterial cell lysates (cat. #P8465) were both from Sigma Chemical, (St. Louis, Mo.). Native molecular weight protein markers were from Amersham (Piscataway, N.J., cat. #17-0445-01). Protein liquid chromatography was performed on an AKTA purifier 900 chromatography system.

Protein Purification. Cell pellets obtained from a 2 liter culture after overnight incubation of the *Xenhorabdus nematophihis* bacteria were provided by Scott Bintrim, and typically stored frozen at −20° C. for less than two weeks. Frozen cells were suspended in 250 ml of 50 mM Tris-HCl pH 8.0, 0.10 M NaCl, 1 mM DTT, 10% glycerol and lysozyme (0.6 mg/ml). A small amount of glass beads (0.5 mm), was added and the solution gently shaken to facilitate suspension. The cells were then disrupted in approx. 50 ml batches by sonicating them at maximum output power two times for 30 seconds, keeping the lysate cold using an ice bath. The broken cells were then centrifuged at 48,000×g for 60 min. at 4° C. The supernatant was collected, a bacterial protease inhibitor cocktail added (2.0 ml), and the solution dialyzed against 25 mM Tris-HCl, pH 8.0 overnight. The protein was then loaded onto a Q sepharose XL (1.6×10 cm) anion exchange column. Bound proteins were eluted using a linear 0 to 1M NaCl gradient in 10 column volumes at a flow rate of 5 ml/min and collecting in 5 ml fractions. The high molecular weight toxin complexes eluted in the early fractions. These fractions were combined and concentrated to 2 ml using a 100 kDa filter concentrator. The concentrated proteins were then loaded onto a superose 200 size exclusion column (1.6×60 cm), using 50 mM Tris-HCl, 100 mM NaCl, 5% glycerol, 0.05% Tween-20, pH 8.0 at a flow rate of 1.0 m/min. The large molecular weight proteins eluting from the column, were combined, brought to 1.5 M ammonium sulfate concentration and loaded onto a phenyl superose (0.5×5 cm) hydrophobic-interaction column. Proteins were eluted using a decreasing linear gradient of 1.5 to 0 M ammonium sulfate in 25 mM Tris-HCl, pH 8.0 over 20 column volumes at a flow rate of 1 ml/min. The toxin complexes eluted together as a broad peak at low salt concentration. The protein was dialyzed overnight against 25 mM Tris-HCl, and loaded onto a high resolution MonoQ (0.5×5 cm) anion exchange column. The two separate toxin complexes were resolved with baseline resolution using a linear gradient of 0 to IM NaCl in 25 mM Tris-HCl obtained in 20 column volumes. The proteins were identified by N-terminal amino acid sequencing and Matrix-Assisted Laser Desorption/Ionization Time-of-Flight (MALDI-TOF) mass spectrometry analysis as described below.

Gel electrophoresis. Purification was monitored by sodium dodecyl sulfate polyacrylamide gel electrophoresis (SDS-PAGE) under reducing and denaturing conditions by method of Laemmli (Laemmli, 1970). Various quantities of protein were loaded into wells of a 4-20% tris-glycine polyacrylamide gel (Zaxis, Hudson, Ohio) and separated by applying 170 volts of electricity for 90 minutes. Detection of the separated protein bands was achieved by staining the gel with Coomassie brilliant blue R-250 (BioRad, Hercules, Calif.) for one hour, then destaining first with a solution of 45% methanol and 10% acetic acid, then with a solution of 5% methanol and 7% acetic acid. The gels were imaged and analyzed using a BioRad Fluro-S Multi Imager™. Relative molecular weight of the protein bands was determined by including a sample of BenchMark™ Protein Ladder (Life Technologies, Rockville, Md.) in one well of the gel.

Proteolytic digestion. SDS gel slices containing Coomassie blue stained bands were removed from the gel and placed into a siliconized Eppendorf microcentrifuge tubes. The gel slices were destained with 50% acetonitrile in 25 mM $NH_4HCO_3$ until the slices became clear and the solvent removed using a Speed-Vac (Savant Instruments, Holbrook, N.Y.). The dried gel slices were crushed and enough sequencing grade trypsin at 12.5 µg/ml (Roche Diagnostics, Indianapolis, Ind.) was added to cover the gel pieces. After 30 min incubation at room temperature the excess trypsin was removed and replaced with 25 mM $NH_4HCO_3$. The digestion was allowed to proceed for 4 hr at 37° C. The digested peptides were then extracted by shaking for one hour with a solution of 50% acetonitrile in 0.5% trifluoro acetic acid (TFA, Sigma). After brief centrifugation to pellet the gel pieces, the supernatant containing the peptides was transferred to a fresh tube and dried in a Speed-Vac. The peptides were then suspended in 6 µL of 0.1% TFA, absorbed to a $C_{18}$ ZipTip resin (Millipore, Bedford, Mass.) and eluted with 75% acetonitrile/0.1% TFA. The eluent was stored at −20° C. freezer until MALDI-TOF mass spectral analysis.

Fragment derivatization. To facilitate MALDI-Post Source Decay (PSD) sequencing the peptides were modified using Ettan™ CAF™ Sequencing Kit (Amersham). This modification improves fragmentation efficiency at peptide bonds and results in the formation of only positively charged y ions which become separated in the MALDI reflection. Briefly the peptides were absorbed onto a C18 Ziptip resin. The lysine residues at C-terminus were protected by converting to homoarginine using O-methylisourea-hydrogen sulfate and incubating overnight. After washing the ziptip with water to remove the quanidination reagent, the N-terminal of the peptides were sulfonated with provided CAF reagent solution for at least three min. The ziptip was washed and the derivatized peptides were eluted with 80% acetonitrile for MALDI-PSD sequencing.

Mass Spectrometry Analysis. The extracted peptides were analyzed using MALDI-TOF mass spectrometry. The instrument used was a Voyager DE-STR MALDI-TOF mass spectrometer (PerSeptive Biosystems, Framingham, Mass.). The instrument utilizes a 337 nm nitrogen laser for the desorption/ionization event and a 3.0 meter reflectron time-of-flight tube.

To generate peptide mass fingerprints the samples derived above were spotted onto a MALDI stainless steel plate in a 1:1 ratio of 0.5 µL of sample with 0.5 µL of matrix mixed on the plate using the dried droplet spotting technique (air dried). The matrix was a saturated solution of α-cyano-4-hydroxycinnamic acid in 50% acetonitrile with 0.1% TFA. External calibration was performed by using a solution of Calibration Mix 2 (PE Biosystems, Foster City, Calif.). Internal calibration was performed using, if detected, the autolytic trypsin peak at m/z 842.50, 1045.56, or 2211.10. Acquired spectra were de-isotoped and peptide mass fingerprints (PMF) tables were exported for database searching.

Chemically modified peptides were used for MALDI-PSD sequencing. The instrument was first calibrated with an angiotensin peptide at 1296 Da. Calibration for PSD fragments was performed using the fragmented angiotensin peptide as described by the instrument manual. MALDI-MS was first performed on the samples in both positive and negative modes to generate mass fingerprints. From the fingerprints at least five peptides with high intensities were selected for MALDI-PSD analysis. PSD fragmentation and detection was performed by incrementally increasing laser intensity by 50 V and tilting the reflectron mirror ratio from 1.0 to 0.2. The fragment spectra from different mirror ratios were stitched together by instrument control software. The mass differences between neighboring peaks were calculated and their corresponding amino acid was determined from an amino acid mass table.

Edman N-terminal amino acid sequencing. After SDS PAGE separation, proteins were transferred to PVDF membrane (Bio-Rad) using standard procedure (100V for one hr). The membrane was stained briefly with Coomassie blue, the protein bands removed, dried and sent for N-terminal sequencing. N-terminal sequencing was performed with a Procise 494 (Applied Biosystem, Freemont, Mass.) using a standard protocol provided by the manufacture. Sequence was determined by accompanied software Sequence Pro Ver. 1.0 and then manually corrected for erroneous sequence assignments.

Database searching and protein identification. Proteomics search engine Mascot (London, UK) was used for database searching and protein identification. A proprietary toxin database was constructed by compiling all the known (public and private) *Photorhabdus* and *Xenorhabdus* toxin related protein and DNA translation sequences. PMF tables were pasted in the Mascot search form and the search performed against both the toxin database and NCBI non-redundant protein database. No molecular weight and pI restrictions were applied during the search, nor during the numerous modifications. The mass error tolerance was set at 0.1 Da and missed cleavage was set at 1.

Insect bioassays. Corn earworm (CEW, *Helicoverpa zea*) used in these studies were supplied as eggs by the insectary at North Carolina State University. Tobacco budworm (TBW, *Heliothis virescens*) and beet armyworm (BAW, *Spodoptera exigua*) eggs were obtained from the insectary of Dow AgroSciences. Southern corn rootworm eggs (SCR, *Diabrotica undecimpunctata howardi*) were supplied by FrenchAg Research, Lamberton, Minn., or Crop Characteristics, Inc., Farmington, Minn. The eggs were washed and held at 24° C. and 50% RH until they hatched. The artificial diet consists of 2-4% powdery solids such as soy flour, yeast, wheat germ, casein, sugar, vitamins, and cholesterol suspended in a 1.0-2.0% dissolved agar in water matrix. For bioassay, toxin protein complexes were diluted in ten-fold increments into 10 mM sodium phosphate buffer, pH 7.0 to concentrations ranging from 1 to 1000 ng toxin per cm² then applied to the surface of the artificial diet. Each concentration was assayed separately with 8 replications by placing newly emerged neonates onto the treated diet and holding the test at 28° C. for five days. The weights of the larvae were measured at the end of the time period in addition to recording mortality or stunting of the insects. Dead larvae were scored as zero weight. $GI_{50}$ was determined using the measured weights of the insects and the Trimmed Spearman Karber statistical method (Hamilton et al., 1977).

Results

Toxin Complex Purification and Characterization. Initial anion chromatography of the cell lysate from *Xenorhabdus nematophilus* resulted in poor resolution but captured the majority of the high molecular weight proteins, which eluted between 100-200 mM salt concentrations. Subsequent size exclusion chromatography isolated a well-resolved high molecular weight fraction eluting at 40 ml very near the void volume of the column. This fraction was further resolved into two broad and symmetrical peaks in an approximate 7:1 ratio by hydrophobic-interaction chromatography. The high molecular weight proteins are located in the larger peak eluting at approximately 0.4 M ammonium sulfate and were resolved into two separate peaks using a high resolution MonoQ anion exchange column. The two peaks elute between 35-45 mS/cm conductance. When analyzed by SDS-PAGE, the first peak was determined to consist of three proteins. Using a calibration curve generated from separation of the Benchmark Ladder, these three proteins have apparent molecular weights of 280, 172, and 85 kDa. The molecular weight of these proteins correspond to those found in Xeno Toxin Complex 1 (XTC-1) previously identified (Morgan et al., 2001; Sergeant et al., 2002) composed of proteins XptA2$_{Xwi}$, XptC1$_{Xwi}$ and XptB1$_{Xwi}$, respectively. Confirmation of the identity of these proteins was done by MALDI-TOF analysis of each of the protein bands.

The second peak from the MonoQ anion exchange column termed as Xeno Toxin Complex 2 (XTC-2), is composed of at least 4 proteins as determined by SDS-PAGE. Based upon migration on SDS PAGE under reducing conditions, the apparent molecular weights of the four protein bands correspond to 172, 153, 131, and 85 kDa. When analyzed by native PAGE using a 3-8% tris acetate gel, a single high molecular weight protein band is obtained, showing that the individual proteins resolved by SDS-PAGE form a single protein complex under native conditions. Using four molecular weight standards in the native gel, we generated a standard curve for migration of proteins under native conditions. Based upon the relative migration of XTC-2 by PAGE under native conditions and compared to known standards, it has an apparent molecular weight of about 1,300 kDa. Note that due to the very high molecular weight of XTC-2, this value was obtained by extrapolation from the calibration curve. The high molecular weight of XTC-2 indicates that the complex is most likely not only composed of at least the four different proteins resolved by SDS-PAGE, but that multiple copies of the different proteins are most likely included as part of the complex.

When loaded on to a calibrated Superose 200 1×30 cm size exclusion column, XTC-2 eluted as a single symmetrical peak, very close to the void volume of the column. Three separate injections of XTC-2 were made using the calibrated superose 200 1×30 cm column, resulting in elution of the toxin complex at 8.13, 8.19 and 8.02 ml (average=8.11 ml). Using a calibration curve for this size exclusion column, this elution volume corresponded to an apparent molecular weight of 1,150 kDa (range 1,100-1,200 kDa). This value is close to the value obtained by native PAGE analysis (1,300 kDa), and further demonstrates that XTC-2 is most likely composed of multiple copies of the different subunits that can be separated by SDS-PAGE under denaturing conditions.

Densitometric analysis of the SDS-PAGE gel indicates that the different protein bands comprising the XTC-2 are not present at equal concentrations or molar ratios (Table 1). XptC1$_{Xwi}$ is present in the lowest amount, based upon density of staining by coomassie blue dye. Given that this is the largest protein (172 kDa) of the five proteins comprising XTC-2, on a molar basis the content of this protein is very low relative to the molar amount of the other proteins subunits comprising the total toxin. Since the exochintinase and XptB1$_{Xwi}$ was poorly resolved on this gel, we did not determine the relative proportions of these two different proteins comprising the entire Toxin Complex.

Protein Identification. The proteins in the complexes were resolved by SDS-PAGE. From previous work it is known that XTC-1 is composed of four 280 kDa toxin subunits (named XptA2$_{Xwi}$) and one XptC1$_{Xwi}$ and one XptB1$_{Xwi}$ protein. The components of XTC-1 were confirmed as expected as XptA2$_{Xwi}$, XptC1$_{Xwi}$ and XptB1$_{Xwi}$,. Although the particular preparation of XTC-2 illustrated here contains a high molecular weight protein (~280 kDa) possibly corresponding to XptA2$_{Xwi}$, in subsequent steps this protein was removed and thus is not part of XTC-2. Two very faint proteins at about 32 kDa were evaluated by MALDI and appear to be breakdown products of the XptD1$_{Xwi}$ and XptB1$_{Xwi}$ proteins (data not shown). These data suggest that toxin complex 2 is composed of at least 4 peptides.

To identify these peptides the protein bands were either blotted onto PVDF membrane for N-terminal sequencing, or analyzed with MALDI-TOF. Initial attempt to identify the peptides in lane 3 using MALDI peptide mass fingerprints (PMF) failed to produce positive hits due to lack of protein sequences in our proprietary toxin database. We subsequently searched for all the *Photorhabdus* and *Xenorhabdus* sequences from our previous sequencing efforts and from publicly available database (NCBI non-redundant database and Swiss-Prot database). Obtained DNA sequences were translated into amino acid sequences. This new set of amino acid sequences was then updated to our toxin database. The database searching was repeated against the new toxin database and positive hits with high confidences were returned for all bands in XTC-2. The top band (MW ~172 kDa) was found to be highly similar to (>95%), if not identical to XptC1$_{Xwi}$, a protein also found in XTC-1. Forty matching tryptic fragments cover 35% of amino acids in the sequence, yielding a highly significant Mowse score of 290, (a score greater than 40 is significant at the 0.05 level). The second band (MW ~153) was highly similar to, if not identical to, XptD1$_{Xwi}$. Forty four matching fragments cover 44% of amino acids in the sequence, producing a Mowse score of 270. The significant hit (Mowse score 121) for the third band (~131 kDa) corresponds to Xwi XptE1$_{Xwi}$. However, calculated MW from the XptE1$_{Xwi}$ sequence at hand is only 57 kD, significantly smaller than 131 kD as indicated by SDS PAGE, indicating the sequence in the toxin database is incomplete. The fourth band (~85 kDa) was found to contain at least two peptides. This was confirmed upon close inspection of the gel that shows two very slightly resolved bands (not very obvious on the digital image). Database searching using mix of the PMFs revealed that one protein is highly similar to, if not identical to Xeno XptB1$_{Xwi}$ (Mowse score 111, coverage 24% and matching peptides 18), the other matches with a Xwi exochitinase (Mowse score 195, coverage 52%, and matching peptides 21). The detail database search results are attached as appendices.

To confirm the identities of these proteins, they were also subjected to N-terminal and internal sequencing. The N-terminal sequence of band 1, determined by Edman degradation, corresponded to N-terminus of XptC1$_{Xwi}$. The N-terminal sequence of band 2 was identical to N-terminus of XptD1$_{Xwi}$.

At least five fragments from each of bands corresponding to XptE1$_{Xwi}$, XptD1$_{Xwi}$ and XptB1$_{Xwi}$ were selected for MALDI-PSD analysis. All the internal fragment sequences matched with their corresponding protein sequences as predicted by MALDI PMF data, indicating positive identification of these 5 proteins.

It is clear that this toxin complex 2 is formed from 5 proteins, namely XptC1$_{Xwi}$ XptE1$_{Xwi}$, XptD1$_{Xwi}$, XptB1$_{Xwi}$ and a putative exochitinase. By inspecting Xwi cosmids that were previously characterized, we found that all or at least part of the genes encoding these 5 proteins were located on cosmid 8C3 where the toxin genes (XptA2$_{Xwi}$, and XptA1$_{Xwi}$) of XTC-1 are also located (FIG. 1) In this cosmid the XptE1$_{Xwi}$ gene was truncated, which explains the discrepancy of the 131 kd protein (XptE1$_{Xwi}$) matching the 57 kd gene that was obtained from this cosmid. It also explains our inability to identify XTC-2 from screening the cosmid library for bioactivity, since the only four complete genes of the five toxin genes were present.

It is not unusual to find toxin complex and auxiliary genes clustered together in the genome. In cosmid 8c3, there are two large operons composed of toxin-like genes. The first one contains a truncated xptE1$_{Xwi}$ gene, a xptD1$_{Xwi}$ gene (which together would form a toxin A like complex), an exochitanase gene and a gene for xptA1$_{Xwi}$. The structure of the DNA sequence of the upstream region of the exochitanase region is revealing. Its ribosome binding site is sequestered in a large stem loop structure that would prevent this gene from being transcribed except as part of the operon. Of course, in the genomic sequence xptE1$_{Xwi}$ would not be truncated. We do not know if xptE1$_{Xwi}$ is the first gene in that operon or whether there are more toxin like genes upstream from it. The second operon which is transcribed in the opposite orientation contains a toxin A gene (xptA2$_{Xwi}$), a xptC1$_{Xwi}$ gene and a xptB1$_{Xwi}$ gene. These two operons are in extremely close proximity, the two ends being within a few hundred bases of each other. While the second operon contains all the genes necessary for toxicity, the first operon does not. Toxin gene clustering, as seen in this and other cases, would ensure that genetic recombination would not separate the first toxin gene operon from the second since the second contains genes essential for the generation of an active complex from the first.

Bioactivity. Highly purified preparations of XTC-1 and XTC-2 were bioassayed against CEW, TBW, BAW and SCR larvae. Both complexes exhibited a similar spectrum of activity against these four insects. Neither complex was active against SCR larvae when tested at a diet concentration of up to 1 µg/cm². (data not shown). Both complexes, however, were very active against CEW and TBW, but principally against CEW larvae. The primary effect of these toxin complexes against these two insects was stunting, but at the highest concentrations tested (1 µg/cm²), some death of the larvae was observed. LC-50 values were >1 µg/cm² for both of these toxins against these insects. Bioassay data are presented in the bar graphs shown in FIG. 2. Against CEW, XTC-1 caused 50% inhibition of growth (GI$_{50}$) at between 0.001-0.01 µg/cm², whereas XTC-2 also caused significant stunting of the CEW larvae, but the GI$_{50}$ was in the range of 0.01-0.1 µg/cm². Thus, both toxin complexes are highly potent against CEW, but XTC-1 is about 10-fold more active than XTC-2. A similar profile of toxicity is seen with TBW larvae, with XTC-1 being more active than XTC-2. Fifty percent growth inhibition of TBW larvae was observed at less than 10 ng/cm² for XTC-1, whereas XTC-2 required about 100 ng/cm². Against BAW larvae, XTC-1 was only moderately active, causing 50 percent growth inhibition at concentrations between 0.1 to 1 µg/cm², whereas XTC-2 required more than 1 µg/cm² to inhibit growth by 50 percent. With that said, XTC-2 is still very active biologically and could be of high value for use in imparting insect resistance into plants as it is further understood and the activity of each individual protein component is better characterized.

Discussion

This experiment demonstrates the first discovery and characterization of a second complete toxin complex (XTC-2) found in the Xwi strain of *Xenorhabdus nematophihis*. Using an active cosmid 8C3 prepared by Dow AgroSciences scientists, and from data provided by researchers at HRI using a different cosmid (cHRIM1), scientists at both institutions were able to identify the original toxin complex (XTC-1) that consisted of three proteins, XptA2$_{Xwi}$, XptC1$_{Xwi}$ and XptB1$_{Xwi}$. The 8C3 cosmid contains additional genes with unknown function. Some of these genes encode for proteins that we have purified and identified in XTC-2. These include genes encoding XptC1$_{Xwi}$, XptB1$_{Xwi}$ and the exochitinase. However, parts of the genes encoding the XptD1$_{Xwi}$ and XptE1$_{Xwi}$ proteins were either truncated or absent in the cHRIM1 cosmid. Another protein belonging to XTC-2 (XptE1$_{Xwi}$) was missing from the cHRIM1 cosmid. The cHRIM1 cosmid also contained an exochitinase gene directly downstream of the xptD1Xwi gene that was considered not to contribute to bioactivity based on gene inactivation studies. The lack of the complete set of proteins comprising XTC-2 in the cHRIM1 cosmid probably resulted in the poor level of biological activity seen for this cosmid and thus most likely prevented these researchers from identifying these proteins as part of an active protein complex. We now have a more complete picture of the genes in cosmid 8C3 and a better understanding of their function.

The XTC-2 is a very large protein complex, estimated at between 1,150-1,300 kDa, depending on the method utilized to determine protein size. It is composed of at least five different protein subunits. Some of these subunits must be present in multiple copies in the complete toxin complex, since the sum of the molecular weights of the individual components (626 kDa) equals only about half of the molecular weight of XTC-2. The stochiometry of XTC-1 is 4:1:1, for the XptA2$_{Xwi}$, XptC1$_{Xwi}$ and XptB1$_{Xwi}$ proteins respectively 1. This toxin complex does not have an exochitinase associated with it. Given the homology between XptE1$_{Xwi}$ and XptD1$_{Xwi}$ proteins with XptA2$_{Xwi}$, it is reasonable to assume that these two proteins represent gene cleavage products, that when put together, organize into a protein of similar structure as XptA2$_{Xwi}$. Thus, XptE1$_{Xwi}$+XptD1$_{Xwi}$ together could be equivalent to one XptA2$_{Xwi}$ protein. Thus, if XTC-1 contains four XptA2$_{Xwi}$ subunits, then by inference we could assume that XTC-2 contains four XptE1$_{Xwi}$ and four XptD1$_{Xwi}$ subunits. This would add up to a combined molecular weight of 1,136 kDa, which is still lower than the estimated molecular weight of the entire XTC-2. The addition of a single XptC1$_{Xwi}$, XptB1$_{Xwi}$, and exochitinase protein would add 342 kDa to the weight of the complex, resulting in a overall size of 1,478 kDa, which is about 13% larger than the estimated size of the complete toxin complex. These estimates assume that there is no significant truncation or other processing of the protein subunits upon forming the toxin complex. What ever the true stochiometry of the toxin complex turns out to be, it is clearly composed of multiple copies of identical subunits.

The exochitinase was identified by MALDI from what first appeared to be a homogeneous protein band migrating at a molecular mass consistent with that of a truncated XptB1$_{Xwi}$ (85 kDa). While the truncated XptB1$_{Xwi}$ in XTC-2 was positively identified, careful MALDI analysis enabled the discovery that the signal actually was derived from two co-migrating proteins, XptB1$_{Xwi}$ and an exochitinase.

This is the first demonstration of bioactivity from a *Xenorhabdus* toxin complex containing co-purified XptD1$_{Xwi}$ and exochitinase proteins, and might indicate an important role for this exochitinase in toxin complex mode of action. The precise role of the exochitinase protein in producing insecticidal activity is not known, nor do we know if the exochitinase being bound in the toxin complex has any biological activity. Toxicity bioassay studies using Xeno Toxin Complex 1, recombinant XptA2$_{Xwi}$ and other accessory proteins from *Xenorhabdus* and *Photoharabdus*, clearly demonstrate that an exochitinase enzyme is not needed for expression of high levels of oral insecticidal activity with these proteins. What is not known is if the chitinase acts in some manner to increase insecticidal activity beyond what is expressed in its absence. Expression of exo and endochitinase genes in plants have been shown to increase the activity of Bt toxins. (Ding et al., 1998; Regev et al., 1996). Such enzymatic activity might assist in breaking down chitin barriers in the peritrophic membrane separating the toxin from its site of action in the gut of the insect. Being able to express these proteins individually in heterologous systems and obtaining them in purified form would allow more careful biochemical studies aimed at determining the individual role of each protein in producing insecticidal activity.

XptD1$_{Xwi}$ and XptE1$_{Xwi}$ are two proteins very similar to XptA2$_{Xwi}$. They may represent unique domains of XptA2$_{Xwi}$ that evolutionarily have been separated into two separate gene products. Having these proteins in purified form so that individual bioassays and binding studies may be conducted may give clues to how these proteins function in vivo. Such studies may also provide insight how the XptA2$_{Xwi}$ protein might be mutated or tuncated and still retain biological activity. The discovery of Xeno Toxin Complex 2 is an important finding and we demonstrate here the activity of these proteins with utility for insect control. It should be noted that XptD1$_{Xwi}$ and XptE1$_{Xwi}$ are about half the size of XptA2$_{Xwi}$, and thus might represent effective alternatives transgenes should they individually possess the biological potency and spectrum required for insect resistance product goal. They also provide information that can be used to engineer XptA2$_{Xwi}$ to make the protein smaller yet still retain activity.

Proteins and toxins. The present invention provides easily administered, functional proteins. The invention also provides a method for delivering insecticidal toxins that are functionally active and effective against many orders of insects, preferably lepidopteran insects.

The subject invention provides new classes of toxins having advantageous pesticidal activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or to fragments of these toxins, can be readily prepared using standard procedures. Toxins of the subject invention can be obtained from a variety of sources/source microorganisms.

One skilled in the art would readily recognize that toxins (and genes) of the subject invention can be obtained from a variety of sources. A toxin "from" or "obtainable from" the subject Xwi isolate means that the toxin (or a similar toxin) can be obtained from Xwi or some other source, such as another bacterial strain or a plant. For example, one skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources.

Delivery of toxins. There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

Polynucleotides and probes. The subject invention further provides nucleotide sequences that encode the toxins of the subject invention. The subject invention further provides methods of identifying and characterizing genes that encode pesticidal toxins. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Toxins and genes of the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "n" is used generically, "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55E C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10 N NaOH. 10% SDS can be prepared by dissolving 10 g of SDS in 50 ml of autoclaved water, diluting to 100 ml, and aliquotting.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein.

Duplex formation and stability depend on substantial complementarily between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of P-Globin Genomic Sequences and Restriction Site Analysis for Diagnosis of Sickle Cell Anemia," *Science* 230: 1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5N end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof Proteins of the subject invention can have substituted amino acids so long as they retain the characteristic pesticidal/ functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," as a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other *Bacillus, Paenibacillus, Photorhabdus,* and *Xenorhabdus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 contiguous residues (amino acid or nucleotide), corresponding to a segment (of the same size) in any of the exemplified sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as *E coli*, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B. t. toxins can be used in a truncated (core toxin) form. See, e.g., Adang el al, *Gene* 36:289-300 (1985), "Characterized full-length and truncated plasmid clones of the crystal protein of *Bacillus thuringiensis* subsp kurstaki HD-73 and their toxicity to *Manduca sexta*." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations.

Certain toxins of the subject invention have been specifically exemplified herein. As these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid similarity (and/or homology) with an exemplified toxin. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

The amino acid homology/similarity/identity will be highest in critical regions of the toxin which account for biological activity or are involved in the determination of three-dimensional configuration which is ultimately responsible for the biological activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological activity of the toxin.

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence for expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed MRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector.TM. program (IBI, New Haven, Conn.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined as well as the second and third choice of preferred codons. Afterwards, the amino acid sequence of the bacterial toxin of interest is reverse translated so that the resulting nucleic acid sequence codes for exactly the same protein as the native gene wanting to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class.sup.a | Range % G + C | Mean % G + C.sup.b |
|---|---|---|
| Metabolic Enzymes (76) | 44.4-75.3 | 59.0 (.+−.8.0) |
| Structural Proteins (18) | 48.6-70.5 | 63.6 (.+−.6.7) |
| Regulatory Proteins (5) | 57.2-68.8 | 62.0 (.+−.4.9) |
| Uncharacterized Proteins (9) | 41.5-70.3 | 64.3 (.+−.7.2) |
| All Proteins (108) | 44.4-75.3 | 60.8 (.+−.5.2) |

.sup.a Number of genes in class given in parentheses.
.sup.b Standard deviations given in parentheses.
.sup.c Combined groups mean ignored in mean calculation It is preferred that the plant optimized gene(s) encoding a bacterial toxin contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, the amino acid sequence of said protein is reverse translated into a DNA sequence utilizing a non-redundant genetic code established from a codon bias table compiled for the gene sequences for the particular plant, as shown in Table 2. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

TABLE 3

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |

TABLE 3-continued

Preferred amino acid codons for proteins expressed in maize

| Amino Acid | Codon* |
|---|---|
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

In some cases, especially for expression in plants, it can be advantageous to use truncated genes that express truncated proteins. Höfte et al. 1989, for example, discussed in the Background Section above, discussed protoxin and core toxin segments of B. t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length toxin.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia,*

*Serratia, Klebsiella, Xanthomonas, Streptomyces, Rhizobium, Rhodopseudomonas, Methylophilius, Agrobacterium, Acetohacter, Lactobacillus, Arthrobacter, Azotobacter, Leuconostoc,* and *Alcaligenes*; fungi, particularly yeast, e.g., genera *Saccharornyces, Cryptococcus, Kluyvetomyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomnyces roseus, S. odorus, Kluyveromyces veronae,* and *Aureobasidium pollulans*. Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley el al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters el al. [1978] *Mol. Gen. Genet.* 163: 181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter; a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. Nos. 4,945,050 to Cornell and 5,141,131 to DowElanco, now Dow AgroSciences, LLC). In addition, plants may be transformed using *Agrobacterium* technology, see U.S. Pat. No. 5,177,010 to University of Toledo; 5,104,310 to Texas A&M; European Patent Application 0131624B1; European Patent Applications 120516, 159418B1 and 176,112 to Schilperoot; U.S.

Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA(1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson el al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B. t. toxins. One strategy for insect resistance management would be to combine the TC toxins produced by *Xenorhabdus, Photorhabdus*, and the like with toxins such as B. t. crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26-33 (1988) and U.S. Pat. No. 5,500,365; likewise, European Patent Application 0 400 246 A1 and U.S. Pats. 5,866,784; 5,908,970; and 6,172,281 also describe transformation of a plant with two B. t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing spores and/or crystals of the subject *Paenibacillus* isolate, or recombinant microbes comprising the genes obtainable from the isolate disclosed herein, can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include Theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The affect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to reengineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of the *Xenorhabdus* Xwi isolate of the invention can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

We claim:

1. An isolated polynucleotide of SEQ ID NO:3.
2. A DNA molecule comprising a nucleic acid sequence encoding the polypeptide of SEQ ID NO: 4 operatively associated with a heterologous promoter.
3. A transgenic microorganism comprising the DNA of claim 2.
4. A transgenic plant comprising the DNA of claim 2.
5. A transgenic plant cell comprising the DNA of claim 2.
6. A transgenic seed comprising the plant cell of claim 5.
7. An isolated polynucleotide that encodes the polypeptide of SEQ ID NO: 4 (XptE1$_{Xwi}$).
8. A purified bacterial cell comprising the isolated polynucleotide of claim 7.
9. An isolated polynucleotide that encodes a protein at least 99% identical to SEQ ID NO: 4.

* * * * *

SEQUENCE LISTING

<160> NUMBER OF SEQ ID NOS: 23

<210> SEQ ID NO 1
<211> LENGTH: 4176
<212> TYPE: DNA
<213> ORGANISM: Xenorhabdus nematophilus str. Xwi
<220> FEATURE:
<221> NAME/KEY: CDS
<222> LOCATION: (1)..(4173)

<400> SEQUENCE: 1

```
atg agt tca gtt acc caa cct att gaa gag cgt tta ctg gaa tca cag       48
Met Ser Ser Val Thr Gln Pro Ile Glu Glu Arg Leu Leu Glu Ser Gln
1               5                   10                  15 cgc gac gca ctg ctg gat ttc tat ctc gga cag gtc gtt gcc tat tca       96
Arg Asp Ala Leu Leu Asp Phe Tyr Leu Gly Gln Val Val Ala Tyr Ser
                20                  25                  30 cct gac atg aca agt cag cgc gac aaa att aag gat att gac gat gcc      144
Pro Asp Met Thr Ser Gln Arg Asp Lys Ile Lys Asp Ile Asp Asp Ala
            35                  40                  45 tgc gac tac ctc ctg ctg gat ctg ctg act tcc gcc aaa gtc aaa gcg      192
Cys Asp Tyr Leu Leu Leu Asp Leu Leu Thr Ser Ala Lys Val Lys Ala
        50                  55                  60 aca cga ctt tca ctt gcg acc aat tca ttg cag caa ttt gtg aac cgc      240
Thr Arg Leu Ser Leu Ala Thr Asn Ser Leu Gln Gln Phe Val Asn Arg
65                  70                  75                  80 gtg tca ctg aat att gaa ccc ggt ttg ttt atg acc gcg gaa gag agc      288
Val Ser Leu Asn Ile Glu Pro Gly Leu Phe Met Thr Ala Glu Glu Ser
                85                  90                  95 gaa aat tgg cag gaa ttt gcg aat cgt tat aat tac tgg tct gcg gat      336
Glu Asn Trp Gln Glu Phe Ala Asn Arg Tyr Asn Tyr Trp Ser Ala Asp
                100                 105                 110 cgc tta tta cgg act tat ccg gaa agc tat ctg gaa ccc ctg tta cgc      384
Arg Leu Leu Arg Thr Tyr Pro Glu Ser Tyr Leu Glu Pro Leu Leu Arg
            115                 120                 125 ctg aat aaa aca gaa ttc ttc ttc caa ctg gaa agt gcc ctt aat cag      432
Leu Asn Lys Thr Glu Phe Phe Phe Gln Leu Glu Ser Ala Leu Asn Gln
        130                 135                 140 gga aaa att acc gaa gat tcc gta caa caa gcg gtg ctc ggt tat ctg      480
Gly Lys Ile Thr Glu Asp Ser Val Gln Gln Ala Val Leu Gly Tyr Leu
145                 150                 155                 160 aat aat ttt gaa gat gtc agt aac ctg aaa gtt atc gca ggt tat gaa      528
Asn Asn Phe Glu Asp Val Ser Asn Leu Lys Val Ile Ala Gly Tyr Glu
                165                 170                 175 gat ggt gtt aac atc aaa cgc gat aag ttc ttc ttt gtc gga cgt acc      576
Asp Gly Val Asn Ile Lys Arg Asp Lys Phe Phe Phe Val Gly Arg Thr
                180                 185                 190
```

```
cgt aca cag cca tac caa tat tac tgg cgt tca ctg aat ctt tcg ata    624
Arg Thr Gln Pro Tyr Gln Tyr Tyr Trp Arg Ser Leu Asn Leu Ser Ile
            195                 200                 205 cgc cat cct gat acc gat gcg tta tct ccc aat gcc tgg agc gag tgg    672
Arg His Pro Asp Thr Asp Ala Leu Ser Pro Asn Ala Trp Ser Glu Trp
    210                 215                 220 aaa cct att gac ctg cca ttg ggc agc gta gac ccc aat ttg ata cgc    720
Lys Pro Ile Asp Leu Pro Leu Gly Ser Val Asp Pro Asn Leu Ile Arg
225                 230                 235                 240 ccc att ttc ctg aat aat cgc ctg tat att gcc tgg acg gaa gtt gaa    768
Pro Ile Phe Leu Asn Asn Arg Leu Tyr Ile Ala Trp Thr Glu Val Glu
                245                 250                 255 gaa cag tct gaa act aaa gat aca act gcg tta tca ctg cat aac caa    816
Glu Gln Ser Glu Thr Lys Asp Thr Thr Ala Leu Ser Leu His Asn Gln
            260                 265                 270 aac gtt gag cct agt gcg ggt gat tgg gtt cct ccc aca ccg ttc ctg    864
Asn Val Glu Pro Ser Ala Gly Asp Trp Val Pro Pro Thr Pro Phe Leu
        275                 280                 285 acc cgg atc aaa atc gct tat gcc aaa tat gat ggc agc tgg agt aca    912
Thr Arg Ile Lys Ile Ala Tyr Ala Lys Tyr Asp Gly Ser Trp Ser Thr
    290                 295                 300 ccc acc att ctg cgc gaa gac aat ctg caa tac cgg atg gcc cag atg    960
Pro Thr Ile Leu Arg Glu Asp Asn Leu Gln Tyr Arg Met Ala Gln Met
305                 310                 315                 320 gtt gct gtg atg gat ata cag caa gac ccg cat aac ccg ttt ctg gct   1008
Val Ala Val Met Asp Ile Gln Gln Asp Pro His Asn Pro Phe Leu Ala
                325                 330                 335 ctg gtt ccg ttt gtc cgt ctt cag ggg aca gat aag aaa ggt aag gat   1056
Leu Val Pro Phe Val Arg Leu Gln Gly Thr Asp Lys Lys Gly Lys Asp
            340                 345                 350 tat gat tat gac gaa gcc ttc ggt tat gtc tgc gat aca ctg ctg gta   1104
Tyr Asp Tyr Asp Glu Ala Phe Gly Tyr Val Cys Asp Thr Leu Leu Val
        355                 360                 365 gaa att act gat ttg ccg gat gac gaa tat gct gat gga cga aaa gga   1152
Glu Ile Thr Asp Leu Pro Asp Asp Glu Tyr Ala Asp Gly Arg Lys Gly
    370                 375                 380 aaa tat gtc ggc aac ctg gtc tgg tat tac tca cgt gaa cac aag gat   1200
Lys Tyr Val Gly Asn Leu Val Trp Tyr Tyr Ser Arg Glu His Lys Asp
385                 390                 395                 400 gca gaa ggc aat cct atc gat tac cgt act atg gtg ctc tat ccg gca   1248
Ala Glu Gly Asn Pro Ile Asp Tyr Arg Thr Met Val Leu Tyr Pro Ala
                405                 410                 415 acc cgg gaa gaa cgc ttt cct att gcc gga gaa gcc aaa ccg gaa gga   1296
Thr Arg Glu Glu Arg Phe Pro Ile Ala Gly Glu Ala Lys Pro Glu Gly
            420                 425                 430 agc cct gat ttt ggc aaa gac agt atc aaa ctg att gtc aat ttt gtt   1344
Ser Pro Asp Phe Gly Lys Asp Ser Ile Lys Leu Ile Val Asn Phe Val
        435                 440                 445 cat ggc act gat gac aca ctg gag att gtc gct caa tct gac ttt aag   1392
His Gly Thr Asp Asp Thr Leu Glu Ile Val Ala Gln Ser Asp Phe Lys
    450                 455                 460 ttt ggt gcg ata gaa gat cat caa tat tac aac ggt tct ttc cgg ctg   1440
Phe Gly Ala Ile Glu Asp His Gln Tyr Tyr Asn Gly Ser Phe Arg Leu
465                 470                 475                 480 atg cac gat aat act gtc ttg gat gaa caa cca ctg gta ctg aac gaa   1488
Met His Asp Asn Thr Val Leu Asp Glu Gln Pro Leu Val Leu Asn Glu
                485                 490                 495 aaa gtt cct gat tta acc tat cca tca atc aag ctg ggg tcg gat aat   1536
Lys Val Pro Asp Leu Thr Tyr Pro Ser Ile Lys Leu Gly Ser Asp Asn
```

-continued

```
                500                 505                 510
cga atc acc ctg aaa gcc gaa ctt ctc ttt aag ccc aaa ggt ggt gtt      1584
Arg Ile Thr Leu Lys Ala Glu Leu Leu Phe Lys Pro Lys Gly Gly Val
        515                 520                 525 ggc aat gaa agt gcc agc tgt act caa gag ttc aga atc ggt atg cac      1632
Gly Asn Glu Ser Ala Ser Cys Thr Gln Glu Phe Arg Ile Gly Met His
    530                 535                 540 att cgc gaa ctg att aaa ctc aat gaa cag gat cag gtg caa ttc ctt      1680
Ile Arg Glu Leu Ile Lys Leu Asn Glu Gln Asp Gln Val Gln Phe Leu
545                 550                 555                 560 tcc ttc ccc gca gat gaa act ggt aac gcg cca caa aac att cgc ctt      1728
Ser Phe Pro Ala Asp Glu Thr Gly Asn Ala Pro Gln Asn Ile Arg Leu
                565                 570                 575 aat aca ctg ttt gca aaa aaa ctg atc gcc att gcc agt cag ggt atc      1776
Asn Thr Leu Phe Ala Lys Lys Leu Ile Ala Ile Ala Ser Gln Gly Ile
            580                 585                 590 ccg cag gta ctg agc tgg aat aca cag ctt att act gaa caa ccc ata      1824
Pro Gln Val Leu Ser Trp Asn Thr Gln Leu Ile Thr Glu Gln Pro Ile
        595                 600                 605 ccc ggt tca ttc cct acg ccg att gat tta aat ggc gca aat ggg atc      1872
Pro Gly Ser Phe Pro Thr Pro Ile Asp Leu Asn Gly Ala Asn Gly Ile
    610                 615                 620 tat ttc tgg gaa ctg ttt ttc cat atg cca ttt ctg gtc gcg tgg cga      1920
Tyr Phe Trp Glu Leu Phe Phe His Met Pro Phe Leu Val Ala Trp Arg
625                 630                 635                 640 ctg aat atc gaa caa cga tta aaa gag gcc acc gaa tgg ctg cac tat      1968
Leu Asn Ile Glu Gln Arg Leu Lys Glu Ala Thr Glu Trp Leu His Tyr
                645                 650                 655 att ttt aat ccg ctg gaa gat gaa ctt gtt cag gcc agc aac caa ggt      2016
Ile Phe Asn Pro Leu Glu Asp Glu Leu Val Gln Ala Ser Asn Gln Gly
            660                 665                 670 aaa ccg cgt tac tgg aat tca cgg cca att att gat cct cca ccc acc      2064
Lys Pro Arg Tyr Trp Asn Ser Arg Pro Ile Ile Asp Pro Pro Pro Thr
        675                 680                 685 gtg tac cgg atg tta att gaa cca acc gat ccg gat gcc att gca gcc      2112
Val Tyr Arg Met Leu Ile Glu Pro Thr Asp Pro Asp Ala Ile Ala Ala
    690                 695                 700 agt gaa ccc att cac tac cgg aaa gca ata ttc cgt ttc tat gtc aag      2160
Ser Glu Pro Ile His Tyr Arg Lys Ala Ile Phe Arg Phe Tyr Val Lys
705                 710                 715                 720 aat ctg tta gat cag gga gac atg gaa tac cgt aag ctg aca tcc agt      2208
Asn Leu Leu Asp Gln Gly Asp Met Glu Tyr Arg Lys Leu Thr Ser Ser
                725                 730                 735 gca cgt act gtc gcc aag cag atc tat gac tcc gtc aat atg tta ctg      2256
Ala Arg Thr Val Ala Lys Gln Ile Tyr Asp Ser Val Asn Met Leu Leu
            740                 745                 750 ggt acc agc cct gat att ctg ctc gcg gca aac tgg caa ccc cgt acg      2304
Gly Thr Ser Pro Asp Ile Leu Leu Ala Ala Asn Trp Gln Pro Arg Thr
        755                 760                 765 ctg caa gat gtg gct ctg tat gaa aac agt gaa gca cgg gca cag gag      2352
Leu Gln Asp Val Ala Leu Tyr Glu Asn Ser Glu Ala Arg Ala Gln Glu
    770                 775                 780 tta atg ctt act gtc agc agc gtg cca ctt ctg cct gtg aca tat gat      2400
Leu Met Leu Thr Val Ser Ser Val Pro Leu Leu Pro Val Thr Tyr Asp
785                 790                 795                 800 aca tcc gtc tct gcc gca ccg tct gat tta ttt gtc aaa cct gtt gat      2448
Thr Ser Val Ser Ala Ala Pro Ser Asp Leu Phe Val Lys Pro Val Asp
                805                 810                 815 acg gaa tat ctc aaa ctg tgg caa atg ttg gat cag cgt cta tat aac      2496
Thr Glu Tyr Leu Lys Leu Trp Gln Met Leu Asp Gln Arg Leu Tyr Asn
```

```
                Thr Glu Tyr Leu Lys Leu Trp Gln Met Leu Asp Gln Arg Leu Tyr Asn
                                820                 825                 830 tta cgt cat aac ctg acc ttg gat ggt aaa gag ttt ccg gcc gga tta              2544
Leu Arg His Asn Leu Thr Leu Asp Gly Lys Glu Phe Pro Ala Gly Leu
            835                 840                 845 tac gat gaa ccc atc agc ccg caa gat ctg ctc agg cag cgt tac cag              2592
Tyr Asp Glu Pro Ile Ser Pro Gln Asp Leu Leu Arg Gln Arg Tyr Gln
850                 855                 860 cgt gtt gtg gct aat cgt atg gcg ggc atg aaa cgc cgg gca atc ccg              2640
Arg Val Val Ala Asn Arg Met Ala Gly Met Lys Arg Arg Ala Ile Pro
865                 870                 875                 880 aat tat cgt ttc acc ccg atc atg agc cgg gca aaa gag gcc gca gaa              2688
Asn Tyr Arg Phe Thr Pro Ile Met Ser Arg Ala Lys Glu Ala Ala Glu
                885                 890                 895 acg ctg att cag tac ggc agc acg tta ctg agt ttg ctg gag aaa aaa              2736
Thr Leu Ile Gln Tyr Gly Ser Thr Leu Leu Ser Leu Leu Glu Lys Lys
            900                 905                 910 gac aat acc gat ttt gaa cac ttc cgt atg cag cag caa ctg ggg ctg              2784
Asp Asn Thr Asp Phe Glu His Phe Arg Met Gln Gln Gln Leu Gly Leu
        915                 920                 925 tac agc ttt acc cgc aat ctg caa cag caa gcg att gac atg caa cag              2832
Tyr Ser Phe Thr Arg Asn Leu Gln Gln Gln Ala Ile Asp Met Gln Gln
    930                 935                 940 gct tca ttg gat gca ctg acc atc agc cga cgg gcc gct cag gag cgc              2880
Ala Ser Leu Asp Ala Leu Thr Ile Ser Arg Arg Ala Ala Gln Glu Arg
945                 950                 955                 960 cag caa cac tat aaa tcg ctc tat gat gaa aac atc tcc atc acc gag              2928
Gln Gln His Tyr Lys Ser Leu Tyr Asp Glu Asn Ile Ser Ile Thr Glu
                965                 970                 975 cag gaa gtt atc gca tta caa tca aga gcg gct gaa ggt gtg atc gct              2976
Gln Glu Val Ile Ala Leu Gln Ser Arg Ala Ala Glu Gly Val Ile Ala
            980                 985                 990 gcc cag tca gcc gcc act gcg gcc gct gtg gcg gat atg gtt ccc aat              3024
Ala Gln Ser Ala Ala Thr Ala Ala Ala Val Ala Asp Met Val Pro Asn
        995                 1000                1005 att ttc ggt ctg gcc gtc ggg ggg atg gtc ttt ggc ggt atg ctt              3069
Ile Phe Gly Leu Ala Val Gly Gly Met Val Phe Gly Gly Met Leu
    1010                1015                1020 cgg gca atc ggt gaa gga ata cgc att gac gtt gaa agt aaa aat              3114
Arg Ala Ile Gly Glu Gly Ile Arg Ile Asp Val Glu Ser Lys Asn
1025                1030                1035 gcc aaa gcc acc agc ctg agc gtg tca gaa aat tac cgt cgc cgt              3159
Ala Lys Ala Thr Ser Leu Ser Val Ser Glu Asn Tyr Arg Arg Arg
    1040                1045                1050 cag caa gaa tgg gag ctg caa tac aaa cag gcg gat atc aac att              3204
Gln Gln Glu Trp Glu Leu Gln Tyr Lys Gln Ala Asp Ile Asn Ile
    1055                1060                1065 gag gag atc gac gca cag att ggt atc cag caa cgc caa ctg aat              3249
Glu Glu Ile Asp Ala Gln Ile Gly Ile Gln Gln Arg Gln Leu Asn
    1070                1075                1080 atc agc aca acc caa ctg gca caa ttg gaa gcc cag cat gag cag              3294
Ile Ser Thr Thr Gln Leu Ala Gln Leu Glu Ala Gln His Glu Gln
    1085                1090                1095 gat caa gtc ctg ctg gag tac tat tca aac cgt ttt acc aat gat              3339
Asp Gln Val Leu Leu Glu Tyr Tyr Ser Asn Arg Phe Thr Asn Asp
    1100                1105                1110 gcg tta tac atg tgg atg atc agc caa atc tcc ggg ctt tac ctg              3384
Ala Leu Tyr Met Trp Met Ile Ser Gln Ile Ser Gly Leu Tyr Leu
    1115                1120                1125
```

```
caa gcc tat gat gcg gtt aat tcc ctc tgt tta ctg gcc gaa gcc    3429
Gln Ala Tyr Asp Ala Val Asn Ser Leu Cys Leu Leu Ala Glu Ala
    1130                1135                1140 tcc tgg cag tac gaa aca ggt cag tat gat atg aat ttc gtc caa    3474
Ser Trp Gln Tyr Glu Thr Gly Gln Tyr Asp Met Asn Phe Val Gln
1145                1150                1155 agt ggt ctc tgg aat gat ctt tat cag ggg ctg ctg gtc gga gaa    3519
Ser Gly Leu Trp Asn Asp Leu Tyr Gln Gly Leu Leu Val Gly Glu
    1160                1165                1170 cat ctg aaa tta gcc tta caa cgg atg gat cag gcg tat ttg caa    3564
His Leu Lys Leu Ala Leu Gln Arg Met Asp Gln Ala Tyr Leu Gln
1175                1180                1185 cat aac acc aga cgt ctg gag atc ata aaa acc ata tcg gta aaa    3609
His Asn Thr Arg Arg Leu Glu Ile Ile Lys Thr Ile Ser Val Lys
    1190                1195                1200 tca tta ctg aca tca tca cag tgg gaa att ggc aag agt acg ggt    3654
Ser Leu Leu Thr Ser Ser Gln Trp Glu Ile Gly Lys Ser Thr Gly
1205                1210                1215 tca ttc act ttc tta ctg agc gcc gaa atg ttc ttg cgc gat tat    3699
Ser Phe Thr Phe Leu Leu Ser Ala Glu Met Phe Leu Arg Asp Tyr
    1220                1225                1230 ccg acc cac gct gat cgg cgt ata aaa acc gta gcg ctg tca ttg    3744
Pro Thr His Ala Asp Arg Arg Ile Lys Thr Val Ala Leu Ser Leu
1235                1240                1245 ccc gca ttg ctg ggg cct tat gaa gat gta cgg gct tca ctg gta    3789
Pro Ala Leu Leu Gly Pro Tyr Glu Asp Val Arg Ala Ser Leu Val
    1250                1255                1260 caa ctc agc aat acg ctt tac agt act gct gac tta aaa act atc    3834
Gln Leu Ser Asn Thr Leu Tyr Ser Thr Ala Asp Leu Lys Thr Ile
1265                1270                1275 gat tat ttg ctt aac ccc ttg gaa tac acc aaa ccc gaa aac gtt    3879
Asp Tyr Leu Leu Asn Pro Leu Glu Tyr Thr Lys Pro Glu Asn Val
    1280                1285                1290 ttg ctg aac gta cag gct aat caa ggt gtg gtg att tca acg gcc    3924
Leu Leu Asn Val Gln Ala Asn Gln Gly Val Val Ile Ser Thr Ala
1295                1300                1305 atg gaa gac agc ggc atg ttc agg ctc aat ttt gat gat gaa ctt    3969
Met Glu Asp Ser Gly Met Phe Arg Leu Asn Phe Asp Asp Glu Leu
    1310                1315                1320 ttc ctg cct ttt gaa ggg aca ggc gcc att tca cag tgg aag ttg    4014
Phe Leu Pro Phe Glu Gly Thr Gly Ala Ile Ser Gln Trp Lys Leu
1325                1330                1335 gaa ttc ggt tcc gat cag gat cag ctg ctg gag tcg ctg agc gat    4059
Glu Phe Gly Ser Asp Gln Asp Gln Leu Leu Glu Ser Leu Ser Asp
    1340                1345                1350 att atc ctc cat ctg cgt tat acc gcg cgt gat gtg agt ggc gga    4104
Ile Ile Leu His Leu Arg Tyr Thr Ala Arg Asp Val Ser Gly Gly
1355                1360                1365 agt aat gag ttc agc cag cag gtt cgt agc cgt ctg aat aaa cat    4149
Ser Asn Glu Phe Ser Gln Gln Val Arg Ser Arg Leu Asn Lys His
    1370                1375                1380 caa tta aaa caa gac aat tct aac tga                            4176
Gln Leu Lys Gln Asp Asn Ser Asn
1385                1390

<210> SEQ ID NO 2
<211> LENGTH: 1391
<212> TYPE: PRT
<213> ORGANISM: Xenorhabdus nematophilus str. Xwi

<400> SEQUENCE: 2
```

-continued

```
Met Ser Ser Val Thr Gln Pro Ile Glu Glu Arg Leu Leu Ser Gln
1               5                   10                  15

Arg Asp Ala Leu Leu Asp Phe Tyr Leu Gly Gln Val Ala Tyr Ser
            20                  25                  30

Pro Asp Met Thr Ser Gln Arg Asp Lys Ile Lys Asp Ile Asp Ala
        35                  40                  45

Cys Asp Tyr Leu Leu Asp Leu Leu Thr Ser Ala Lys Val Lys Ala
    50                  55                  60

Thr Arg Leu Ser Leu Ala Thr Asn Ser Leu Gln Gln Phe Val Asn Arg
65                  70                  75                  80

Val Ser Leu Asn Ile Glu Pro Gly Leu Phe Met Thr Ala Glu Glu Ser
                85                  90                  95

Glu Asn Trp Gln Glu Phe Ala Asn Arg Tyr Asn Tyr Trp Ser Ala Asp
            100                 105                 110

Arg Leu Leu Arg Thr Tyr Pro Glu Ser Tyr Leu Glu Pro Leu Leu Arg
        115                 120                 125

Leu Asn Lys Thr Glu Phe Phe Phe Gln Leu Glu Ser Ala Leu Asn Gln
    130                 135                 140

Gly Lys Ile Thr Glu Asp Ser Val Gln Gln Ala Val Leu Gly Tyr Leu
145                 150                 155                 160

Asn Asn Phe Glu Asp Val Ser Asn Leu Lys Val Ile Ala Gly Tyr Glu
                165                 170                 175

Asp Gly Val Asn Ile Lys Arg Asp Lys Phe Phe Phe Val Gly Arg Thr
            180                 185                 190

Arg Thr Gln Pro Tyr Gln Tyr Tyr Trp Arg Ser Leu Asn Leu Ser Ile
        195                 200                 205

Arg His Pro Asp Thr Asp Ala Leu Ser Pro Asn Ala Trp Ser Glu Trp
    210                 215                 220

Lys Pro Ile Asp Leu Pro Leu Gly Ser Val Asp Pro Asn Leu Ile Arg
225                 230                 235                 240

Pro Ile Phe Leu Asn Asn Arg Leu Tyr Ile Ala Trp Thr Glu Val Glu
                245                 250                 255

Glu Gln Ser Glu Thr Lys Asp Thr Thr Ala Leu Ser Leu His Asn Gln
            260                 265                 270

Asn Val Glu Pro Ser Ala Gly Asp Trp Val Pro Thr Pro Phe Leu
        275                 280                 285

Thr Arg Ile Lys Ile Ala Tyr Ala Lys Tyr Asp Gly Ser Trp Ser Thr
    290                 295                 300

Pro Thr Ile Leu Arg Glu Asp Asn Leu Gln Tyr Arg Met Ala Gln Met
305                 310                 315                 320

Val Ala Val Met Asp Ile Gln Gln Asp Pro His Asn Pro Phe Leu Ala
                325                 330                 335

Leu Val Pro Phe Val Arg Leu Gln Gly Thr Lys Lys Gly Lys Asp
            340                 345                 350

Tyr Asp Tyr Asp Glu Ala Phe Gly Tyr Val Cys Asp Thr Leu Leu Val
        355                 360                 365

Glu Ile Thr Asp Leu Pro Asp Glu Tyr Ala Asp Gly Arg Lys Gly
    370                 375                 380

Lys Tyr Val Gly Asn Leu Val Trp Tyr Ser Arg Glu His Lys Asp
385                 390                 395                 400

Ala Glu Gly Asn Pro Ile Asp Tyr Arg Thr Met Val Leu Tyr Pro Ala
                405                 410                 415
```

-continued

```
Thr Arg Glu Glu Arg Phe Pro Ile Ala Gly Glu Ala Lys Pro Glu Gly
            420                 425                 430

Ser Pro Asp Phe Gly Lys Asp Ser Ile Lys Leu Ile Val Asn Phe Val
            435                 440                 445

His Gly Thr Asp Thr Leu Glu Ile Val Ala Gln Ser Asp Phe Lys
            450                 455                 460

Phe Gly Ala Ile Glu Asp His Gln Tyr Tyr Asn Gly Ser Phe Arg Leu
465                 470                 475                 480

Met His Asp Asn Thr Val Leu Asp Glu Gln Pro Leu Val Leu Asn Glu
            485                 490                 495

Lys Val Pro Asp Leu Thr Tyr Pro Ser Ile Lys Leu Gly Ser Asp Asn
            500                 505                 510

Arg Ile Thr Leu Lys Ala Glu Leu Leu Phe Lys Pro Lys Gly Gly Val
            515                 520                 525

Gly Asn Glu Ser Ala Ser Cys Thr Gln Glu Phe Arg Ile Gly Met His
            530                 535                 540

Ile Arg Glu Leu Ile Lys Leu Asn Glu Gln Asp Gln Val Gln Phe Leu
545                 550                 555                 560

Ser Phe Pro Ala Asp Glu Thr Gly Asn Ala Pro Gln Asn Ile Arg Leu
            565                 570                 575

Asn Thr Leu Phe Ala Lys Lys Leu Ile Ala Ile Ala Ser Gln Gly Ile
            580                 585                 590

Pro Gln Val Leu Ser Trp Asn Thr Gln Leu Ile Thr Glu Gln Pro Ile
            595                 600                 605

Pro Gly Ser Phe Pro Thr Pro Ile Asp Leu Asn Gly Ala Asn Gly Ile
            610                 615                 620

Tyr Phe Trp Glu Leu Phe Phe His Met Pro Phe Leu Val Ala Trp Arg
625                 630                 635                 640

Leu Asn Ile Glu Gln Arg Leu Lys Glu Ala Thr Glu Trp Leu His Tyr
            645                 650                 655

Ile Phe Asn Pro Leu Glu Asp Glu Leu Val Gln Ala Ser Asn Gln Gly
            660                 665                 670

Lys Pro Arg Tyr Trp Asn Ser Arg Pro Ile Ile Asp Pro Pro Thr
            675                 680                 685

Val Tyr Arg Met Leu Ile Glu Pro Thr Asp Pro Asp Ala Ile Ala Ala
            690                 695                 700

Ser Glu Pro Ile His Tyr Arg Lys Ala Ile Phe Arg Phe Tyr Val Lys
705                 710                 715                 720

Asn Leu Leu Asp Gln Gly Asp Met Glu Tyr Arg Lys Leu Thr Ser Ser
            725                 730                 735

Ala Arg Thr Val Ala Lys Gln Ile Tyr Asp Ser Val Asn Met Leu Leu
            740                 745                 750

Gly Thr Ser Pro Asp Ile Leu Leu Ala Ala Asn Trp Gln Pro Arg Thr
            755                 760                 765

Leu Gln Asp Val Ala Leu Tyr Glu Asn Ser Glu Ala Arg Ala Gln Glu
            770                 775                 780

Leu Met Leu Thr Val Ser Val Pro Leu Pro Val Thr Tyr Asp
785                 790                 795                 800

Thr Ser Val Ser Ala Ala Pro Ser Asp Leu Phe Val Lys Pro Val Asp
            805                 810                 815

Thr Glu Tyr Leu Lys Leu Trp Gln Met Leu Asp Gln Arg Leu Tyr Asn
            820                 825                 830

Leu Arg His Asn Leu Thr Leu Asp Gly Lys Glu Phe Pro Ala Gly Leu
```

-continued

```
            835                 840                 845
Tyr Asp Glu Pro Ile Ser Pro Gln Asp Leu Leu Arg Gln Arg Tyr Gln
    850                 855                 860
Arg Val Val Ala Asn Arg Met Ala Gly Met Lys Arg Arg Ala Ile Pro
865                 870                 875                 880
Asn Tyr Arg Phe Thr Pro Ile Met Ser Arg Ala Lys Glu Ala Ala Glu
                    885                 890                 895
Thr Leu Ile Gln Tyr Gly Ser Thr Leu Leu Ser Leu Leu Glu Lys Lys
                900                 905                 910
Asp Asn Thr Asp Phe Glu His Phe Arg Met Gln Gln Gln Leu Gly Leu
            915                 920                 925
Tyr Ser Phe Thr Arg Asn Leu Gln Gln Gln Ala Ile Asp Met Gln Gln
    930                 935                 940
Ala Ser Leu Asp Ala Leu Thr Ile Ser Arg Arg Ala Ala Gln Glu Arg
945                 950                 955                 960
Gln Gln His Tyr Lys Ser Leu Tyr Asp Glu Asn Ile Ser Ile Thr Glu
                    965                 970                 975
Gln Glu Val Ile Ala Leu Gln Ser Arg Ala Ala Glu Gly Val Ile Ala
                980                 985                 990
Ala Gln Ser Ala Ala Thr Ala Ala  Ala Val Ala Asp Met  Val Pro Asn
            995                 1000                1005
Ile Phe  Gly Leu Ala Val  Gly Gly Met Val Phe Gly  Gly Met Leu
    1010                1015                1020
Arg Ala  Ile Gly Glu Gly  Ile Arg Ile Asp Val Glu  Ser Lys Asn
    1025                1030                1035
Ala Lys  Ala Thr Ser Leu  Ser Val Ser Glu Asn Tyr  Arg Arg Arg
    1040                1045                1050
Gln Gln  Glu Trp Glu Leu Gln  Tyr Lys Gln Ala Asp  Ile Asn Ile
    1055                1060                1065
Glu Glu  Ile Asp Ala Gln Ile  Gly Ile Gln Arg  Gln Leu Asn
    1070                1075                1080
Ile Ser  Thr Thr Gln Leu Ala  Gln Leu Glu Ala Gln  His Glu Gln
    1085                1090                1095
Asp Gln  Val Leu Leu Glu Tyr  Tyr Ser Asn Arg Phe  Thr Asn Asp
    1100                1105                1110
Ala Leu  Tyr Met Trp Met  Ile Ser Gln Ile Ser Gly  Leu Tyr Leu
    1115                1120                1125
Gln Ala  Tyr Asp Ala Val Asn  Ser Leu Cys Leu Leu  Ala Glu Ala
    1130                1135                1140
Ser Trp  Gln Tyr Glu Thr Gly  Gln Tyr Asp Met Asn  Phe Val Gln
    1145                1150                1155
Ser Gly  Leu Trp Asn Asp Leu  Tyr Gln Gly Leu Leu  Val Gly Glu
    1160                1165                1170
His Leu  Lys Leu Ala Leu Gln  Arg Met Asp Gln Ala  Tyr Leu Gln
    1175                1180                1185
His Asn  Thr Arg Arg Leu Glu  Ile Ile Lys Thr Ile  Ser Val Lys
    1190                1195                1200
Ser Leu  Leu Thr Ser Ser Gln  Trp Glu Ile Gly Lys  Ser Thr Gly
    1205                1210                1215
Ser Phe  Thr Phe Leu Leu Ser  Ala Glu Met Phe Leu  Arg Asp Tyr
    1220                1225                1230
Pro Thr  His Ala Asp Arg Arg  Ile Lys Thr Val Ala  Leu Ser Leu
    1235                1240                1245
```

-continued

```
Pro Ala Leu Leu Gly Pro Tyr Glu Asp Val Arg Ala Ser Leu Val
    1250                1255                1260

Gln Leu Ser Asn Thr Leu Tyr Ser Thr Ala Asp Leu Lys Thr Ile
    1265                1270                1275

Asp Tyr Leu Leu Asn Pro Leu Glu Tyr Thr Lys Pro Glu Asn Val
    1280                1285                1290

Leu Leu Asn Val Gln Ala Asn Gln Gly Val Val Ile Ser Thr Ala
    1295                1300                1305

Met Glu Asp Ser Gly Met Phe Arg Leu Asn Phe Asp Asp Glu Leu
    1310                1315                1320

Phe Leu Pro Phe Glu Gly Thr Gly Ala Ile Ser Gln Trp Lys Leu
    1325                1330                1335

Glu Phe Gly Ser Asp Gln Asp Gln Leu Leu Glu Ser Leu Ser Asp
    1340                1345                1350

Ile Ile Leu His Leu Arg Tyr Thr Ala Arg Asp Val Ser Gly Gly
    1355                1360                1365

Ser Asn Glu Phe Ser Gln Gln Val Arg Ser Arg Leu Asn Lys His
    1370                1375                1380

Gln Leu Lys Gln Asp Asn Ser Asn
    1385                1390

<210> SEQ ID NO 3
<211> LENGTH: 3471
<212> TYPE: DNA
<213> ORGANISM: Xenorhabdus nematophilus str. Xwi
<220> FEATURE:
<221> NAME/KEY: CDS
<222> LOCATION: (1)..(3468)

<400> SEQUENCE: 3 atg cat aca aca tca aca gat gag aaa act ata acg cct ctg ctg gcg       48
Met His Thr Thr Ser Thr Asp Glu Lys Thr Ile Thr Pro Leu Leu Ala
1               5                   10                  15 tct gca ttt atg cag gcc cag cat tcc gct caa cga ctg caa tca atg       96
Ser Ala Phe Met Gln Ala Gln His Ser Ala Gln Arg Leu Gln Ser Met
            20                  25                  30 gaa cag agc cat aat gaa ctg agt cgt tgg gga tat ttc tcg gta ttt      144
Glu Gln Ser His Asn Glu Leu Ser Arg Trp Gly Tyr Phe Ser Val Phe
        35                  40                  45 gat att gtc aaa gtc gga cca tca cgt ttc aga cgc gcc cac agg cat      192
Asp Ile Val Lys Val Gly Pro Ser Arg Phe Arg Arg Arg His Arg His
    50                  55                  60 cat ttt aac ggt caa gca gaa acg ctt tac caa aac gcg ctc agc tat      240
His Phe Asn Gly Gln Ala Glu Thr Leu Tyr Gln Asn Ala Leu Ser Tyr
65                  70                  75                  80 gca act cag ttg att cac agt gcc cgc gaa cgg gga tta cgt gat gcc      288
Ala Thr Gln Leu Ile His Ser Ala Arg Glu Arg Gly Leu Arg Asp Ala
                85                  90                  95 gaa acg tta cgt atg gcc cgt gtt gcg tca gga caa ccg gaa tta ccc      336
Glu Thr Leu Arg Met Ala Arg Val Ala Ser Gly Gln Pro Glu Leu Pro
            100                 105                 110 aac tat gct gat ctc ttt ccg gaa cct tgg gat aat ttt tgt aaa ccc      384
Asn Tyr Ala Asp Leu Phe Pro Glu Pro Trp Asp Asn Phe Cys Lys Pro
        115                 120                 125 ggc gca ctt gag gca ctg aat tcc cct gcc gct tat ctg ctg gaa tta      432
Gly Ala Leu Glu Ala Leu Asn Ser Pro Ala Ala Tyr Leu Leu Glu Leu
    130                 135                 140 tac cag ttt gcc cgc cag ctt gag ctg gat gca act gaa ggt gcg att      480
```

```
Tyr Gln Phe Ala Arg Gln Leu Glu Leu Asp Ala Thr Glu Gly Ala Ile
145                 150                 155                 160 ggt ttt gcc caa cga cgc ccg gat att cca gaa cta ttg ttg gat cgc      528
Gly Phe Ala Gln Arg Arg Pro Asp Ile Pro Glu Leu Leu Leu Asp Arg
                165                 170                 175 gat aat acg aat cag gag ctg ccg gca tta caa ata gtc aat gaa att      576
Asp Asn Thr Asn Gln Glu Leu Pro Ala Leu Gln Ile Val Asn Glu Ile
            180                 185                 190 ctc tcc ttt atc gcc gct gat tat atc gat cat agt cag gaa acg ggc      624
Leu Ser Phe Ile Ala Ala Asp Tyr Ile Asp His Ser Gln Glu Thr Gly
        195                 200                 205 aaa ccg gtt aac cag gtg ttg gga gaa aca tac tac cct tat acg ctg      672
Lys Pro Val Asn Gln Val Leu Gly Glu Thr Tyr Tyr Pro Tyr Thr Leu
    210                 215                 220 cct ttc agt ctc gca aca tta cag gtc aca ctt ggc tta gca gat aaa      720
Pro Phe Ser Leu Ala Thr Leu Gln Val Thr Leu Gly Leu Ala Asp Lys
225                 230                 235                 240 aat acc tct ctg gcc aga gtg att cag gcg ctc cat cag gag cta ccg      768
Asn Thr Ser Leu Ala Arg Val Ile Gln Ala Leu His Gln Glu Leu Pro
                245                 250                 255 gat ttt tgt acg gaa gta cac ccc ggc ggt gcc aac agt gta tta ctg      816
Asp Phe Cys Thr Glu Val His Pro Gly Gly Ala Asn Ser Val Leu Leu
            260                 265                 270 gcg gcg act cag ttg agc cgg ggg caa atg gaa ctg ctc acc gaa aag      864
Ala Ala Thr Gln Leu Ser Arg Gly Gln Met Glu Leu Leu Thr Glu Lys
        275                 280                 285 gca cct ttt cct gct acc agc ctg aca cag ccc gaa ctt gtt gcc cag      912
Ala Pro Phe Pro Ala Thr Ser Leu Thr Gln Pro Glu Leu Val Ala Gln
    290                 295                 300 tac cga agt ggc agc acc act gaa act ttg acc gat att gat ctt tcc      960
Tyr Arg Ser Gly Ser Thr Thr Glu Thr Leu Thr Asp Ile Asp Leu Ser
305                 310                 315                 320 aaa cag ggt tat att gtt cct cag ccg cag aaa gca cag gga ccc gac     1008
Lys Gln Gly Tyr Ile Val Pro Gln Pro Gln Lys Ala Gln Gly Pro Asp
                325                 330                 335 tca ctg acc tca acg ccg tta cct gca tca cgg gaa cct tac gat gaa     1056
Ser Leu Thr Ser Thr Pro Leu Pro Ala Ser Arg Glu Pro Tyr Asp Glu
            340                 345                 350 att cag gtt gaa tgt caa aat aaa gag ggg aaa tca gcg act atc acc     1104
Ile Gln Val Glu Cys Gln Asn Lys Glu Gly Lys Ser Ala Thr Ile Thr
        355                 360                 365 ctg cgg ggg cag tct gtt ctt atc tgc caa cgc gct aaa cgt cgg tta     1152
Leu Arg Gly Gln Ser Val Leu Ile Cys Gln Arg Ala Lys Arg Arg Leu
    370                 375                 380 aaa ccg ttc agt gac cgc ccg ccc tat cct cgt cag ctc caa ctg agc     1200
Lys Pro Phe Ser Asp Arg Pro Pro Tyr Pro Arg Gln Leu Gln Leu Ser
385                 390                 395                 400 tgg cat gac gaa gac aac aaa gat gtc gat ctc tct ctc ggc ccg tgg     1248
Trp His Asp Glu Asp Asn Lys Asp Val Asp Leu Ser Leu Gly Pro Trp
                405                 410                 415 ttc ggt gat ctg act gtt cag gca caa caa tgg gat gac aaa caa tct     1296
Phe Gly Asp Leu Thr Val Gln Ala Gln Gln Trp Asp Asp Lys Gln Ser
            420                 425                 430 ttt ctg acc ctg aaa tat cat ctg gtg tta tct aac caa gca tta cct     1344
Phe Leu Thr Leu Lys Tyr His Leu Val Leu Ser Asn Gln Ala Leu Pro
        435                 440                 445 gct gaa caa ctt tac cct caa gca gaa gat ttt ttc aga aag aac tat     1392
Ala Glu Gln Leu Tyr Pro Gln Ala Glu Asp Phe Phe Arg Lys Asn Tyr
    450                 455                 460
```

```
gga ttg gag ctc agt gag cgt gac aga ctg ccg gaa att ctg ttt ctt      1440
Gly Leu Glu Leu Ser Glu Arg Asp Arg Leu Pro Glu Ile Leu Phe Leu
465                 470                 475                 480 att gac cgg atc aaa gga cag gcc gaa gag atc gag cag gct att gcc      1488
Ile Asp Arg Ile Lys Gly Gln Ala Glu Glu Ile Glu Gln Ala Ile Ala
                485                 490                 495 tgg ggc gat ttt agt ccg gtc gtt tcc gca aat atc cgc ttt act aac      1536
Trp Gly Asp Phe Ser Pro Val Val Ser Ala Asn Ile Arg Phe Thr Asn
            500                 505                 510 ccg ata ttt tcc aat caa caa agc gaa tta cgt ttc ccg ctt cct ttt      1584
Pro Ile Phe Ser Asn Gln Gln Ser Glu Leu Arg Phe Pro Leu Pro Phe
        515                 520                 525 cag gtt ggt gcc tgt tac ctc aat gtc ggt cag cct gaa gcc gtt ggt      1632
Gln Val Gly Ala Cys Tyr Leu Asn Val Gly Gln Pro Glu Ala Val Gly
    530                 535                 540 att gat gta cag cgc cct cgc agt ctg acg gca acc aca aat cag cgt      1680
Ile Asp Val Gln Arg Pro Arg Ser Leu Thr Ala Thr Thr Asn Gln Arg
545                 550                 555                 560 ttc gat cgc ctg caa cgg ctc att cgc tta caa cgc tgg tta gca ata      1728
Phe Asp Arg Leu Gln Arg Leu Ile Arg Leu Gln Arg Trp Leu Ala Ile
                565                 570                 575 ccg cac cat gat ctg gat tgg tta tta acc tgc gca atg cgg gca gaa      1776
Pro His His Asp Leu Asp Trp Leu Leu Thr Cys Ala Met Arg Ala Glu
            580                 585                 590 ggt gaa aaa aat cta aca ctg gag ata aat ttt aat acg ttg cgg gca      1824
Gly Glu Lys Asn Leu Thr Leu Glu Ile Asn Phe Asn Thr Leu Arg Ala
        595                 600                 605 ttg ggt tta ttc cgt cat ctc aac cat cgt tat aaa ttg tca gct cct      1872
Leu Gly Leu Phe Arg His Leu Asn His Arg Tyr Lys Leu Ser Ala Pro
    610                 615                 620 gct ttc gca acg gta tta cat aca ctc tca cct ttt gct gtc agc gga      1920
Ala Phe Ala Thr Val Leu His Thr Leu Ser Pro Phe Ala Val Ser Gly
625                 630                 635                 640 aat ccc gcg ttt ttg gat cag gta ttc aat caa ccc aaa ctg ttt gat      1968
Asn Pro Ala Phe Leu Asp Gln Val Phe Asn Gln Pro Lys Leu Phe Asp
                645                 650                 655 gaa cct ttc ttt gtt gat aat cgt act ttt gat tac aac gcc att cgt      2016
Glu Pro Phe Phe Val Asp Asn Arg Thr Phe Asp Tyr Asn Ala Ile Arg
            660                 665                 670 ggt aat gat gca cga aca att aag caa ctg tgc gcc gga ttg aaa atc      2064
Gly Asn Asp Ala Arg Thr Ile Lys Gln Leu Cys Ala Gly Leu Lys Ile
        675                 680                 685 acc gta gcc acc ttc caa ttg tta gct gag cag gta aac acc gcc ttt      2112
Thr Val Ala Thr Phe Gln Leu Leu Ala Glu Gln Val Asn Thr Ala Phe
    690                 695                 700 cat ctg cca tcc ggc aaa tta acc tgt tca ctg cct gtt att tca gcg      2160
His Leu Pro Ser Gly Lys Leu Thr Cys Ser Leu Pro Val Ile Ser Ala
705                 710                 715                 720 ctt tat cgt ctg gtg act gtt cct cgg tta ttt aat tta acc gct gaa      2208
Leu Tyr Arg Leu Val Thr Val Pro Arg Leu Phe Asn Leu Thr Ala Glu
                725                 730                 735 cag ggc atg atg ctg att aac gca tta aat gcc agc gag aaa ttc tca      2256
Gln Gly Met Met Leu Ile Asn Ala Leu Asn Ala Ser Glu Lys Phe Ser
            740                 745                 750 cct cat att ctg gct ggt gag cct cga tta agc ctg tta aca aca gag      2304
Pro His Ile Leu Ala Gly Glu Pro Arg Leu Ser Leu Leu Thr Thr Glu
        755                 760                 765 ggt tca gat acc aca gag gtc gat tta ttg gat gtt att ctg atg ttg      2352
Gly Ser Asp Thr Thr Glu Val Asp Leu Leu Asp Val Ile Leu Met Leu
    770                 775                 780
```

| | | |
|---|---|---|
| gaa gaa gtt gct gtc tgg ctg caa cag agc aaa ctg aaa ccg gaa gaa<br>Glu Glu Val Ala Val Trp Leu Gln Gln Ser Lys Leu Lys Pro Glu Glu<br>785 790 795 800 | | 2400 |
| ttc tgc ctg atg ctg caa agt gtt atg ttg ccg gtt gtt gcc acg gac<br>Phe Cys Leu Met Leu Gln Ser Val Met Leu Pro Val Val Ala Thr Asp<br>805 810 815 | | 2448 |
| agc agt gtg aca ttc ttc gac aac ctg ctg caa ggc att ccc aaa acc<br>Ser Ser Val Thr Phe Phe Asp Asn Leu Leu Gln Gly Ile Pro Lys Thr<br>820 825 830 | | 2496 |
| tta ctc aca gaa gat aac ttc aac gca ggg gat atc ccc aga ctc cct<br>Leu Leu Thr Glu Asp Asn Phe Asn Ala Gly Asp Ile Pro Arg Leu Pro<br>835 840 845 | | 2544 |
| gaa gga gaa acc tgg ttt gac aaa ctt tcg atg ctg ata acc agc gat<br>Glu Gly Glu Thr Trp Phe Asp Lys Leu Ser Met Leu Ile Thr Ser Asp<br>850 855 860 | | 2592 |
| gga ctc gtc aac gtt tac cct ctc agt tgg ggc cag agt gat gaa gat<br>Gly Leu Val Asn Val Tyr Pro Leu Ser Trp Gly Gln Ser Asp Glu Asp<br>865 870 875 880 | | 2640 |
| tat ctg aaa tca gta ttg aca cct gtc gtc gaa aaa atc att agc gat<br>Tyr Leu Lys Ser Val Leu Thr Pro Val Val Glu Lys Ile Ile Ser Asp<br>885 890 895 | | 2688 |
| cca aac agt gtg att atc act gtt tcc gca tta aca cag gtc att act<br>Pro Asn Ser Val Ile Ile Thr Val Ser Ala Leu Thr Gln Val Ile Thr<br>900 905 910 | | 2736 |
| cag gcg aaa act gcg cag gaa gat ctg gtt tcc gcc agc gtg aca cgg<br>Gln Ala Lys Thr Ala Gln Glu Asp Leu Val Ser Ala Ser Val Thr Arg<br>915 920 925 | | 2784 |
| gaa tac ggt act gga cgt gat atc gtt cct tgg tta tta cgc tgg att<br>Glu Tyr Gly Thr Gly Arg Asp Ile Val Pro Trp Leu Leu Arg Trp Ile<br>930 935 940 | | 2832 |
| ggc agc agt gtt ccc gat ttc ctt ggc aaa att tat ata caa ggc gca<br>Gly Ser Ser Val Pro Asp Phe Leu Gly Lys Ile Tyr Ile Gln Gly Ala<br>945 950 955 960 | | 2880 |
| acc aga ggc gga cac ttg cgc act ccg ccg gat atc agc gct gaa tta<br>Thr Arg Gly Gly His Leu Arg Thr Pro Pro Asp Ile Ser Ala Glu Leu<br>965 970 975 | | 2928 |
| ctg cat atc acc tat cat ctg gcg atg aat aac atg ctg att aag cag<br>Leu His Ile Thr Tyr His Leu Ala Met Asn Asn Met Leu Ile Lys Gln<br>980 985 990 | | 2976 |
| tta cga ctc aaa gct caa atc att tca tta cgt atc atc atg cct gaa<br>Leu Arg Leu Lys Ala Gln Ile Ile Ser Leu Arg Ile Ile Met Pro Glu<br>995 1000 1005 | | 3024 |
| tgg ctc gga tta cca acg ata gat ggc agt ccg cta tcc gtg cat<br>Trp Leu Gly Leu Pro Thr Ile Asp Gly Ser Pro Leu Ser Val His<br>1010 1015 1020 | | 3069 |
| gaa att tgg gca ctg agc cgg ttc cgt aac tgg gcg acc agc tca<br>Glu Ile Trp Ala Leu Ser Arg Phe Arg Asn Trp Ala Thr Ser Ser<br>1025 1030 1035 | | 3114 |
| ttg ttc agt gaa gac gag tta atc gag tat ttt gct ttt gcc aat<br>Leu Phe Ser Glu Asp Glu Leu Ile Glu Tyr Phe Ala Phe Ala Asn<br>1040 1045 1050 | | 3159 |
| cag ccg gag cag gac gtt cgt aac gat gaa gat ttt aat cgg gac<br>Gln Pro Glu Gln Asp Val Arg Asn Asp Glu Asp Phe Asn Arg Asp<br>1055 1060 1065 | | 3204 |
| tgt gct gaa aag ctt gcc gac ata ctg gaa tgg gat gcc gat gaa<br>Cys Ala Glu Lys Leu Ala Asp Ile Leu Glu Trp Asp Ala Asp Glu<br>1070 1075 1080 | | 3249 |
| att gag ctg gca acc cga cat ttt gat cct gcc cca gca cgt gcc<br>Ile Glu Leu Ala Thr Arg His Phe Asp Pro Ala Pro Ala Arg Ala | | 3294 |

-continued

```
       1085                1090                1095
aga aat atg gga caa att gac tgg ctg cgt cgt gtc atg gcg ttg    3339
Arg Asn Met Gly Gln Ile Asp Trp Leu Arg Arg Val Met Ala Leu
    1100                1105                1110 tcg cgt cag act ggc ctg tca gtg aca ccg tta atg aca gcc gca    3384
Ser Arg Gln Thr Gly Leu Ser Val Thr Pro Leu Met Thr Ala Ala
    1115                1120                1125 acg tta ccg cct ttc ccg ccc tat gac cag ata acc cat gtc ggt    3429
Thr Leu Pro Pro Phe Pro Pro Tyr Asp Gln Ile Thr His Val Gly
    1130                1135                1140 gaa gcg gtg att gcg gca acc cag tac cca tca gag gag taa        3471
Glu Ala Val Ile Ala Ala Thr Gln Tyr Pro Ser Glu Glu
    1145                1150                1155

<210> SEQ ID NO 4
<211> LENGTH: 1156
<212> TYPE: PRT
<213> ORGANISM: Xenorhabdus nematophilus str. Xwi

<400> SEQUENCE: 4

Met His Thr Thr Ser Thr Asp Glu Lys Thr Ile Thr Pro Leu Leu Ala
1               5                   10                  15

Ser Ala Phe Met Gln Ala Gln His Ser Ala Gln Arg Leu Gln Ser Met
            20                  25                  30

Glu Gln Ser His Asn Glu Leu Ser Arg Trp Gly Tyr Phe Ser Val Phe
        35                  40                  45

Asp Ile Val Lys Val Gly Pro Ser Arg Phe Arg Arg His Arg His
    50                  55                  60

His Phe Asn Gly Gln Ala Glu Thr Leu Tyr Gln Asn Ala Leu Ser Tyr
65                  70                  75                  80

Ala Thr Gln Leu Ile His Ser Ala Arg Glu Arg Gly Leu Arg Asp Ala
                85                  90                  95

Glu Thr Leu Arg Met Ala Arg Val Ala Ser Gly Gln Pro Glu Leu Pro
            100                 105                 110

Asn Tyr Ala Asp Leu Phe Pro Glu Pro Trp Asp Asn Phe Cys Lys Pro
        115                 120                 125

Gly Ala Leu Glu Ala Leu Asn Ser Pro Ala Ala Tyr Leu Leu Glu Leu
    130                 135                 140

Tyr Gln Phe Ala Arg Gln Leu Glu Leu Asp Ala Thr Glu Gly Ala Ile
145                 150                 155                 160

Gly Phe Ala Gln Arg Arg Pro Asp Ile Pro Glu Leu Leu Leu Asp Arg
                165                 170                 175

Asp Asn Thr Asn Gln Glu Leu Pro Ala Leu Gln Ile Val Asn Glu Ile
            180                 185                 190

Leu Ser Phe Ile Ala Ala Asp Tyr Ile Asp His Ser Gln Glu Thr Gly
        195                 200                 205

Lys Pro Val Asn Gln Val Leu Gly Glu Thr Tyr Tyr Pro Tyr Thr Leu
    210                 215                 220

Pro Phe Ser Leu Ala Thr Leu Gln Val Thr Leu Gly Leu Ala Asp Lys
225                 230                 235                 240

Asn Thr Ser Leu Ala Arg Val Ile Gln Ala Leu His Gln Glu Leu Pro
                245                 250                 255

Asp Phe Cys Thr Glu Val His Pro Gly Gly Ala Asn Ser Val Leu Leu
            260                 265                 270

Ala Ala Thr Gln Leu Ser Arg Gly Gln Met Glu Leu Leu Thr Glu Lys
        275                 280                 285
```

-continued

```
Ala Pro Phe Pro Ala Thr Ser Leu Thr Gln Pro Glu Leu Val Ala Gln
            290                 295                 300

Tyr Arg Ser Gly Ser Thr Thr Glu Thr Leu Thr Asp Ile Asp Leu Ser
305                 310                 315                 320

Lys Gln Gly Tyr Ile Val Pro Gln Pro Gln Lys Ala Gln Gly Pro Asp
                    325                 330                 335

Ser Leu Thr Ser Thr Pro Leu Pro Ala Ser Arg Glu Pro Tyr Asp Glu
            340                 345                 350

Ile Gln Val Glu Cys Gln Asn Lys Glu Gly Lys Ser Ala Thr Ile Thr
            355                 360                 365

Leu Arg Gly Gln Ser Val Leu Ile Cys Gln Arg Ala Lys Arg Leu
    370                 375                 380

Lys Pro Phe Ser Asp Arg Pro Pro Tyr Pro Arg Gln Leu Gln Leu Ser
385                 390                 395                 400

Trp His Asp Glu Asp Asn Lys Asp Val Asp Leu Ser Leu Gly Pro Trp
                    405                 410                 415

Phe Gly Asp Leu Thr Val Gln Ala Gln Gln Trp Asp Asp Lys Gln Ser
            420                 425                 430

Phe Leu Thr Leu Lys Tyr His Leu Val Leu Ser Asn Gln Ala Leu Pro
            435                 440                 445

Ala Glu Gln Leu Tyr Pro Gln Ala Glu Asp Phe Arg Lys Asn Tyr
    450                 455                 460

Gly Leu Glu Leu Ser Glu Arg Asp Arg Leu Pro Glu Ile Leu Phe Leu
465                 470                 475                 480

Ile Asp Arg Ile Lys Gly Gln Ala Glu Glu Ile Glu Gln Ala Ile Ala
                    485                 490                 495

Trp Gly Asp Phe Ser Pro Val Val Ser Ala Asn Ile Arg Phe Thr Asn
            500                 505                 510

Pro Ile Phe Ser Asn Gln Gln Ser Glu Leu Arg Phe Pro Leu Pro Phe
            515                 520                 525

Gln Val Gly Ala Cys Tyr Leu Asn Val Gly Gln Pro Glu Ala Val Gly
    530                 535                 540

Ile Asp Val Gln Arg Pro Arg Ser Leu Thr Ala Thr Thr Asn Gln Arg
545                 550                 555                 560

Phe Asp Arg Leu Gln Arg Leu Ile Arg Leu Gln Arg Trp Leu Ala Ile
                    565                 570                 575

Pro His His Asp Leu Asp Trp Leu Leu Thr Cys Ala Met Arg Ala Glu
            580                 585                 590

Gly Glu Lys Asn Leu Thr Leu Glu Ile Asn Phe Asn Thr Leu Arg Ala
            595                 600                 605

Leu Gly Leu Phe Arg His Leu Asn His Arg Tyr Lys Leu Ser Ala Pro
    610                 615                 620

Ala Phe Ala Thr Val Leu His Thr Leu Ser Pro Phe Ala Val Ser Gly
625                 630                 635                 640

Asn Pro Ala Phe Leu Asp Gln Val Phe Asn Gln Pro Lys Leu Phe Asp
                    645                 650                 655

Glu Pro Phe Phe Val Asp Asn Arg Thr Phe Asp Tyr Asn Ala Ile Arg
            660                 665                 670

Gly Asn Asp Ala Arg Thr Ile Lys Gln Leu Cys Ala Gly Leu Lys Ile
            675                 680                 685

Thr Val Ala Thr Phe Gln Leu Leu Ala Glu Gln Val Asn Thr Ala Phe
    690                 695                 700
```

```
His Leu Pro Ser Gly Lys Leu Thr Cys Ser Leu Pro Val Ile Ser Ala
705                 710                 715                 720

Leu Tyr Arg Leu Val Thr Val Pro Arg Leu Phe Asn Leu Thr Ala Glu
            725                 730                 735

Gln Gly Met Met Leu Ile Asn Ala Leu Asn Ala Ser Glu Lys Phe Ser
        740                 745                 750

Pro His Ile Leu Ala Gly Glu Pro Arg Leu Ser Leu Leu Thr Thr Glu
    755                 760                 765

Gly Ser Asp Thr Thr Glu Val Asp Leu Leu Asp Val Ile Leu Met Leu
770                 775                 780

Glu Glu Val Ala Val Trp Leu Gln Gln Ser Lys Leu Lys Pro Glu Glu
785                 790                 795                 800

Phe Cys Leu Met Leu Gln Ser Val Met Leu Pro Val Val Ala Thr Asp
                805                 810                 815

Ser Ser Val Thr Phe Phe Asp Asn Leu Leu Gln Gly Ile Pro Lys Thr
            820                 825                 830

Leu Leu Thr Glu Asp Asn Phe Asn Ala Gly Asp Ile Pro Arg Leu Pro
        835                 840                 845

Glu Gly Glu Thr Trp Phe Asp Lys Leu Ser Met Leu Ile Thr Ser Asp
    850                 855                 860

Gly Leu Val Asn Val Tyr Pro Leu Ser Trp Gly Gln Ser Asp Glu Asp
865                 870                 875                 880

Tyr Leu Lys Ser Val Leu Thr Pro Val Val Glu Lys Ile Ile Ser Asp
                885                 890                 895

Pro Asn Ser Val Ile Ile Thr Val Ser Ala Leu Thr Gln Val Ile Thr
            900                 905                 910

Gln Ala Lys Thr Ala Gln Glu Asp Leu Val Ser Ala Ser Val Thr Arg
        915                 920                 925

Glu Tyr Gly Thr Gly Arg Asp Ile Val Pro Trp Leu Leu Arg Trp Ile
    930                 935                 940

Gly Ser Ser Val Pro Asp Phe Leu Gly Lys Ile Tyr Ile Gln Gly Ala
945                 950                 955                 960

Thr Arg Gly Gly His Leu Arg Thr Pro Pro Asp Ile Ser Ala Glu Leu
                965                 970                 975

Leu His Ile Thr Tyr His Leu Ala Met Asn Asn Met Leu Ile Lys Gln
            980                 985                 990

Leu Arg Leu Lys Ala Gln Ile Ile Ser Leu Arg Ile Ile Met Pro Glu
        995                 1000                1005

Trp Leu Gly Leu Pro Thr Ile Asp Gly Ser Pro Leu Ser Val His
    1010                1015                1020

Glu Ile Trp Ala Leu Ser Arg Phe Arg Asn Trp Ala Thr Ser Ser
    1025                1030                1035

Leu Phe Ser Glu Asp Glu Leu Ile Glu Tyr Phe Ala Phe Ala Asn
    1040                1045                1050

Gln Pro Glu Gln Asp Val Arg Asn Asp Glu Asp Phe Asn Arg Asp
    1055                1060                1065

Cys Ala Glu Lys Leu Ala Asp Ile Leu Glu Trp Asp Ala Asp Glu
    1070                1075                1080

Ile Glu Leu Ala Thr Arg His Phe Asp Pro Ala Pro Ala Arg Ala
    1085                1090                1095

Arg Asn Met Gly Gln Ile Asp Trp Leu Arg Arg Val Met Ala Leu
    1100                1105                1110

Ser Arg Gln Thr Gly Leu Ser Val Thr Pro Leu Met Thr Ala Ala
```

| | | |
|---|---|---|
| Thr Leu Pro Pro Phe Pro Pro Tyr Asp Gln Ile Thr His Val Gly | | |
| 1130 1135 1140 | | |

Glu Ala Val Ile Ala Ala Thr Gln Tyr Pro Ser Glu Glu
  1145            1150            1155

<210> SEQ ID NO 5
<211> LENGTH: 1947
<212> TYPE: DNA
<213> ORGANISM: Xenorhabdus nematophilus str. Xwi
<220> FEATURE:
<221> NAME/KEY: CDS
<222> LOCATION: (1)..(1944)

<400> SEQUENCE: 5

| | |
|---|---|
| atg tct caa aat gtt tat cga tac cct tca att aaa gcg atg tct gac<br>Met Ser Gln Asn Val Tyr Arg Tyr Pro Ser Ile Lys Ala Met Ser Asp<br>1               5                10               15 | 48 |
| gcc agc agc gaa gta ggc gca tct ctg gtt gcc tgg cag aat caa tct<br>Ala Ser Ser Glu Val Gly Ala Ser Leu Val Ala Trp Gln Asn Gln Ser<br>          20                25                30 | 96 |
| ggt ggt caa acc tgg tat gtc att tat gat agc gcg gtt ttt aaa aac<br>Gly Gly Gln Thr Trp Tyr Val Ile Tyr Asp Ser Ala Val Phe Lys Asn<br>        35                40                45 | 144 |
| atc ggc tgg gtt gaa cgc tgg cat att ccc gac cgc aat att tca cct<br>Ile Gly Trp Val Glu Arg Trp His Ile Pro Asp Arg Asn Ile Ser Pro<br>50              55                60 | 192 |
| gat tta ccg gtt tat gag aat gcc tgg caa tat gtc cgt gag gcg aca<br>Asp Leu Pro Val Tyr Glu Asn Ala Trp Gln Tyr Val Arg Glu Ala Thr<br>65              70                75               80 | 240 |
| ccg gaa gaa att gcc gat cac ggt aac ccc aat acg cct gat gta ccg<br>Pro Glu Glu Ile Ala Asp His Gly Asn Pro Asn Thr Pro Asp Val Pro<br>               85                90               95 | 288 |
| ccg gga gaa aaa acc gag gta ttg caa tat gat gca ctc aca gaa gaa<br>Pro Gly Glu Lys Thr Glu Val Leu Gln Tyr Asp Ala Leu Thr Glu Glu<br>         100              105             110 | 336 |
| acc tat cag aag gtg gga tat aaa cct gac ggc agc gga act cct ttg<br>Thr Tyr Gln Lys Val Gly Tyr Lys Pro Asp Gly Ser Gly Thr Pro Leu<br>       115              120             125 | 384 |
| agt tat tct tca gca cgt gtt gcc aag tcc ctg tac aac gaa tat gaa<br>Ser Tyr Ser Ser Ala Arg Val Ala Lys Ser Leu Tyr Asn Glu Tyr Glu<br>      130             135             140 | 432 |
| gtt gat ccg gaa aat aca gaa ccg ctg cct aaa gtc tct gcc tat att<br>Val Asp Pro Glu Asn Thr Glu Pro Leu Pro Lys Val Ser Ala Tyr Ile<br>145             150               155              160 | 480 |
| act gac tgg tgc cag tat gat gcg cgt ttg tcg cca gaa acc cag gat<br>Thr Asp Trp Cys Gln Tyr Asp Ala Arg Leu Ser Pro Glu Thr Gln Asp<br>                165             170             175 | 528 |
| aac act gcg ctg acc agc gac gat gcc ccc ggc cgt ggt ttt gat ctg<br>Asn Thr Ala Leu Thr Ser Asp Asp Ala Pro Gly Arg Gly Phe Asp Leu<br>          180             185             190 | 576 |
| gaa aaa atc ccg cct acc gcc tac gac cgc ctg att ttc agt ttt atg<br>Glu Lys Ile Pro Pro Thr Ala Tyr Asp Arg Leu Ile Phe Ser Phe Met<br>       195              200             205 | 624 |
| gcc gtc aac ggt gat aaa ggc aag tta tcc gaa cgg att aat gag gtt<br>Ala Val Asn Gly Asp Lys Gly Lys Leu Ser Glu Arg Ile Asn Glu Val<br>      210             215             220 | 672 |
| gtt gac ggg tgg aac cgg caa gca gaa gcc agc agt ggc cag att gcc<br>Val Asp Gly Trp Asn Arg Gln Ala Glu Ala Ser Ser Gly Gln Ile Ala<br>225             230              235              240 | 720 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cct | att | aca | tta | ggc | cat | att | gta | ccc | gtt | gat | cct | tat | ggt | gat | tta | 768  |
| Pro | Ile | Thr | Leu | Gly | His | Ile | Val | Pro | Val | Asp | Pro | Tyr | Gly | Asp | Leu |      |
|     |     |     |     | 245 |     |     |     | 250 |     |     |     |     | 255 |     |     |      |
| ggc | acc | aca | cgc | aat | gtc | ggt | ctg | gac | gcg | gat | cag | cgc | cgt | gat | gcc | 816  |
| Gly | Thr | Thr | Arg | Asn | Val | Gly | Leu | Asp | Ala | Asp | Gln | Arg | Arg | Asp | Ala |      |
|     | 260 |     |     |     |     | 265 |     |     |     |     | 270 |     |     |     |     |      |
| agc | ccg | aag | aat | ttc | ttg | caa | tat | tac | aat | cag | gat | gca | gcc | tcc | ggt | 864  |
| Ser | Pro | Lys | Asn | Phe | Leu | Gln | Tyr | Tyr | Asn | Gln | Asp | Ala | Ala | Ser | Gly |      |
|     | 275 |     |     |     |     | 280 |     |     |     |     | 285 |     |     |     |     |      |
| tta | ctg | ggg | gga | ttg | cgt | aat | ctg | aaa | gcg | cga | gca | aaa | cag | gca | ggg | 912  |
| Leu | Leu | Gly | Gly | Leu | Arg | Asn | Leu | Lys | Ala | Arg | Ala | Lys | Gln | Ala | Gly |      |
|     | 290 |     |     |     |     | 295 |     |     |     |     | 300 |     |     |     |     |      |
| cac | aag | ctg | gaa | ctc | gca | ttc | agt | atc | ggc | ggc | tgg | agt | atg | tca | ggg | 960  |
| His | Lys | Leu | Glu | Leu | Ala | Phe | Ser | Ile | Gly | Gly | Trp | Ser | Met | Ser | Gly |      |
| 305 |     |     |     |     | 310 |     |     |     |     | 315 |     |     |     |     | 320 |      |
| tat | ttc | tct | gtg | atg | gcc | aaa | gat | cct | gag | caa | cgt | gct | aca | ttt | gtg | 1008 |
| Tyr | Phe | Ser | Val | Met | Ala | Lys | Asp | Pro | Glu | Gln | Arg | Ala | Thr | Phe | Val |      |
|     |     |     |     | 325 |     |     |     |     | 330 |     |     |     |     | 335 |     |      |
| agt | agc | atc | gtc | gac | ttc | ttc | cgg | cgt | ttt | ccc | atg | ttt | act | gcg | gtg | 1056 |
| Ser | Ser | Ile | Val | Asp | Phe | Phe | Arg | Arg | Phe | Pro | Met | Phe | Thr | Ala | Val |      |
|     |     |     | 340 |     |     |     |     | 345 |     |     |     |     | 350 |     |     |      |
| gat | atc | gac | tgg | gaa | tac | ccc | ggc | gcc | aca | ggt | gaa | gaa | ggt | aat | gaa | 1104 |
| Asp | Ile | Asp | Trp | Glu | Tyr | Pro | Gly | Ala | Thr | Gly | Glu | Glu | Gly | Asn | Glu |      |
|     |     | 355 |     |     |     |     | 360 |     |     |     |     | 365 |     |     |     |      |
| ttc | gac | ccg | gaa | cat | gat | ggc | cca | aac | tat | gtt | ttg | tta | gtg | aaa | gag | 1152 |
| Phe | Asp | Pro | Glu | His | Asp | Gly | Pro | Asn | Tyr | Val | Leu | Leu | Val | Lys | Glu |      |
|     | 370 |     |     |     |     | 375 |     |     |     |     | 380 |     |     |     |     |      |
| ctg | cgt | gaa | gca | ctg | aac | atc | gcc | ttt | gga | acc | cgg | gcc | cgt | aaa | gaa | 1200 |
| Leu | Arg | Glu | Ala | Leu | Asn | Ile | Ala | Phe | Gly | Thr | Arg | Ala | Arg | Lys | Glu |      |
| 385 |     |     |     |     | 390 |     |     |     |     | 395 |     |     |     |     | 400 |      |
| atc | acg | ata | gcc | tgt | agc | gcc | gtc | gtt | gcc | aaa | atg | gag | aag | tcc | agc | 1248 |
| Ile | Thr | Ile | Ala | Cys | Ser | Ala | Val | Val | Ala | Lys | Met | Glu | Lys | Ser | Ser |      |
|     |     |     |     | 405 |     |     |     |     | 410 |     |     |     |     | 415 |     |      |
| ttc | aaa | gaa | atc | gca | cct | tat | tta | gac | aat | atc | ttt | gtg | atg | acc | tac | 1296 |
| Phe | Lys | Glu | Ile | Ala | Pro | Tyr | Leu | Asp | Asn | Ile | Phe | Val | Met | Thr | Tyr |      |
|     |     |     | 420 |     |     |     |     | 425 |     |     |     |     | 430 |     |     |      |
| gac | ttc | ttt | ggt | acc | ggt | tgg | gca | gaa | tac | atc | ggt | cac | cat | act | aac | 1344 |
| Asp | Phe | Phe | Gly | Thr | Gly | Trp | Ala | Glu | Tyr | Ile | Gly | His | His | Thr | Asn |      |
|     |     | 435 |     |     |     |     | 440 |     |     |     |     | 445 |     |     |     |      |
| ctg | tat | ccc | cca | aga | tat | gaa | tat | gac | ggc | gat | aac | cct | cct | ccg | ccc | 1392 |
| Leu | Tyr | Pro | Pro | Arg | Tyr | Glu | Tyr | Asp | Gly | Asp | Asn | Pro | Pro | Pro | Pro |      |
|     | 450 |     |     |     |     | 455 |     |     |     |     | 460 |     |     |     |     |      |
| aat | cct | gat | cgg | gac | atg | gat | tac | tcg | gct | gat | gag | gcg | atc | cgc | ttt | 1440 |
| Asn | Pro | Asp | Arg | Asp | Met | Asp | Tyr | Ser | Ala | Asp | Glu | Ala | Ile | Arg | Phe |      |
| 465 |     |     |     |     | 470 |     |     |     |     | 475 |     |     |     |     | 480 |      |
| tta | ctg | tca | caa | ggt | gta | caa | ccg | gag | aaa | att | cac | ctc | gga | ttt | gct | 1488 |
| Leu | Leu | Ser | Gln | Gly | Val | Gln | Pro | Glu | Lys | Ile | His | Leu | Gly | Phe | Ala |      |
|     |     |     |     | 485 |     |     |     |     | 490 |     |     |     |     | 495 |     |      |
| aac | tat | gga | cgt | tca | tgt | ctg | ggt | gct | gat | ctg | aca | act | cgc | cgc | tat | 1536 |
| Asn | Tyr | Gly | Arg | Ser | Cys | Leu | Gly | Ala | Asp | Leu | Thr | Thr | Arg | Arg | Tyr |      |
|     |     |     | 500 |     |     |     |     | 505 |     |     |     |     | 510 |     |     |      |
| aac | aga | aca | gga | gag | cca | ctg | ggc | acg | atg | gaa | aaa | ggt | gct | ccg | gaa | 1584 |
| Asn | Arg | Thr | Gly | Glu | Pro | Leu | Gly | Thr | Met | Glu | Lys | Gly | Ala | Pro | Glu |      |
|     |     | 515 |     |     |     |     | 520 |     |     |     |     | 525 |     |     |     |      |
| ttc | ttc | tgt | ctg | ctg | aat | aac | caa | tac | gat | gcg | gaa | tat | gaa | att | gca | 1632 |
| Phe | Phe | Cys | Leu | Leu | Asn | Asn | Gln | Tyr | Asp | Ala | Glu | Tyr | Glu | Ile | Ala |      |
|     | 530 |     |     |     |     | 535 |     |     |     |     | 540 |     |     |     |     |      |
| cgc | ggg | aaa | aat | cag | ttt | gaa | ctg | gtg | aca | gac | acg | gaa | acc | gac | gct | 1680 |
| Arg | Gly | Lys | Asn | Gln | Phe | Glu | Leu | Val | Thr | Asp | Thr | Glu | Thr | Asp | Ala |      |
| 545 |     |     |     |     | 550 |     |     |     |     | 555 |     |     |     |     | 560 |      |

-continued

```
gac gca ctc ttt aat gct gac ggt ggt cac tgg att tca ctg gat acg    1728
Asp Ala Leu Phe Asn Ala Asp Gly Gly His Trp Ile Ser Leu Asp Thr
            565                 570                 575 ccc cgc act gtg ctg cat aag gga att tat gca acc aaa atg aaa ttg    1776
Pro Arg Thr Val Leu His Lys Gly Ile Tyr Ala Thr Lys Met Lys Leu
        580                 585                 590 ggc ggg atc ttc tct tgg tca ggc gat cag gat gat ggc ctg ttg gca    1824
Gly Gly Ile Phe Ser Trp Ser Gly Asp Gln Asp Asp Gly Leu Leu Ala
    595                 600                 605 aat gct gct cac gaa ggt ttg ggt tac tta cct gta cgc gga aaa gag    1872
Asn Ala Ala His Glu Gly Leu Gly Tyr Leu Pro Val Arg Gly Lys Glu
610                 615                 620 aag att gat atg gga ccg tta tat aac aaa gga cgt ctc att cag ctt    1920
Lys Ile Asp Met Gly Pro Leu Tyr Asn Lys Gly Arg Leu Ile Gln Leu
625                 630                 635                 640 cct aaa gta acc cgt cgt aaa tcg tag                                1947
Pro Lys Val Thr Arg Arg Lys Ser
            645

<210> SEQ ID NO 6
<211> LENGTH: 648
<212> TYPE: PRT
<213> ORGANISM: Xenorhabdus nematophilus str. Xwi

<400> SEQUENCE: 6

Met Ser Gln Asn Val Tyr Arg Tyr Pro Ser Ile Lys Ala Met Ser Asp
1               5                   10                  15

Ala Ser Ser Glu Val Gly Ala Ser Leu Val Ala Trp Gln Asn Gln Ser
            20                  25                  30

Gly Gly Gln Thr Trp Tyr Val Ile Tyr Asp Ser Ala Val Phe Lys Asn
        35                  40                  45

Ile Gly Trp Val Glu Arg Trp His Ile Pro Asp Arg Asn Ile Ser Pro
    50                  55                  60

Asp Leu Pro Val Tyr Glu Asn Ala Trp Gln Tyr Val Arg Glu Ala Thr
65                  70                  75                  80

Pro Glu Glu Ile Ala Asp His Gly Asn Pro Asn Thr Pro Asp Val Pro
                85                  90                  95

Pro Gly Glu Lys Thr Glu Val Leu Gln Tyr Asp Ala Leu Thr Glu Glu
            100                 105                 110

Thr Tyr Gln Lys Val Gly Tyr Lys Pro Asp Gly Ser Gly Thr Pro Leu
        115                 120                 125

Ser Tyr Ser Ser Ala Arg Val Ala Lys Ser Leu Tyr Asn Glu Tyr Glu
    130                 135                 140

Val Asp Pro Glu Asn Thr Glu Pro Leu Pro Lys Val Ser Ala Tyr Ile
145                 150                 155                 160

Thr Asp Trp Cys Gln Tyr Asp Ala Arg Leu Ser Pro Glu Thr Gln Asp
                165                 170                 175

Asn Thr Ala Leu Thr Ser Asp Ala Pro Gly Arg Gly Phe Asp Leu
            180                 185                 190

Glu Lys Ile Pro Pro Thr Ala Tyr Asp Arg Leu Ile Phe Ser Phe Met
        195                 200                 205

Ala Val Asn Gly Asp Lys Gly Lys Leu Ser Arg Ile Asn Glu Val
    210                 215                 220

Val Asp Gly Trp Asn Arg Gln Ala Glu Ala Ser Ser Gly Gln Ile Ala
225                 230                 235                 240

Pro Ile Thr Leu Gly His Ile Val Pro Val Asp Pro Tyr Gly Asp Leu
```

```
                245                 250                 255
Gly Thr Thr Arg Asn Val Gly Leu Asp Ala Asp Gln Arg Arg Asp Ala
            260                 265                 270
Ser Pro Lys Asn Phe Leu Gln Tyr Tyr Asn Gln Asp Ala Ala Ser Gly
        275                 280                 285
Leu Leu Gly Gly Leu Arg Asn Leu Lys Ala Arg Ala Lys Gln Ala Gly
        290                 295                 300
His Lys Leu Glu Leu Ala Phe Ser Ile Gly Gly Trp Ser Met Ser Gly
305                 310                 315                 320
Tyr Phe Ser Val Met Ala Lys Asp Pro Glu Gln Arg Ala Thr Phe Val
                325                 330                 335
Ser Ser Ile Val Asp Phe Phe Arg Arg Phe Pro Met Phe Thr Ala Val
                340                 345                 350
Asp Ile Asp Trp Glu Tyr Pro Gly Ala Thr Gly Glu Glu Gly Asn Glu
                355                 360                 365
Phe Asp Pro Glu His Asp Gly Pro Asn Tyr Val Leu Leu Val Lys Glu
            370                 375                 380
Leu Arg Glu Ala Leu Asn Ile Ala Phe Gly Thr Arg Ala Arg Lys Glu
385                 390                 395                 400
Ile Thr Ile Ala Cys Ser Ala Val Val Ala Lys Met Glu Lys Ser Ser
                405                 410                 415
Phe Lys Glu Ile Ala Pro Tyr Leu Asp Asn Ile Phe Val Met Thr Tyr
                420                 425                 430
Asp Phe Phe Gly Thr Gly Trp Ala Glu Tyr Ile Gly His His Thr Asn
            435                 440                 445
Leu Tyr Pro Pro Arg Tyr Glu Tyr Asp Gly Asp Asn Pro Pro Pro Pro
450                 455                 460
Asn Pro Asp Arg Asp Met Asp Tyr Ser Ala Asp Glu Ala Ile Arg Phe
465                 470                 475                 480
Leu Leu Ser Gln Gly Val Gln Pro Glu Lys Ile His Leu Gly Phe Ala
                485                 490                 495
Asn Tyr Gly Arg Ser Cys Leu Gly Ala Asp Leu Thr Thr Arg Arg Tyr
            500                 505                 510
Asn Arg Thr Gly Glu Pro Leu Gly Thr Met Glu Lys Gly Ala Pro Glu
        515                 520                 525
Phe Phe Cys Leu Leu Asn Asn Gln Tyr Asp Ala Glu Tyr Glu Ile Ala
        530                 535                 540
Arg Gly Lys Asn Gln Phe Glu Leu Val Thr Asp Thr Glu Thr Asp Ala
545                 550                 555                 560
Asp Ala Leu Phe Asn Ala Asp Gly Gly His Trp Ile Ser Leu Asp Thr
                565                 570                 575
Pro Arg Thr Val Leu His Lys Gly Ile Tyr Ala Thr Lys Met Lys Leu
            580                 585                 590
Gly Gly Ile Phe Ser Trp Ser Gly Asp Gln Asp Asp Gly Leu Leu Ala
            595                 600                 605
Asn Ala Ala His Glu Gly Leu Gly Tyr Leu Pro Val Arg Gly Lys Glu
        610                 615                 620
Lys Ile Asp Met Gly Pro Leu Tyr Asn Lys Gly Arg Leu Ile Gln Leu
625                 630                 635                 640
Pro Lys Val Thr Arg Arg Lys Ser
                645

<210> SEQ ID NO 7
```

<211> LENGTH: 1476
<212> TYPE: PRT
<213> ORGANISM: Photorhabdus luminescens

<400> SEQUENCE: 7

```
Met Gln Asn Ser Gln Thr Phe Ser Val Thr Glu Leu Ser Leu Pro Lys
1               5                   10                  15

Gly Gly Gly Ala Ile Thr Gly Met Gly Glu Ala Leu Thr Pro Ala Gly
            20                  25                  30

Pro Asp Gly Met Ala Ala Leu Ser Leu Pro Leu Pro Ile Ser Ala Gly
        35                  40                  45

Arg Gly Tyr Ala Pro Ser Leu Thr Leu Asn Tyr Asn Ser Gly Thr Gly
    50                  55                  60

Asn Ser Pro Phe Gly Leu Gly Trp Asp Cys Gly Val Met Ala Ile Arg
65                  70                  75                  80

Arg Arg Thr Ser Thr Gly Val Pro Asn Tyr Asp Glu Thr Asp Thr Phe
                85                  90                  95

Leu Gly Pro Glu Gly Glu Val Leu Val Ala Leu Asn Glu Ala Gly
            100                 105                 110

Gln Ala Asp Ile Arg Ser Glu Ser Ser Leu Gln Gly Ile Asn Leu Gly
        115                 120                 125

Ala Thr Phe Thr Val Thr Cys Tyr Arg Ser Arg Leu Glu Ser His Phe
    130                 135                 140

Asn Arg Leu Glu Tyr Trp Gln Pro Gln Thr Thr Gly Ala Thr Asp Phe
145                 150                 155                 160

Trp Leu Ile Tyr Ser Pro Asp Gly Gln Val His Leu Leu Gly Lys Asn
                165                 170                 175

Pro Gln Ala Arg Ile Ser Asn Pro Leu Asn Val Asn Gln Thr Ala Gln
            180                 185                 190

Trp Leu Leu Glu Ala Ser Ile Ser Ser His Ser Glu Gln Ile Tyr Tyr
        195                 200                 205

Gln Tyr Arg Ala Glu Asp Glu Ala Gly Cys Glu Thr Asp Glu Leu Ala
    210                 215                 220

Ala His Pro Ser Ala Thr Val Gln Arg Tyr Leu Gln Thr Val His Tyr
225                 230                 235                 240

Gly Asn Leu Thr Ala Ser Asp Val Phe Pro Thr Leu Asn Gly Asp Asp
                245                 250                 255

Pro Leu Lys Ser Gly Trp Met Phe Cys Leu Val Phe Asp Tyr Gly Glu
            260                 265                 270

Arg Lys Asn Ser Leu Ser Glu Met Pro Leu Phe Lys Ala Thr Gly Asn
        275                 280                 285

Trp Leu Cys Arg Lys Asp Arg Phe Ser Arg Tyr Glu Tyr Gly Phe Glu
    290                 295                 300

Leu Arg Thr Arg Arg Leu Cys Arg Gln Ile Leu Met Phe His Arg Leu
305                 310                 315                 320

Gln Thr Leu Ser Gly Gln Ala Lys Gly Asp Asp Glu Pro Ala Leu Val
                325                 330                 335

Ser Arg Leu Ile Leu Asp Tyr Asp Glu Asn Ala Met Val Ser Thr Leu
            340                 345                 350

Val Ser Val Arg Arg Val Gly His Glu Asp Asn Thr Val Thr Ala
        355                 360                 365

Leu Pro Pro Leu Glu Leu Ala Tyr Gln Pro Phe Glu Pro Glu Gln Thr
    370                 375                 380

Ala Leu Trp Gln Ser Met Asp Val Leu Ala Asn Phe Asn Thr Ile Gln
```

-continued

```
            385                 390                 395                 400
Arg Trp Gln Leu Leu Asp Leu Lys Gly Glu Gly Val Pro Gly Ile Leu
                405                 410                 415
Tyr Gln Asp Arg Asn Gly Trp Trp Tyr Arg Ser Ala Gln Arg Gln Ala
            420                 425                 430
Gly Glu Glu Met Asn Ala Val Thr Trp Gly Lys Met Gln Leu Leu Pro
                435                 440                 445
Ile Thr Pro Ala Val Gln Asp Asn Ala Ser Leu Met Asp Ile Asn Gly
        450                 455                 460
Asp Gly Gln Leu Asp Trp Val Ile Thr Gly Pro Gly Leu Arg Gly Tyr
465                 470                 475                 480
His Ser Gln His Pro Asp Gly Ser Trp Thr Arg Phe Thr Pro Leu His
                485                 490                 495
Ala Leu Pro Ile Glu Tyr Ser His Pro Arg Ala Gln Leu Ala Asp Leu
                500                 505                 510
Met Gly Ala Gly Leu Ser Asp Leu Val Leu Ile Gly Pro Lys Ser Val
            515                 520                 525
Arg Leu Tyr Val Asn Asn Arg Asp Gly Phe Thr Glu Gly Arg Asp Val
        530                 535                 540
Val Gln Ser Gly Asp Ile Thr Leu Pro Leu Pro Gly Ala Asp Ala Arg
545                 550                 555                 560
Lys Leu Val Ala Phe Ser Asp Val Leu Gly Ser Gln Ala His Leu
                565                 570                 575
Val Glu Val Ser Ala Thr Gln Val Thr Cys Trp Pro Asn Leu Gly His
            580                 585                 590
Gly Arg Phe Gly Gln Pro Ile Val Leu Pro Gly Phe Ser Gln Ser Ala
        595                 600                 605
Ala Ser Phe Asn Pro Asp Arg Val His Leu Ala Asp Leu Asp Gly Ser
        610                 615                 620
Gly Pro Ala Asp Leu Ile Tyr Val His Ala Asp Arg Leu Asp Ile Phe
625                 630                 635                 640
Ser Asn Glu Ser Gly Asn Gly Phe Ala Lys Pro Phe Thr Leu Ser Phe
                645                 650                 655
Pro Asp Gly Leu Arg Phe Asp Asp Thr Cys Gln Leu Gln Val Ala Asp
            660                 665                 670
Val Gln Gly Leu Gly Val Val Ser Leu Ile Leu Ser Val Pro His Met
        675                 680                 685
Ala Pro His His Trp Arg Cys Asp Leu Thr Asn Ala Lys Pro Trp Leu
        690                 695                 700
Leu Ser Glu Thr Asn Asn Asn Met Gly Ala Asn His Thr Leu His Tyr
705                 710                 715                 720
Arg Ser Ser Val Gln Phe Trp Leu Asp Glu Lys Ala Ala Leu Ala
                725                 730                 735
Thr Gly Gln Thr Pro Val Cys Tyr Leu Pro Phe Pro Val His Thr Leu
            740                 745                 750
Trp Gln Thr Glu Thr Glu Asp Glu Ile Ser Gly Asn Lys Leu Val Thr
            755                 760                 765
Thr Leu Arg Tyr Ala His Gly Ala Trp Asp Gly Arg Glu Arg Glu Phe
        770                 775                 780
Arg Gly Phe Gly Tyr Val Glu Gln Thr Asp Ser His Gln Leu Ala Gln
785                 790                 795                 800
Gly Asn Ala Pro Glu Arg Thr Pro Pro Ala Leu Thr Lys Ser Trp Tyr
                805                 810                 815
```

```
Ala Thr Gly Leu Pro Ala Val Asp Asn Ala Leu Ser Ala Gly Tyr Trp
            820                 825                 830

Arg Gly Asp Lys Gln Ala Phe Ala Gly Phe Thr Pro Arg Phe Thr Leu
            835                 840                 845

Trp Lys Glu Gly Lys Asp Val Pro Leu Thr Pro Glu Asp Asp His Asn
            850                 855                 860

Leu Tyr Trp Leu Asn Arg Ala Leu Lys Gly Gln Pro Leu Arg Ser Glu
865                 870                 875                 880

Leu Tyr Gly Leu Asp Gly Ser Ala Gln Gln Ile Pro Tyr Thr Val
                885                 890                 895

Thr Glu Ser Arg Pro Gln Val Arg Gln Leu Gln Asp Gly Ala Thr Val
            900                 905                 910

Ser Pro Val Leu Trp Ala Ser Val Glu Ser Arg Ser Tyr His Tyr
            915                 920                 925

Glu Arg Ile Ile Ser Asp Pro Gln Cys Asn Gln Asp Ile Thr Leu Ser
            930                 935                 940

Ser Asp Leu Phe Gly Gln Pro Leu Lys Gln Val Ser Val Gln Tyr Pro
945                 950                 955                 960

Arg Arg Asn Lys Pro Thr Thr Asn Pro Tyr Pro Asp Thr Leu Pro Asp
                965                 970                 975

Thr Leu Phe Ala Ser Ser Tyr Asp Asp Gln Gln Gln Leu Leu Arg Leu
            980                 985                 990

Thr Cys Arg Gln Ser Ser Trp His  His Leu Ile Gly Asn  Glu Leu Arg
            995                 1000                 1005

Val Leu  Gly Leu Pro Asp Gly  Thr Arg Ser Asp Ala  Phe Thr Tyr
     1010                 1015                 1020

Asp Ala  Lys Gln Val Pro Val  Asp Gly Leu Asn Leu  Glu Thr Leu
     1025                 1030                 1035

Cys Ala  Glu Asn Ser Leu Ile  Ala Asp Asp Lys Pro  Arg Glu Tyr
     1040                 1045                 1050

Leu Asn  Gln Gln Arg Thr Phe  Tyr Thr Asp Gly Lys  Asn Gln Thr
     1055                 1060                 1065

Pro Leu  Lys Thr Pro Thr Arg  Gln Ala Leu Ile Ala  Phe Thr Glu
     1070                 1075                 1080

Thr Ala  Val Leu Thr Glu Ser  Leu Leu Ser Ala Phe  Asp Gly Gly
     1085                 1090                 1095

Ile Thr  Pro Asp Glu Leu Pro  Gly Ile Leu Thr Gln  Ala Gly Tyr
     1100                 1105                 1110

Gln Gln  Glu Pro Tyr Leu Phe  Pro Arg Thr Gly Glu  Asn Lys Val
     1115                 1120                 1125

Trp Val  Ala Arg Gln Gly Tyr  Thr Asp Tyr Gly Thr  Glu Ala Gln
     1130                 1135                 1140

Phe Trp  Arg Pro Val Ala Gln  Arg Asn Ser Leu Leu  Thr Gly Lys
     1145                 1150                 1155

Met Thr  Leu Lys Trp Asp Thr  His Tyr Cys Val Ile  Thr Gln Thr
     1160                 1165                 1170

Gln Asp  Ala Ala Gly Leu Thr  Val Ser Ala Asn Tyr  Asp Trp Arg
     1175                 1180                 1185

Phe Leu  Thr Pro Thr Gln Leu  Thr Asp Ile Asn Asp  Asn Val His
     1190                 1195                 1200

Leu Ile  Thr Leu Asp Ala Leu  Gly Arg Pro Val Thr  Gln Arg Phe
     1205                 1210                 1215
```

-continued

```
Trp Gly Ile Glu Ser Gly Val Ala Thr Gly Tyr Ser Ser Ser Glu
1220             1225                 1230

Glu Lys Pro Phe Ser Pro Pro Asn Asp Ile Asp Thr Ala Ile Asn
    1235             1240                 1245

Leu Thr Gly Pro Leu Pro Val Ala Gln Cys Leu Val Tyr Ala Pro
1250             1255                 1260

Asp Ser Trp Met Pro Leu Phe Ser Gln Glu Thr Phe Asn Thr Leu
    1265             1270                 1275

Thr Gln Glu Glu Gln Glu Thr Leu Arg Asp Ser Arg Ile Ile Thr
1280             1285                 1290

Glu Asp Trp Arg Ile Cys Ala Leu Thr Arg Arg Arg Trp Leu Gln
    1295             1300                 1305

Ser Gln Lys Ile Ser Thr Pro Leu Val Lys Leu Leu Thr Asn Ser
1310             1315                 1320

Ile Gly Leu Pro Pro His Asn Leu Thr Leu Thr Thr Asp Arg Tyr
    1325             1330                 1335

Asp Arg Asp Ser Glu Gln Gln Ile Arg Gln Gln Val Ala Phe Ser
1340             1345                 1350

Asp Gly Phe Gly Arg Leu Leu Gln Ala Ser Val Arg His Glu Ala
    1355             1360                 1365

Gly Glu Ala Trp Gln Arg Asn Gln Asp Gly Ser Leu Val Thr Lys
1370             1375                 1380

Val Glu Asn Thr Lys Thr Arg Trp Ala Val Thr Gly Arg Thr Glu
    1385             1390                 1395

Tyr Asp Asn Lys Gly Gln Thr Ile Arg Thr Tyr Gln Pro Tyr Phe
1400             1405                 1410

Leu Asn Asp Trp Arg Tyr Val Ser Asp Asp Ser Ala Arg Lys Glu
    1415             1420                 1425

Ala Tyr Ala Asp Thr His Ile Tyr Asp Pro Ile Gly Arg Glu Ile
1430             1435                 1440

Arg Val Ile Thr Ala Lys Gly Trp Leu Arg Gln Ser Gln Tyr Phe
    1445             1450                 1455

Pro Trp Phe Thr Val Ser Glu Asp Glu Asn Asp Thr Ala Ala Asp
1460             1465                 1470

Ala Leu Val
    1475

<210> SEQ ID NO 8
<211> LENGTH: 1474
<212> TYPE: PRT
<213> ORGANISM: Photorhabdus luminescens

<400> SEQUENCE: 8

Met Gln Asn Ser Gln Asp Phe Ser Ile Thr Glu Leu Ser Leu Pro Lys
1               5                   10                  15

Gly Gly Gly Ala Ile Thr Gly Met Gly Glu Ala Leu Thr Pro Thr Gly
            20                  25                  30

Pro Asp Gly Met Ala Ala Leu Ser Leu Pro Leu Pro Ile Ser Ala Gly
        35                  40                  45

Arg Gly Tyr Ala Pro Ala Phe Thr Leu Asn Tyr Asn Ser Gly Ala Gly
    50                  55                  60

Asn Ser Pro Phe Gly Leu Gly Trp Asp Cys Asn Val Met Thr Ile Arg
65                  70                  75                  80

Arg Arg Thr His Phe Gly Val Pro His Tyr Asp Glu Thr Asp Thr Phe
                85                  90                  95
```

```
Leu Gly Pro Glu Gly Glu Val Leu Val Ala Asp Gln Pro Arg Asp
            100                 105                 110
Glu Ser Thr Leu Gln Gly Ile Asn Leu Gly Ala Thr Phe Thr Val Thr
        115                 120                 125
Gly Tyr Arg Ser Arg Leu Glu Ser His Phe Ser Arg Leu Glu Tyr Trp
    130                 135                 140
Gln Pro Lys Thr Thr Gly Lys Thr Asp Phe Trp Leu Ile Tyr Ser Pro
145                 150                 155                 160
Asp Gly Gln Val His Leu Leu Gly Lys Ser Pro Gln Ala Arg Ile Ser
                165                 170                 175
Asn Pro Ser Gln Thr Thr Gln Thr Ala Gln Trp Leu Leu Glu Ala Ser
            180                 185                 190
Val Ser Ser Arg Gly Glu Gln Ile Tyr Tyr Gln Tyr Arg Ala Glu Asp
        195                 200                 205
Asp Thr Gly Cys Glu Ala Asp Glu Ile Thr His His Leu Gln Ala Thr
    210                 215                 220
Ala Gln Arg Tyr Leu His Ile Val Tyr Tyr Gly Asn Arg Thr Ala Ser
225                 230                 235                 240
Glu Thr Leu Pro Gly Leu Asp Gly Ser Ala Pro Ser Gln Ala Asp Trp
                245                 250                 255
Leu Phe Tyr Leu Val Phe Asp Tyr Gly Glu Arg Ser Asn Asn Leu Lys
            260                 265                 270
Thr Pro Pro Ala Phe Ser Thr Thr Gly Ser Trp Leu Cys Arg Gln Asp
        275                 280                 285
Arg Phe Ser Arg Tyr Glu Tyr Gly Phe Glu Ile Arg Thr Arg Arg Leu
    290                 295                 300
Cys Arg Gln Val Leu Met Tyr His His Leu Gln Ala Leu Asp Ser Lys
305                 310                 315                 320
Ile Thr Glu His Asn Gly Pro Thr Leu Val Ser Arg Leu Ile Leu Asn
                325                 330                 335
Tyr Asp Glu Ser Ala Ile Ala Ser Thr Leu Val Phe Val Arg Arg Val
            340                 345                 350
Gly His Glu Gln Asp Gly Asn Val Val Thr Leu Pro Pro Leu Glu Leu
        355                 360                 365
Ala Tyr Gln Asp Phe Ser Pro Arg His His Ala His Trp Gln Pro Met
    370                 375                 380
Asp Val Leu Ala Asn Phe Asn Ala Ile Gln Arg Trp Gln Leu Val Asp
385                 390                 395                 400
Leu Lys Gly Glu Gly Leu Pro Gly Leu Leu Tyr Gln Asp Lys Gly Ala
                405                 410                 415
Trp Trp Tyr Arg Ser Ala Gln Arg Leu Gly Glu Ile Gly Ser Asp Ala
            420                 425                 430
Val Thr Trp Glu Lys Met Gln Pro Leu Ser Val Ile Pro Ser Leu Gln
        435                 440                 445
Ser Asn Ala Ser Leu Val Asp Ile Asn Gly Asp Gly Gln Leu Asp Trp
    450                 455                 460
Val Ile Thr Gly Pro Gly Leu Arg Gly Tyr His Ser Gln Arg Pro Asp
465                 470                 475                 480
Gly Ser Trp Thr Arg Phe Thr Pro Leu Asn Ala Leu Pro Val Glu Tyr
                485                 490                 495
Thr His Pro Arg Ala Gln Leu Ala Asp Leu Met Gly Ala Gly Leu Ser
            500                 505                 510
```

-continued

```
Asp Leu Val Leu Ile Gly Pro Lys Ser Val Arg Leu Tyr Ala Asn Thr
            515                 520                 525

Arg Asp Gly Phe Ala Lys Gly Lys Asp Val Val Gln Ser Gly Asp Ile
    530                 535                 540

Thr Leu Pro Val Pro Gly Ala Asp Pro Arg Lys Leu Val Ala Phe Ser
545                 550                 555                 560

Asp Val Leu Gly Ser Gly Gln Ala His Leu Val Glu Val Ser Ala Thr
                565                 570                 575

Lys Val Thr Cys Trp Pro Asn Leu Gly Arg Gly Arg Phe Gly Gln Pro
            580                 585                 590

Ile Thr Leu Pro Gly Phe Ser Gln Pro Ala Thr Glu Phe Asn Pro Ala
                595                 600                 605

Gln Val Tyr Leu Ala Asp Leu Asp Gly Ser Gly Pro Thr Asp Leu Ile
            610                 615                 620

Tyr Val His Thr Asn Arg Leu Asp Ile Phe Leu Asn Lys Ser Gly Asn
625                 630                 635                 640

Gly Phe Ala Glu Pro Val Thr Leu Arg Phe Pro Glu Gly Leu Arg Phe
                645                 650                 655

Asp His Thr Cys Gln Leu Gln Met Ala Asp Val Gln Gly Leu Gly Val
            660                 665                 670

Ala Ser Leu Ile Leu Ser Val Pro His Met Ser Pro His His Trp Arg
        675                 680                 685

Cys Asp Leu Thr Asn Met Lys Pro Trp Leu Leu Asn Glu Met Asn Asn
    690                 695                 700

Asn Met Gly Val His His Thr Leu Arg Tyr Arg Ser Ser Ser Gln Phe
705                 710                 715                 720

Trp Leu Asp Glu Lys Ala Ala Ala Leu Thr Thr Gly Gln Thr Pro Val
                725                 730                 735

Cys Tyr Leu Pro Phe Pro Ile His Thr Leu Trp Gln Thr Glu Thr Glu
            740                 745                 750

Asp Glu Ile Ser Gly Asn Lys Leu Val Thr Thr Leu Arg Tyr Ala Arg
        755                 760                 765

Gly Ala Trp Asp Gly Arg Arg Glu Phe Arg Gly Phe Gly Tyr Val
    770                 775                 780

Glu Gln Thr Asp Ser His Gln Leu Ala Gln Gly Asn Ala Pro Glu Arg
785                 790                 795                 800

Thr Pro Pro Ala Leu Thr Lys Asn Trp Tyr Ala Thr Gly Leu Pro Val
                805                 810                 815

Ile Asp Asn Ala Leu Ser Thr Glu Tyr Trp Arg Asp Gln Ala Phe
            820                 825                 830

Ala Gly Phe Ser Pro Arg Phe Thr Thr Trp Gln Asp Asn Lys Asp Val
        835                 840                 845

Pro Leu Thr Pro Glu Asp Asp Asn Ser Arg Tyr Trp Phe Asn Arg Ala
850                 855                 860

Leu Lys Gly Gln Leu Leu Arg Ser Glu Leu Tyr Gly Leu Asp Asp Ser
865                 870                 875                 880

Thr Asn Lys His Val Pro Tyr Thr Val Thr Glu Phe Arg Ser Gln Val
                885                 890                 895

Arg Arg Leu Gln His Thr Asp Ser Arg Tyr Pro Val Leu Trp Ser Ser
            900                 905                 910

Val Val Glu Ser Arg Asn Tyr His Tyr Glu Arg Ile Ala Ser Asp Pro
        915                 920                 925

Gln Cys Ser Gln Asn Ile Thr Leu Ser Ser Asp Arg Phe Gly Gln Pro
```

-continued

```
            930                 935                 940
Leu Lys Gln Leu Ser Val Gln Tyr Pro Arg Arg Gln Pro Ala Ile
945                 950                 955                 960

Asn Leu Tyr Pro Asp Thr Leu Pro Asp Lys Leu Leu Ala Asn Ser Tyr
                965                 970                 975

Asp Asp Gln Gln Arg Gln Leu Arg Leu Thr Tyr Gln Gln Ser Ser Trp
                980                 985                 990

His His Leu Thr Asn Asn Thr Val Arg Val Leu Gly Leu Pro Asp Ser
                995                 1000                1005

Thr Arg Ser Asp Ile Phe Thr Tyr Gly Ala Glu Asn Val Pro Ala
    1010                1015                1020

Gly Gly Leu Asn Leu Glu Leu Leu Ser Asp Lys Asn Ser Leu Ile
    1025                1030                1035

Ala Asp Asp Lys Pro Arg Glu Tyr Leu Gly Gln Gln Lys Thr Ala
    1040                1045                1050

Tyr Thr Asp Gly Gln Asn Thr Thr Pro Leu Gln Thr Pro Thr Arg
    1055                1060                1065

Gln Ala Leu Ile Ala Phe Thr Glu Thr Thr Val Phe Asn Gln Ser
    1070                1075                1080

Thr Leu Ser Ala Phe Asn Gly Ser Ile Pro Ser Asp Lys Leu Ser
    1085                1090                1095

Thr Thr Leu Glu Gln Ala Gly Tyr Gln Gln Thr Asn Tyr Leu Phe
    1100                1105                1110

Pro Arg Thr Gly Glu Asp Lys Val Trp Val Ala His His Gly Tyr
    1115                1120                1125

Thr Asp Tyr Gly Thr Ala Ala Gln Phe Trp Arg Pro Gln Lys Gln
    1130                1135                1140

Ser Asn Thr Gln Leu Thr Gly Lys Ile Thr Leu Ile Trp Asp Ala
    1145                1150                1155

Asn Tyr Cys Val Val Val Gln Thr Arg Asp Ala Ala Gly Leu Thr
    1160                1165                1170

Thr Ser Ala Lys Tyr Asp Trp Arg Phe Leu Thr Pro Val Gln Leu
    1175                1180                1185

Thr Asp Ile Asn Asp Asn Gln His Leu Ile Thr Leu Asp Ala Leu
    1190                1195                1200

Gly Arg Pro Ile Thr Leu Arg Phe Trp Gly Thr Glu Asn Gly Lys
    1205                1210                1215

Met Thr Gly Tyr Ser Ser Pro Glu Lys Ala Ser Phe Ser Pro Pro
    1220                1225                1230

Ser Asp Val Asn Ala Ala Ile Glu Leu Lys Lys Pro Leu Pro Val
    1235                1240                1245

Ala Gln Cys Gln Val Tyr Ala Pro Glu Ser Trp Met Pro Val Leu
    1250                1255                1260

Ser Gln Lys Thr Phe Asn Arg Leu Ala Glu Gln Asp Trp Gln Lys
    1265                1270                1275

Leu Tyr Asn Ala Arg Ile Ile Thr Glu Asp Gly Arg Ile Cys Thr
    1280                1285                1290

Leu Ala Tyr Arg Arg Trp Val Gln Ser Gln Lys Ala Ile Pro Gln
    1295                1300                1305

Leu Ile Ser Leu Leu Asn Asn Gly Pro Arg Leu Pro Pro His Ser
    1310                1315                1320

Leu Thr Leu Thr Thr Asp Arg Tyr Asp His Asp Pro Glu Gln Gln
    1325                1330                1335
```

-continued

```
Ile Arg Gln Gln Val Val Phe Ser Asp Gly Phe Gly Arg Leu Leu
    1340            1345                1350

Gln Ala Ala Ala Arg His Glu Ala Gly Met Ala Arg Gln Arg Asn
    1355                1360                1365

Glu Asp Gly Ser Leu Ile Ile Asn Val Gln His Thr Glu Asn Arg
    1370            1375                1380

Trp Ala Val Thr Gly Arg Thr Glu Tyr Asp Asn Lys Gly Gln Pro
    1385            1390                1395

Ile Arg Thr Tyr Gln Pro Tyr Phe Leu Asn Asp Trp Arg Tyr Val
    1400            1405                1410

Ser Asn Asp Ser Ala Arg Gln Glu Lys Glu Ala Tyr Ala Asp Thr
    1415            1420                1425

His Val Tyr Asp Pro Ile Gly Arg Glu Ile Lys Val Ile Thr Ala
    1430            1435                1440

Lys Gly Trp Phe Arg Arg Thr Leu Phe Thr Pro Trp Phe Thr Val
    1445            1450                1455

Asn Glu Asp Glu Asn Asp Thr Ala Ala Glu Val Lys Lys Val Lys
    1460            1465                1470

Met
```

```
<210> SEQ ID NO 9
<211> LENGTH: 4458
<212> TYPE: DNA
<213> ORGANISM: Photorhabdus luminescens strain W14
<220> FEATURE:
<221> NAME/KEY: exon
<222> LOCATION: (1)..(4458)

<400> SEQUENCE: 9
```

```
atg cag gat tca cca gaa gta tcg att aca acg ctg tca ctt ccc aaa      48
Met Gln Asp Ser Pro Glu Val Ser Ile Thr Thr Leu Ser Leu Pro Lys
1               5                   10                  15 ggt ggc ggt gct atc aat ggc atg gga gaa gca ctg aat gct gcc ggc      96
Gly Gly Gly Ala Ile Asn Gly Met Gly Glu Ala Leu Asn Ala Ala Gly
                20                  25                  30 cct gat gga atg gcc tcc cta tct ctg cca tta ccc ctt tcg acc ggc     144
Pro Asp Gly Met Ala Ser Leu Ser Leu Pro Leu Pro Leu Ser Thr Gly
            35                  40                  45 aga ggg acg gct cct gga tta tcg ctg att tac agc aac agt gca ggt     192
Arg Gly Thr Ala Pro Gly Leu Ser Leu Ile Tyr Ser Asn Ser Ala Gly
        50                  55                  60 aat ggg cct ttc ggc atc ggc tgg caa tgc ggt gtt atg tcc att agc     240
Asn Gly Pro Phe Gly Ile Gly Trp Gln Cys Gly Val Met Ser Ile Ser
65                  70                  75                  80 cga cgc acc caa cat ggc att cca caa tac ggt aat gac gac acg ttc     288
Arg Arg Thr Gln His Gly Ile Pro Gln Tyr Gly Asn Asp Asp Thr Phe
                85                  90                  95 cta tcc cca caa ggc gag gtc atg aat atc gcc ctg aat gac caa ggg     336
Leu Ser Pro Gln Gly Glu Val Met Asn Ile Ala Leu Asn Asp Gln Gly
            100                 105                 110 caa cct gat atc cgt caa gac gtt aaa acg ctg caa ggc gtt acc ttg     384
Gln Pro Asp Ile Arg Gln Asp Val Lys Thr Leu Gln Gly Val Thr Leu
        115                 120                 125 cca att tcc tat acc gtg acc cgc tat caa gcc cgc cag atc ctg gat     432
Pro Ile Ser Tyr Thr Val Thr Arg Tyr Gln Ala Arg Gln Ile Leu Asp
    130                 135                 140 ttc agt aaa atc gaa tac tgg caa cct gcc tcc ggt caa gaa gga cgc     480
Phe Ser Lys Ile Glu Tyr Trp Gln Pro Ala Ser Gly Gln Glu Gly Arg
```

-continued

```
                   145                 150                 155                 160
gct ttc tgg ctg ata tcg tca ccg gac ggc caa cta cac atc tta ggg         528
Ala Phe Trp Leu Ile Ser Ser Pro Asp Gly Gln Leu His Ile Leu Gly
                165                 170                 175 aaa acc gcg cag gct tgt ctg gca aat ccg caa aat gac caa caa atc         576
Lys Thr Ala Gln Ala Cys Leu Ala Asn Pro Gln Asn Asp Gln Gln Ile
            180                 185                 190 gcc cag tgg ttg ctg gaa gaa act gtg acg cca gcc ggt gaa cat gtc         624
Ala Gln Trp Leu Leu Glu Glu Thr Val Thr Pro Ala Gly Glu His Val
        195                 200                 205 agc tat caa tat cga gcc gaa gat gaa gcc cat tgt gac gac aat gaa         672
Ser Tyr Gln Tyr Arg Ala Glu Asp Glu Ala His Cys Asp Asp Asn Glu
    210                 215                 220 aaa acc gct cat ccc aat gtt acc gca cag cgc tat ctg gta cag gtg         720
Lys Thr Ala His Pro Asn Val Thr Ala Gln Arg Tyr Leu Val Gln Val
225                 230                 235                 240 aac tac ggc aac atc aaa cca caa gcc agc ctg ttc gta ctg gat aac         768
Asn Tyr Gly Asn Ile Lys Pro Gln Ala Ser Leu Phe Val Leu Asp Asn
                245                 250                 255 gca cct ccc gca ccg gaa gag tgg ctg ttt cat ctg gtc ttt gac cac         816
Ala Pro Pro Ala Pro Glu Glu Trp Leu Phe His Leu Val Phe Asp His
            260                 265                 270 ggt gag cgc gat acc tca ctt cat acc gtg cca aca tgg gat gca ggt         864
Gly Glu Arg Asp Thr Ser Leu His Thr Val Pro Thr Trp Asp Ala Gly
        275                 280                 285 aca gcg caa tgg tct gta cgc ccg gat atc ttc tct cgc tat gaa tat         912
Thr Ala Gln Trp Ser Val Arg Pro Asp Ile Phe Ser Arg Tyr Glu Tyr
    290                 295                 300 ggt ttt gaa gtg cgt act cgc cgc tta tgt caa caa gtg ctg atg ttt         960
Gly Phe Glu Val Arg Thr Arg Arg Leu Cys Gln Gln Val Leu Met Phe
305                 310                 315                 320 cac cgc acc gcg ctc atg gcc gga gaa gcc agt acc aat gac gcc ccg        1008
His Arg Thr Ala Leu Met Ala Gly Glu Ala Ser Thr Asn Asp Ala Pro
                325                 330                 335 gaa ctg gtt gga cgc tta ata ctg gaa tat gac aaa aac gcc agc gtc        1056
Glu Leu Val Gly Arg Leu Ile Leu Glu Tyr Asp Lys Asn Ala Ser Val
            340                 345                 350 acc acg ttg att acc atc cgt caa tta agc cat gaa tcg gac ggc agc        1104
Thr Thr Leu Ile Thr Ile Arg Gln Leu Ser His Glu Ser Asp Gly Ser
        355                 360                 365 cca gtc acc cag cca cca cta gaa cta gcc tgg caa cgg ttt gat ctg        1152
Pro Val Thr Gln Pro Pro Leu Glu Leu Ala Trp Gln Arg Phe Asp Leu
    370                 375                 380 gag aaa atg ccg aca tgg caa cgc ttt gac gca cta gat aat ttt aac        1200
Glu Lys Met Pro Thr Trp Gln Arg Phe Asp Ala Leu Asp Asn Phe Asn
385                 390                 395                 400 tcg cag caa cgt tat caa ctg gtt gat ctg cgg gga gaa ggg ttg cca        1248
Ser Gln Gln Arg Tyr Gln Leu Val Asp Leu Arg Gly Glu Gly Leu Pro
                405                 410                 415 ggt atg ctg tat caa gat cga ggc gct tgg tgg tat aaa gct ccg caa        1296
Gly Met Leu Tyr Gln Asp Arg Gly Ala Trp Trp Tyr Lys Ala Pro Gln
            420                 425                 430 cgt cag gaa gac gga gac agc aat gcc gtc act tac gac aaa atc gcc        1344
Arg Gln Glu Asp Gly Asp Ser Asn Ala Val Thr Tyr Asp Lys Ile Ala
        435                 440                 445 cca ctg cct acc cta ccc aat ttg cag gat aat gcc tca ttg atg gat        1392
Pro Leu Pro Thr Leu Pro Asn Leu Gln Asp Asn Ala Ser Leu Met Asp
    450                 455                 460 atc aac gga gac ggc caa ctg gat tgg gtt gtt acc gcc tcc ggt att        1440
Ile Asn Gly Asp Gly Gln Leu Asp Trp Val Val Thr Ala Ser Gly Ile
```

```
Ile Asn Gly Asp Gly Gln Leu Asp Trp Val Val Thr Ala Ser Gly Ile
465                 470                 475                 480 cgc gga tac cat agt cag caa ccc gat gga aag tgg acg cac ttt acg    1488
Arg Gly Tyr His Ser Gln Gln Pro Asp Gly Lys Trp Thr His Phe Thr
                    485                 490                 495 cca atc aat gcc ttg ccc gtg gaa tat ttt cat cca agc atc cag ttc    1536
Pro Ile Asn Ala Leu Pro Val Glu Tyr Phe His Pro Ser Ile Gln Phe
                500                 505                 510 gct gac ctt acc ggg gca ggc tta tct gat tta gtg ttg atc ggg ccg    1584
Ala Asp Leu Thr Gly Ala Gly Leu Ser Asp Leu Val Leu Ile Gly Pro
            515                 520                 525 aaa agc gtg cgt cta tat gcc aac cag cga aac ggc tgg cgt aaa gga    1632
Lys Ser Val Arg Leu Tyr Ala Asn Gln Arg Asn Gly Trp Arg Lys Gly
        530                 535                 540 gaa gat gtc ccc caa tcc aca ggt atc acc ctg cct gtc aca ggg acc    1680
Glu Asp Val Pro Gln Ser Thr Gly Ile Thr Leu Pro Val Thr Gly Thr
545                 550                 555                 560 gat gcc cgc aaa ctg gtg gct ttc agt gat atg ctc ggt tcc ggt caa    1728
Asp Ala Arg Lys Leu Val Ala Phe Ser Asp Met Leu Gly Ser Gly Gln
                    565                 570                 575 caa cat ctg gtg gaa atc aag gct aat cgc gtc acc tgt tgg ccg aat    1776
Gln His Leu Val Glu Ile Lys Ala Asn Arg Val Thr Cys Trp Pro Asn
                580                 585                 590 cta ggg cat ggc cgt ttc ggt caa cca cta act ctg tca gga ttt agc    1824
Leu Gly His Gly Arg Phe Gly Gln Pro Leu Thr Leu Ser Gly Phe Ser
            595                 600                 605 cag ccc gaa aat agc ttc aat ccc gaa cgg ctg ttt ctg gcg gat atc    1872
Gln Pro Glu Asn Ser Phe Asn Pro Glu Arg Leu Phe Leu Ala Asp Ile
        610                 615                 620 gac ggc tcc ggc acc acc gac ctt atc tat gcg caa tcc ggc tct ttg    1920
Asp Gly Ser Gly Thr Thr Asp Leu Ile Tyr Ala Gln Ser Gly Ser Leu
625                 630                 635                 640 ctc att tat ctc aac caa agt ggt aat cag ttt gat gcc ccg ttg aca    1968
Leu Ile Tyr Leu Asn Gln Ser Gly Asn Gln Phe Asp Ala Pro Leu Thr
                    645                 650                 655 tta gcg ttg cca gaa ggc gta caa ttt gac aac act tgc caa ctt caa    2016
Leu Ala Leu Pro Glu Gly Val Gln Phe Asp Asn Thr Cys Gln Leu Gln
                660                 665                 670 gtc gcc gat att cag gga tta ggg ata gcc agc ttg att ctg act gtg    2064
Val Ala Asp Ile Gln Gly Leu Gly Ile Ala Ser Leu Ile Leu Thr Val
            675                 680                 685 cca cat atc gcg cca cat cac tgg cgt tgt gac ctg tca ctg acc aaa    2112
Pro His Ile Ala Pro His His Trp Arg Cys Asp Leu Ser Leu Thr Lys
        690                 695                 700 ccc tgg ttg ttg aat gta atg aac aat aac cgg ggc gca cat cac acg    2160
Pro Trp Leu Leu Asn Val Met Asn Asn Asn Arg Gly Ala His His Thr
705                 710                 715                 720 cta cat tat cgt agt tcc gcg caa ttc tgg ttg gat gaa aaa tta cag    2208
Leu His Tyr Arg Ser Ser Ala Gln Phe Trp Leu Asp Glu Lys Leu Gln
                    725                 730                 735 ctc acc aaa gca ggc aaa tct ccg gct tgt tat ctg ccg ttt cca atg    2256
Leu Thr Lys Ala Gly Lys Ser Pro Ala Cys Tyr Leu Pro Phe Pro Met
                740                 745                 750 cat ttg cta tgg tat acc gaa att cag gat gaa atc agc ggc aac cgg    2304
His Leu Leu Trp Tyr Thr Glu Ile Gln Asp Glu Ile Ser Gly Asn Arg
            755                 760                 765 ctc acc agt gaa gtc aac tac agc cac ggc gtc tgg gat ggt aaa gag    2352
Leu Thr Ser Glu Val Asn Tyr Ser His Gly Val Trp Asp Gly Lys Glu
        770                 775                 780
```

-continued

| | | |
|---|---|---|
| cgg gaa ttc aga gga ttt ggc tgc atc aaa cag aca gat acc aca acg<br>Arg Glu Phe Arg Gly Phe Gly Cys Ile Lys Gln Thr Asp Thr Thr Thr<br>785                        790                     795                     800 | 2400 |

```
cgg gaa ttc aga gga ttt ggc tgc atc aaa cag aca gat acc aca acg      2400
Arg Glu Phe Arg Gly Phe Gly Cys Ile Lys Gln Thr Asp Thr Thr Thr
785                 790                 795                 800 ttt tct cac ggc acc gcc ccc gaa cag gcg gca ccg tcg ctg agt att      2448
Phe Ser His Gly Thr Ala Pro Glu Gln Ala Ala Pro Ser Leu Ser Ile
                805                 810                 815 agc tgg ttt gcc acc ggc atg gat gaa gta gac agc caa tta gct acg      2496
Ser Trp Phe Ala Thr Gly Met Asp Glu Val Asp Ser Gln Leu Ala Thr
            820                 825                 830 gaa tat tgg cag gca gac acg caa gct tat agc gga ttt gaa acc cgt      2544
Glu Tyr Trp Gln Ala Asp Thr Gln Ala Tyr Ser Gly Phe Glu Thr Arg
        835                 840                 845 tat acc gtc tgg gat cac acc aac cag aca gac caa gca ttt acc ccc      2592
Tyr Thr Val Trp Asp His Thr Asn Gln Thr Asp Gln Ala Phe Thr Pro
    850                 855                 860 aat gag aca caa cgt aac tgg ctg acg cga gcg ctt aaa ggc caa ctg      2640
Asn Glu Thr Gln Arg Asn Trp Leu Thr Arg Ala Leu Lys Gly Gln Leu
865                 870                 875                 880 cta cgc act gag ctc tac ggt ctg gac gga aca gat aag caa aca gtg      2688
Leu Arg Thr Glu Leu Tyr Gly Leu Asp Gly Thr Asp Lys Gln Thr Val
                885                 890                 895 cct tat acc gtc agt gaa tcg cgc tat cag gta cgc tct att ccc gta      2736
Pro Tyr Thr Val Ser Glu Ser Arg Tyr Gln Val Arg Ser Ile Pro Val
                900                 905                 910 aat aaa gaa act gaa tta tct gcc tgg gtg act gct att gaa aat cgc      2784
Asn Lys Glu Thr Glu Leu Ser Ala Trp Val Thr Ala Ile Glu Asn Arg
            915                 920                 925 agc tac cac tat gaa cgt atc atc act gac cca cag ttc agc cag agt      2832
Ser Tyr His Tyr Glu Arg Ile Ile Thr Asp Pro Gln Phe Ser Gln Ser
        930                 935                 940 atc aag ttg caa cac gat atc ttt ggt caa tca ctg caa agt gtc gat      2880
Ile Lys Leu Gln His Asp Ile Phe Gly Gln Ser Leu Gln Ser Val Asp
945                 950                 955                 960 att gcc tgg ccg cgc cgc gaa aaa cca gca gtg aat ccc tac ccg cct      2928
Ile Ala Trp Pro Arg Arg Glu Lys Pro Ala Val Asn Pro Tyr Pro Pro
                965                 970                 975 acc ctg ccg gaa acg cta ttt gac agc agc tat gat gat caa caa caa      2976
Thr Leu Pro Glu Thr Leu Phe Asp Ser Ser Tyr Asp Asp Gln Gln Gln
                980                 985                 990 cta tta cgt ctg gtg aga caa aaa  aat agc tgg cat cac  ctg act gat   3024
Leu Leu Arg Leu Val Arg Gln Lys  Asn Ser Trp His His  Leu Thr Asp
            995                 1000                1005 ggg gaa  aac tgg cga tta ggt  tta ccg aat gca caa  cgc cgt gat      3069
Gly Glu  Asn Trp Arg Leu Gly  Leu Pro Asn Ala Gln  Arg Arg Asp
1010                 1015                1020 gtt tat  act tat gac cgg agc  aaa att cca acc gaa  ggg att tcc      3114
Val Tyr  Thr Tyr Asp Arg Ser  Lys Ile Pro Thr Glu  Gly Ile Ser
    1025                1030                1035 ctt gaa  atc ttg ctg aaa gat  gat ggc ctg cta gca  gat gaa aaa      3159
Leu Glu  Ile Leu Leu Lys Asp  Asp Gly Leu Leu Ala  Asp Glu Lys
    1040                1045                1050 gcg gcc  gtt tat ctg gga caa  caa cag acg ttt tac  acc gcc ggt      3204
Ala Ala  Val Tyr Leu Gly Gln  Gln Gln Thr Phe Tyr  Thr Ala Gly
    1055                1060                1065 caa gcg  gaa gtc act cta gaa  aaa ccc acg tta caa  gca ctg gtc      3249
Gln Ala  Glu Val Thr Leu Glu  Lys Pro Thr Leu Gln  Ala Leu Val
    1070                1075                1080 gcg ttc  caa gaa acc gcc atg  atg gac gat acc tca  tta cag gcg      3294
Ala Phe  Gln Glu Thr Ala Met  Met Asp Asp Thr Ser  Leu Gln Ala
    1085                1090                1095
```

```
tat gaa ggc gtg att gaa gag caa gag ttg aat acc gcg ctg aca    3339
Tyr Glu Gly Val Ile Glu Glu Gln Glu Leu Asn Thr Ala Leu Thr
    1100            1105                1110 cag gcc ggt tat cag caa gtc gcg cgg ttg ttt aat acc aga tca    3384
Gln Ala Gly Tyr Gln Gln Val Ala Arg Leu Phe Asn Thr Arg Ser
    1115            1120                1125 gaa agc ccg gta tgg gcg gca cgg caa ggt tat acc gat tac ggt    3429
Glu Ser Pro Val Trp Ala Ala Arg Gln Gly Tyr Thr Asp Tyr Gly
    1130            1135                1140 gac gcc gca cag ttc tgg cgg cct cag gct cag cgt aac tcg ttg    3474
Asp Ala Ala Gln Phe Trp Arg Pro Gln Ala Gln Arg Asn Ser Leu
    1145            1150                1155 ctg aca ggg aaa aca ctg acc tgg gat acc cat cat tgt gta        3519
Leu Thr Gly Lys Thr Thr Leu Thr Trp Asp Thr His His Cys Val
    1160            1165                1170 ata ata cag act caa gat gcc gct gga tta acg acg caa gcc cat    3564
Ile Ile Gln Thr Gln Asp Ala Ala Gly Leu Thr Thr Gln Ala His
    1175            1180                1185 tac gat tat cgt ttc ctt aca ccg gta caa ctg aca gat att aat    3609
Tyr Asp Tyr Arg Phe Leu Thr Pro Val Gln Leu Thr Asp Ile Asn
    1190            1195                1200 gat aat caa cat att gtg act ctg gac gcg cta ggt cgc gta acc    3654
Asp Asn Gln His Ile Val Thr Leu Asp Ala Leu Gly Arg Val Thr
    1205            1210                1215 acc agc cgg ttc tgg ggc aca gag gca gga caa gcc gca ggc tat    3699
Thr Ser Arg Phe Trp Gly Thr Glu Ala Gly Gln Ala Ala Gly Tyr
    1220            1225                1230 tcc aac cag ccc ttc aca cca ccg gac tcc gta gat aaa gcg ctg    3744
Ser Asn Gln Pro Phe Thr Pro Pro Asp Ser Val Asp Lys Ala Leu
    1235            1240                1245 gca tta acc ggc gca ctc cct gtt gcc caa tgt tta gtc tat gcc    3789
Ala Leu Thr Gly Ala Leu Pro Val Ala Gln Cys Leu Val Tyr Ala
    1250            1255                1260 gtt gat agc tgg atg ccg tcg tta tct ttg tct cag ctt tct cag    3834
Val Asp Ser Trp Met Pro Ser Leu Ser Leu Ser Gln Leu Ser Gln
    1265            1270                1275 tca caa gaa gag gca gaa gcg cta tgg gcg caa ctg cgt gcc gct    3879
Ser Gln Glu Glu Ala Glu Ala Leu Trp Ala Gln Leu Arg Ala Ala
    1280            1285                1290 cat atg att acc gaa gat ggg aaa gtg tgt gcg tta agc ggg aaa    3924
His Met Ile Thr Glu Asp Gly Lys Val Cys Ala Leu Ser Gly Lys
    1295            1300                1305 cga gga aca agc cat cag aac ctg acg att caa ctt att tcg cta    3969
Arg Gly Thr Ser His Gln Asn Leu Thr Ile Gln Leu Ile Ser Leu
    1310            1315                1320 ttg gca agt att ccc cgt tta ccg cca cat gta ctg ggg atc acc    4014
Leu Ala Ser Ile Pro Arg Leu Pro Pro His Val Leu Gly Ile Thr
    1325            1330                1335 act gat cgc tat gat agc gat ccg caa cag cag cac caa cag acg    4059
Thr Asp Arg Tyr Asp Ser Asp Pro Gln Gln Gln His Gln Gln Thr
    1340            1345                1350 gtg agc ttt agt gac ggt ttt ggc cgg tta ctc cag agt tca gct    4104
Val Ser Phe Ser Asp Gly Phe Gly Arg Leu Leu Gln Ser Ser Ala
    1355            1360                1365 cgt cat gag tca ggt gat gcc tgg caa cgt aaa gag gat ggc ggg    4149
Arg His Glu Ser Gly Asp Ala Trp Gln Arg Lys Glu Asp Gly Gly
    1370            1375                1380 ctg gtc gtg gat gca aat ggc gtt ctg gtc agt gcc cct aca gac    4194
Leu Val Val Asp Ala Asn Gly Val Leu Val Ser Ala Pro Thr Asp
```

```
                1385                1390                1395
acc  cga  tgg  gcc  gtt  tcc  ggt  cgc  aca  gaa  tat  gac  gac  aaa  ggc      4239
Thr  Arg  Trp  Ala  Val  Ser  Gly  Arg  Thr  Glu  Tyr  Asp  Asp  Lys  Gly
1400                     1405                     1410 caa  cct  gtg  cgt  act  tat  caa  ccc  tat  ttt  cta  aat  gac  tgg  cgt      4284
Gln  Pro  Val  Arg  Thr  Tyr  Gln  Pro  Tyr  Phe  Leu  Asn  Asp  Trp  Arg
     1415                     1420                     1425 tac  gtt  agt  gat  gac  agc  gca  cga  gat  gac  ctg  ttt  gcc  gat  acc      4329
Tyr  Val  Ser  Asp  Asp  Ser  Ala  Arg  Asp  Asp  Leu  Phe  Ala  Asp  Thr
          1430                     1435                     1440 cac  ctt  tat  gat  cca  ttg  gga  cgg  gaa  tac  aaa  gtc  atc  act  gct      4374
His  Leu  Tyr  Asp  Pro  Leu  Gly  Arg  Glu  Tyr  Lys  Val  Ile  Thr  Ala
               1445                     1450                     1455 aag  aaa  tat  ttg  cga  gaa  aag  ctg  tac  acc  ccg  tgg  ttt  att  gtc      4419
Lys  Lys  Tyr  Leu  Arg  Glu  Lys  Leu  Tyr  Thr  Pro  Trp  Phe  Ile  Val
1460                     1465                     1470 agt  gag  gat  gaa  aac  gat  aca  gca  tca  aga  acc  cca  tag               4458
Ser  Glu  Asp  Glu  Asn  Asp  Thr  Ala  Ser  Arg  Thr  Pro
     1475                     1480                     1485

<210> SEQ ID NO 10
<211> LENGTH: 1493
<212> TYPE: PRT
<213> ORGANISM: Xenorhabdus nematophilus

<400> SEQUENCE: 10

Met Gln Gly Ser Thr Pro Leu Lys Leu Glu Ile Pro Ser Leu Pro Ser
1               5                   10                  15

Gly Gly Gly Ser Leu Lys Gly Met Gly Glu Ala Leu Asn Ala Val Gly
                20                  25                  30

Ala Glu Gly Gly Ala Ser Phe Ser Leu Pro Leu Pro Ile Ser Val Gly
            35                  40                  45

Arg Gly Leu Val Pro Val Leu Ser Leu Asn Tyr Ser Ser Thr Ala Gly
        50                  55                  60

Asn Gly Ser Phe Gly Met Gly Trp Gln Cys Gly Val Gly Phe Ile Ser
65                  70                  75                  80

Leu Arg Thr Ala Lys Gly Val Pro His Tyr Thr Gly Gln Asp Glu Tyr
                85                  90                  95

Leu Gly Pro Asp Gly Glu Val Leu Ser Ile Val Pro Asp Ser Gln Gly
            100                 105                 110

Gln Pro Glu Gln Arg Thr Ala Thr Ser Leu Leu Gly Thr Val Leu Thr
        115                 120                 125

Gln Pro His Thr Val Thr Arg Tyr Gln Ser Arg Val Ala Glu Lys Ile
    130                 135                 140

Val Arg Leu Glu His Trp Gln Pro Gln Gln Arg Arg Glu Glu Glu Thr
145                 150                 155                 160

Ser Phe Trp Val Leu Phe Thr Ala Asp Gly Leu Val His Leu Phe Gly
                165                 170                 175

Lys His His His Ala Arg Ile Ala Asp Pro Gln Asp Glu Thr Arg Ile
            180                 185                 190

Ala Arg Trp Leu Met Glu Glu Thr Val Thr His Thr Gly Glu His Ile
        195                 200                 205

Tyr Tyr His Tyr Arg Ala Glu Asp Asp Leu Asp Cys Asp Glu His Glu
    210                 215                 220

Leu Ala Gln His Ser Gly Val Thr Ala Gln Arg Tyr Leu Ala Lys Val
225                 230                 235                 240
```

-continued

```
Ser Tyr Gly Asn Thr Gln Pro Glu Thr Ala Phe Phe Ala Val Lys Ser
            245                 250                 255

Gly Ile Pro Ala Asp Asn Asp Trp Leu Phe His Leu Val Phe Asp Tyr
        260                 265                 270

Gly Glu Arg Ser Ser Leu Asn Ser Val Pro Glu Phe Asn Val Ser
            275                 280             285

Glu Asn Asn Val Ser Glu Asn Asn Val Pro Glu Lys Trp Arg Cys Arg
290                 295                 300

Pro Asp Ser Phe Ser Arg Tyr Glu Tyr Gly Phe Glu Ile Arg Thr Arg
305                 310                 315                 320

Arg Leu Cys Arg Gln Val Leu Met Phe His Gln Leu Lys Ala Leu Ala
                325                 330                 335

Gly Glu Lys Val Ala Glu Glu Thr Pro Ala Leu Val Ser Arg Leu Ile
            340                 345                 350

Leu Asp Tyr Asp Leu Asn Asn Lys Val Ser Leu Leu Gln Thr Ala Arg
        355                 360                 365

Arg Leu Ala His Glu Thr Asp Gly Thr Pro Val Met Met Ser Pro Leu
370                 375                 380

Glu Met Asp Tyr Gln Arg Val Asn His Gly Val Asn Leu Asn Trp Gln
385                 390                 395                 400

Ser Met Pro Gln Leu Glu Lys Met Asn Thr Leu Gln Pro Tyr Gln Leu
                405                 410                 415

Val Asp Leu Tyr Gly Glu Gly Ile Ser Gly Val Leu Tyr Gln Asp Thr
            420                 425                 430

Gln Lys Ala Trp Trp Tyr Arg Ala Pro Val Arg Asp Ile Thr Ala Glu
        435                 440                 445

Gly Thr Asn Ala Val Thr Tyr Glu Glu Ala Lys Pro Leu Pro His Ile
450                 455                 460

Pro Ala Gln Gln Glu Ser Ala Met Leu Leu Asp Ile Asn Gly Asp Gly
465                 470                 475                 480

Arg Leu Asp Trp Val Ile Thr Ala Ser Gly Leu Arg Gly Tyr His Thr
                485                 490                 495

Met Ser Pro Glu Gly Glu Trp Thr Pro Phe Ile Pro Leu Ser Ala Val
            500                 505                 510

Pro Met Glu Tyr Phe His Pro Gln Ala Lys Leu Ala Asp Ile Asp Gly
        515                 520                 525

Ala Gly Leu Pro Asp Leu Ala Leu Ile Gly Pro Asn Ser Val Arg Val
530                 535                 540

Trp Ser Asn Asn Arg Ala Gly Trp Asp Arg Ala Gln Asp Val Ile His
545                 550                 555                 560

Leu Ser Asp Met Pro Leu Pro Val Pro Gly Arg Asn Glu Arg His Leu
                565                 570                 575

Val Ala Phe Ser Asp Met Thr Gly Ser Gly Gln Ser His Leu Val Glu
            580                 585                 590

Val Thr Ala Asp Ser Val Arg Tyr Trp Pro Asn Leu Gly His Gly Lys
        595                 600                 605

Phe Gly Glu Pro Leu Met Met Thr Gly Phe Gln Ile Ser Gly Glu Thr
610                 615                 620

Phe Asn Pro Asp Arg Leu Tyr Met Val Asp Ile Asp Gly Ser Gly Thr
625                 630                 635                 640

Thr Asp Phe Ile Tyr Ala Arg Asn Thr Tyr Leu Glu Leu Tyr Ala Asn
                645                 650                 655

Glu Ser Gly Asn His Phe Ala Glu Pro Gln Arg Ile Asp Leu Pro Asp
```

-continued

```
            660                 665                 670
Gly Val Arg Phe Asp Asp Thr Cys Arg Leu Gln Ile Ala Asp Thr Gln
            675                 680                 685
Gly Leu Gly Thr Ala Ser Ile Ile Leu Thr Ile Pro His Met Lys Val
            690                 695                 700
Gln His Trp Arg Leu Asp Met Thr Ile Phe Lys Pro Trp Leu Leu Asn
705                 710                 715                 720
Ala Val Asn Asn Asn Met Gly Thr Glu Thr Thr Leu Tyr Tyr Arg Ser
                        725                 730                 735
Ser Ala Gln Phe Trp Leu Asp Glu Lys Leu Gln Ala Ser Glu Ser Gly
            740                 745                 750
Met Thr Val Val Ser Tyr Leu Pro Phe Pro Val His Val Leu Trp Arg
            755                 760                 765
Thr Glu Val Leu Asp Glu Ile Ser Gly Asn Arg Leu Thr Ser His Tyr
            770                 775                 780
His Tyr Ser His Gly Ala Trp Asp Gly Leu Arg Glu Phe Arg Gly
785                 790                 795                 800
Phe Gly Arg Val Thr Gln Thr Asp Ile Asp Ser Arg Ala Ser Ala Thr
            805                 810                 815
Gln Gly Thr His Ala Glu Pro Ala Pro Ser Arg Thr Val Asn Trp
            820                 825                 830
Tyr Gly Thr Gly Val Arg Glu Val Asp Ile Leu Leu Pro Thr Glu Tyr
            835                 840                 845
Trp Gln Gly Asp Gln Gln Ala Phe Pro His Phe Thr Pro Arg Phe Thr
            850                 855                 860
Arg Tyr Asp Glu Lys Ser Gly Gly Asp Met Thr Val Thr Pro Ser Glu
865                 870                 875                 880
Gln Glu Glu Tyr Trp Leu His Arg Ala Leu Lys Gly Gln Arg Leu Arg
                        885                 890                 895
Ser Glu Leu Tyr Gly Asp Asp Ser Ile Leu Ala Gly Thr Pro Tyr
            900                 905                 910
Ser Val Asp Glu Ser Arg Thr Gln Val Arg Leu Leu Pro Val Met Val
            915                 920                 925
Ser Asp Val Pro Ala Val Leu Val Ser Val Ala Glu Ser Arg Gln Tyr
930                 935                 940
Arg Tyr Glu Arg Val Ala Thr Asp Pro Gln Cys Ser Gln Lys Ile Val
945                 950                 955                 960
Leu Lys Ser Asp Ala Leu Gly Phe Pro Gln Asp Asn Leu Glu Ile Ala
                        965                 970                 975
Tyr Ser Arg Arg Pro Gln Pro Glu Phe Ser Pro Tyr Pro Asp Thr Leu
                        980                 985                 990
Pro Glu Thr Leu Phe Thr Ser Ser  Phe Asp Glu Gln Gln Met Phe Leu
            995                 1000                1005
Arg Leu  Thr Arg Gln Arg Ser  Ser Tyr His His Leu  Asn His Asp
            1010                1015                1020
Asp Asn  Thr Trp Ile Thr Gly  Leu Met Asp Thr Ser  Arg Ser Asp
            1025                1030                1035
Ala Arg  Ile Tyr Gln Ala Asp  Lys Val Pro Asp Gly  Gly Phe Ser
            1040                1045                1050
Leu Glu  Trp Phe Ser Ala Thr  Gly Ala Gly Ala Leu  Leu Leu Pro
            1055                1060                1065
Asp Ala  Ala Ala Asp Tyr Leu  Gly His Gln Arg Val  Ala Tyr Thr
            1070                1075                1080
```

```
Gly Pro Glu Glu Gln Pro Ala Ile Pro Pro Leu Val Ala Tyr Ile
    1085                1090                1095

Glu Thr Ala Glu Phe Asp Glu Arg Ser Leu Ala Ala Phe Glu Glu
    1100                1105                1110

Val Met Asp Glu Gln Glu Leu Thr Lys Gln Leu Asn Asp Ala Gly
    1115                1120                1125

Trp Asn Thr Ala Lys Val Pro Phe Ser Glu Lys Thr Asp Phe His
    1130                1135                1140

Val Trp Val Gly Gln Lys Glu Phe Thr Glu Tyr Ala Gly Ala Asp
    1145                1150                1155

Gly Phe Tyr Arg Pro Leu Val Gln Arg Glu Thr Lys Leu Thr Gly
    1160                1165                1170

Lys Thr Thr Val Thr Trp Asp Ser His Tyr Cys Val Ile Thr Ala
    1175                1180                1185

Thr Glu Asp Ala Ala Gly Leu Arg Met Gln Ala His Tyr Asp Tyr
    1190                1195                1200

Arg Phe Met Val Ala Asp Asn Thr Thr Asp Val Asn Asp Asn Tyr
    1205                1210                1215

His Thr Val Thr Phe Asp Ala Leu Gly Arg Val Thr Ser Phe Arg
    1220                1225                1230

Phe Trp Gly Thr Glu Asn Gly Glu Lys Gln Gly Tyr Thr Pro Ala
    1235                1240                1245

Glu Asn Glu Thr Val Pro Phe Ile Val Pro Thr Thr Val Asp Asp
    1250                1255                1260

Ala Leu Ala Leu Lys Pro Gly Ile Pro Val Ala Gly Leu Met Val
    1265                1270                1275

Tyr Ala Pro Leu Ser Trp Met Val Gln Ala Ser Phe Ser Asn Asp
    1280                1285                1290

Gly Glu Leu Tyr Gly Glu Leu Lys Pro Ala Gly Ile Ile Thr Glu
    1295                1300                1305

Asp Gly Tyr Leu Leu Ser Leu Ala Phe Arg Arg Trp Gln Gln Asn
    1310                1315                1320

Asn Pro Ala Ala Ala Met Pro Lys Gln Val Asn Ser Gln Asn Pro
    1325                1330                1335

Pro His Val Leu Ser Val Ile Thr Asp Arg Tyr Asp Ala Asp Pro
    1340                1345                1350

Glu Gln Gln Leu Arg Gln Thr Phe Thr Phe Ser Asp Gly Phe Gly
    1355                1360                1365

Arg Thr Leu Gln Thr Ala Val Arg His Glu Ser Gly Glu Ala Trp
    1370                1375                1380

Val Arg Asp Glu Tyr Gly Ala Ile Val Ala Glu Asn His Gly Ala
    1385                1390                1395

Pro Glu Thr Ala Met Thr Asp Phe Arg Trp Ala Val Ser Gly Arg
    1400                1405                1410

Thr Glu Tyr Asp Gly Lys Gly Gln Ala Leu Arg Lys Tyr Gln Pro
    1415                1420                1425

Tyr Phe Leu Asn Ser Trp Gln Tyr Val Ser Asp Ser Ala Arg
    1430                1435                1440

Gln Asp Ile Tyr Ala Asp Thr His Tyr Tyr Asp Pro Leu Gly Arg
    1445                1450                1455

Glu Tyr Gln Val Ile Thr Ala Lys Gly Gly Phe Arg Arg Ser Leu
    1460                1465                1470
```

```
Phe Thr Pro Trp Phe Val Val Asn Glu Asp Glu Asn  Asp Thr Ala
    1475                1480                1485
Gly Glu  Met Thr Ala
    1490
```

<210> SEQ ID NO 11
<211> LENGTH: 1506
<212> TYPE: PRT
<213> ORGANISM: Xenorhabdus bovienii

<400> SEQUENCE: 11

```
Met Lys Gln Asp Ser Gln Asp Met Thr Val Thr Gln Leu Ser Leu Pro
1               5                   10                  15

Lys Gly Gly Gly Ala Ile Ser Gly Met Gly Asp Thr Ile Ser Asn Ala
                20                  25                  30

Gly Pro Asp Gly Met Ala Ser Leu Ser Val Pro Leu Pro Ile Ser Ala
            35                  40                  45

Gly Arg Gly Gly Ala Pro Asn Leu Ser Leu Asn Tyr Ser Ser Gly Ala
        50                  55                  60

Gly Asn Gly Ser Phe Gly Ile Gly Trp Gln Ser Ser Thr Met Ala Ile
65                  70                  75                  80

Ser Arg Arg Thr Gln His Gly Val Pro Gln Tyr His Gly Glu Asp Thr
                85                  90                  95

Phe Leu Cys Pro Met Gly Glu Val Met Ala Val Ala Val Asn Gln Ser
            100                 105                 110

Gly Gln Pro Asp Val Arg Lys Thr Asp Lys Leu Leu Gly Gly Gln Leu
        115                 120                 125

Pro Val Thr Tyr Thr Val Thr Arg His Gln Pro Arg Asn Ile Gln His
130                 135                 140

Phe Ser Lys Leu Glu Tyr Trp Gln Pro Pro Thr Asp Val Glu Thr Thr
145                 150                 155                 160

Pro Phe Trp Leu Met Tyr Ser Pro Asp Gly Gln Ile His Ile Phe Gly
                165                 170                 175

Lys Thr Glu Gln Ala Gln Ile Ala Asn Pro Ala Glu Val Ser Gln Ile
            180                 185                 190

Ala Gln Trp Leu Leu Glu Glu Thr Val Thr Pro Ala Gly Glu His Ile
        195                 200                 205

Tyr Tyr Gln Tyr Arg Ala Glu Asp Ile Gly Cys Asp Asp Ser Glu
        210                 215                 220

Lys Asn Ala His Pro Asn Ala Ser Ala Gln Arg Tyr Leu Thr Gln Val
225                 230                 235                 240

Asn Tyr Gly Asn Ile Thr Pro Glu Ser Ser Leu Leu Val Leu Lys Asn
                245                 250                 255

Thr Pro Pro Ala Asp Asn Glu Trp Leu Phe His Leu Val Phe Asp Tyr
            260                 265                 270

Gly Glu Arg Ala Gln Glu Ile Asn Thr Val Pro Pro Phe Lys Ala Pro
        275                 280                 285

Ser Asn Asn Trp Lys Ile Arg Pro Asp Arg Phe Ser Arg Phe Glu Tyr
        290                 295                 300

Gly Phe Glu Val Arg Thr Arg Arg Leu Cys Gln Gln Ile Leu Met Phe
305                 310                 315                 320

His Arg Leu Lys Ser Leu Ala Gly Glu Gln Ile Asp Gly Glu Glu Ile
                325                 330                 335

Pro Ala Leu Val Ala Arg Leu Leu Leu Ser Tyr Asp Leu Asn Asp Ser
            340                 345                 350
```

-continued

```
Val Thr Thr Leu Thr Ala Ile Arg Gln Met Ala Tyr Glu Thr Asp Ala
        355                 360                 365
Thr Leu Ile Ala Leu Pro Pro Leu Glu Phe Asp Tyr Gln Pro Phe Glu
    370                 375                 380
Ala Lys Val Thr Gln Lys Trp Gln Glu Met Pro Gln Leu Ala Gly Leu
385                 390                 395                 400
Asn Ala Gln Gln Pro Tyr Gln Leu Val Asp Leu Tyr Gly Glu Gly Ile
                405                 410                 415
Ser Gly Ile Leu Tyr Gln Asp Arg Pro Gly Ala Trp Trp Tyr Gln Ala
            420                 425                 430
Pro Ile Arg Gln Lys Asn Val Glu Asp Ile Asn Ala Val Thr Tyr Ser
        435                 440                 445
Pro Ile Asn Pro Leu Pro Lys Ile Pro Ser Gln Gln Asp Arg Ala Thr
    450                 455                 460
Leu Met Asp Ile Asp Gly Asp Gly His Leu Asp Trp Val Ile Ala Gly
465                 470                 475                 480
Ala Gly Ile Gln Gly Arg Tyr Ser Met Gln Pro Asn Gly Glu Trp Thr
                485                 490                 495
His Phe Ile Pro Ile Ser Ala Leu Pro Thr Glu Tyr Phe His Pro Gln
            500                 505                 510
Ala Gln Leu Ala Asp Leu Val Gly Ala Gly Leu Ser Asp Leu Ala Leu
        515                 520                 525
Ile Gly Pro Arg Ser Val Arg Leu Tyr Ala Asn Asp Arg Gly Asn Trp
    530                 535                 540
Lys Ala Gly Ile Asn Val Met Pro Pro Asp Gly Val Asn Leu Pro Ile
545                 550                 555                 560
Phe Gly Gly Asp Ala Ser Ser Leu Val Ala Phe Ser Asp Met Leu Gly
                565                 570                 575
Ser Gly Gln Gln His Leu Val Glu Ile Ala Ala Gln Ser Val Lys Cys
            580                 585                 590
Trp Pro Asn Leu Gly His Gly Arg Phe Gly Ala Ala Ile Leu Leu Pro
        595                 600                 605
Gly Phe Ser Gln Pro Asn Gly Thr Phe Asn Ala Asn Gln Val Phe Leu
    610                 615                 620
Ala Asp Ile Asp Gly Ser Gly Thr Ala Asp Ile Ile Tyr Ala His Ser
625                 630                 635                 640
Thr Tyr Leu Asp Ile Tyr Leu Asn Glu Ser Gly Asn Arg Phe Ser Ala
                645                 650                 655
Pro Val Arg Leu Asn Leu Pro Glu Gly Val Met Phe Asp Asn Thr Cys
            660                 665                 670
Gln Leu Gln Val Ser Asp Ile Gln Gly Leu Gly Ala Ala Ser Ile Val
        675                 680                 685
Leu Thr Val Pro His Met Thr Pro Arg His Trp Arg Tyr Asp Phe Thr
    690                 695                 700
His Asn Lys Pro Trp Leu Leu Asn Val Ile Asn Asn Arg Gly Ala
705                 710                 715                 720
Glu Thr Thr Leu Phe Tyr Arg Ser Ser Ala Gln Phe Trp Leu Asp Glu
                725                 730                 735
Lys Ser Gln Ile Glu Glu Leu Gly Lys Phe Ala Ala Ser Tyr Leu Pro
            740                 745                 750
Phe Pro Ile His Leu Leu Trp Arg Asn Glu Ala Leu Asp Glu Ile Thr
        755                 760                 765
```

```
Gly Asn Arg Leu Thr Lys Val Met Asn Tyr Ala His Gly Ala Trp Asp
        770                 775                 780

Gly Arg Glu Arg Glu Phe Cys Gly Phe Gly Arg Val Thr Gln Ile Asp
785                 790                 795                 800

Thr Asp Glu Phe Ala Lys Gly Thr Thr Glu Lys Ala Pro Asp Glu Asn
            805                 810                 815

Ile Tyr Pro Ser Arg Ser Ile Ser Trp Phe Ala Thr Gly Leu Pro Glu
            820                 825                 830

Val Asp Ser Gln Leu Pro Ala Glu Tyr Trp Arg Gly Asp Asp Gln Ala
            835                 840                 845

Phe Ala Gly Phe Thr Pro Arg Phe Thr Arg Tyr Glu Lys Gly Asn Ala
    850                 855                 860

Gly Gln Glu Gly Gln Asp Thr Pro Ile Lys Glu Pro Thr Glu Thr Glu
865                 870                 875                 880

Ala Tyr Trp Leu Asn Arg Ala Met Lys Gly Gln Leu Leu Arg Ser Glu
                885                 890                 895

Val Tyr Gly Asp Asp Lys Thr Glu Lys Ala Lys Ile Pro Tyr Thr Val
            900                 905                 910

Thr Glu Ala Arg Cys Gln Val Arg Leu Ile Pro Ser Asn Asp Glu Ala
            915                 920                 925

Ala Pro Ser Ser Trp Thr Ser Ile Ile Glu Asn Arg Ser Tyr His Tyr
    930                 935                 940

Glu Arg Ile Val Val Asp Pro Ser Cys Lys Gln Gln Val Val Leu Lys
945                 950                 955                 960

Ala Asp Glu Tyr Gly Phe Pro Leu Ala Lys Val Asp Ile Ala Tyr Pro
                965                 970                 975

Arg Arg Asn Lys Pro Ala Gln Asn Pro Tyr Pro Asp Ser Leu Pro Asp
            980                 985                 990

Thr Leu Phe Ala Asp Ser Tyr Asp Asp Gln Gln Lys Gln Leu Tyr Leu
            995                 1000                1005

Thr Lys Gln Gln Gln Ser Tyr Tyr His Leu Thr Gln Gln Asp Asp
    1010                1015                1020

Trp Val Leu Gly Leu Thr Asp Ser Arg Tyr Ser Glu Val Tyr His
    1025                1030                1035

Tyr Ala Gln Thr Asp Ala Gln Ser Asp Ile Pro Lys Ala Gly Leu
    1040                1045                1050

Ile Leu Glu Asp Leu Leu Lys Val Asp Gly Leu Ile Gly Lys Asp
    1055                1060                1065

Lys Thr Phe Ile Tyr Leu Gly Gln Gln Arg Val Ala Tyr Val Gly
    1070                1075                1080

Gly Asp Ala Glu Lys Pro Thr Arg Gln Val Arg Val Ala Tyr Thr
    1085                1090                1095

Glu Thr Ala Ala Phe Asp Asp Asn Ala Leu His Ala Phe Asp Gly
    1100                1105                1110

Val Ile Ala Pro Asp Glu Leu Thr Gln Gln Leu Leu Ala Gly Gly
    1115                1120                1125

Tyr Leu Leu Val Pro Gln Ile Ser Asp Val Ala Gly Ser Ser Glu
    1130                1135                1140

Lys Val Trp Val Ala Arg Gln Gly Tyr Thr Glu Tyr Gly Ser Ala
    1145                1150                1155

Ala Gln Phe Tyr Arg Pro Leu Ile Gln Arg Lys Ser Leu Leu Thr
    1160                1165                1170

Gly Lys Tyr Thr Leu Ser Trp Asp Thr His Tyr Cys Val Val Val
```

```
             1175                1180                1185

Lys Thr Glu Asp Gly Ala Gly Met Thr Thr Gln Ala Lys Tyr Asp
    1190                1195                1200

Tyr Arg Phe Leu Leu Pro Ala Gln Leu Thr Asp Ile Asn Asp Asn
    1205                1210                1215

Gln His Ile Val Thr Phe Asn Ala Leu Gly Gln Val Thr Ser Ser
    1220                1225                1230

Arg Phe Trp Gly Thr Glu Asn Gly Lys Ile Ser Gly Tyr Ser Thr
    1235                1240                1245

Pro Glu Ser Lys Pro Phe Thr Val Pro Asp Thr Val Glu Lys Ala
    1250                1255                1260

Leu Ala Leu Gln Pro Thr Ile Pro Val Ser Gln Cys Asn Ile Tyr
    1265                1270                1275

Val Pro Asp Ser Trp Met Arg Leu Leu Pro Gln Gln Ser Leu Thr
    1280                1285                1290

Gly Gln Leu Lys Glu Gly Glu Thr Leu Trp Asn Ala Leu His Arg
    1295                1300                1305

Ala Gly Val Val Thr Glu Asp Gly Leu Ile Cys Glu Leu Ala Tyr
    1310                1315                1320

Arg Arg Trp Ile Lys Arg Gln Ala Thr Ser Ser Met Met Ala Val
    1325                1330                1335

Thr Leu Gln Gln Ile Leu Ala Gln Thr Pro Arg Gln Pro Pro His
    1340                1345                1350

Ala Met Thr Ile Thr Thr Asp Arg Tyr Asp Ser Asp Ser Gln Gln
    1355                1360                1365

Gln Leu Arg Gln Ser Ile Val Leu Ser Asp Gly Phe Gly Arg Val
    1370                1375                1380

Leu Gln Ser Ala Gln Arg His Glu Ala Gly Glu Ala Trp Gln Arg
    1385                1390                1395

Ala Glu Asp Gly Ser Leu Val Val Asp Asn Thr Gly Lys Pro Val
    1400                1405                1410

Val Ala Asn Thr Thr Thr Arg Trp Ala Val Ser Gly Arg Thr Glu
    1415                1420                1425

Tyr Asp Gly Lys Gly Gln Ala Ile Arg Ala Tyr Leu Pro Tyr Tyr
    1430                1435                1440

Leu Asn Asp Trp Arg Tyr Val Ser Asp Ser Ala Arg Asp Asp
    1445                1450                1455

Leu Tyr Ala Asp Thr His Phe Tyr Asp Pro Leu Gly Arg Glu Tyr
    1460                1465                1470

Gln Val Lys Thr Ala Lys Gly Phe Trp Arg Glu Asn Met Phe Met
    1475                1480                1485

Pro Trp Phe Val Val Asn Glu Asp Glu Asn Asp Thr Ala Ala Arg
    1490                1495                1500

Leu Thr Ser
    1505

<210> SEQ ID NO 12
<211> LENGTH: 1444
<212> TYPE: PRT
<213> ORGANISM: Paenibacillus strain DAS1529

<400> SEQUENCE: 12

Met Pro Gln Ser Ser Asn Ala Asp Ile Lys Leu Leu Ser Pro Ser Leu
1               5                   10                  15
```

```
Pro Lys Gly Gly Gly Ser Met Lys Gly Ile Glu Glu Asn Ile Ala Ala
             20                  25                  30
Pro Gly Ser Asp Gly Met Ala Arg Cys Asn Val Pro Leu Pro Val Thr
         35                  40                  45
Ser Gly Arg Tyr Ile Thr Pro Asp Ile Ser Leu Ser Tyr Ala Ser Gly
 50                  55                  60
His Gly Asn Gly Ala Tyr Gly Met Gly Trp Thr Met Gly Val Met Ser
 65                  70                  75                  80
Ile Ser Arg Arg Thr Ser Arg Gly Thr Pro Ser Tyr Thr Ser Glu Asp
                 85                  90                  95
Gln Phe Leu Gly Pro Asp Gly Glu Val Leu Val Pro Glu Ser Asn Glu
             100                 105                 110
Gln Gly Glu Ile Ile Thr Arg His Thr Asp Thr Ala Gln Gly Ile Pro
         115                 120                 125
Leu Gly Glu Thr Phe Thr Val Thr Arg Tyr Phe Pro Arg Ile Glu Ser
130                 135                 140
Ala Phe His Leu Leu Glu Tyr Trp Glu Ala Gln Ala Gly Ser Ala Thr
145                 150                 155                 160
Ala Ser Phe Trp Leu Ile His Ser Ala Asp Gly Val Leu His Cys Leu
                 165                 170                 175
Gly Lys Thr Ala Gln Ala Arg Ile Ala Ala Pro Asp Asp Ser Ala Lys
             180                 185                 190
Ile Ala Glu Trp Leu Val Glu Ser Val Ser Pro Phe Gly Glu His
         195                 200                 205
Ile Tyr Tyr Gln Tyr Lys Glu Glu Asp Asn Gln Gly Val Asn Leu Glu
210                 215                 220
Glu Asp Asn His Gln Tyr Gly Ala Asn Arg Tyr Leu Lys Ser Ile Arg
225                 230                 235                 240
Tyr Gly Asn Lys Val Ala Ser Pro Ser Leu Tyr Val Trp Lys Gly Glu
                 245                 250                 255
Ile Pro Ala Asp Gly Gln Trp Leu Tyr Ser Val Ile Leu Asp Tyr Gly
             260                 265                 270
Glu Asn Asp Thr Ser Ala Asp Val Pro Pro Leu Tyr Thr Pro Gln Gly
             275                 280                 285
Glu Trp Leu Val Arg Pro Asp Arg Phe Ser Arg Tyr Asp Tyr Gly Phe
290                 295                 300
Glu Val Arg Thr Cys Arg Leu Cys Arg Gln Val Leu Met Phe His Val
305                 310                 315                 320
Phe Lys Glu Leu Gly Gly Glu Pro Ala Leu Val Trp Arg Met Gln Leu
                 325                 330                 335
Glu Tyr Asp Glu Asn Pro Ala Ala Ser Met Leu Ser Ala Val Arg Gln
             340                 345                 350
Leu Ala Tyr Glu Ala Asp Gly Ala Ile Arg Ser Leu Pro Pro Leu Glu
             355                 360                 365
Phe Asp Tyr Thr Pro Phe Gly Ile Glu Thr Thr Ala Asp Trp Gln Pro
         370                 375                 380
Phe Leu Pro Val Pro Glu Trp Ala Asp Glu His Tyr Gln Leu Val
385                 390                 395                 400
Asp Leu Tyr Gly Glu Gly Ile Pro Gly Leu Leu Tyr Gln Asn Asn Asp
                 405                 410                 415
His Trp His Tyr Arg Ser Pro Ala Arg Gly Asp Thr Pro Asp Gly Ile
                 420                 425                 430
Ala Tyr Asn Ser Trp Arg Pro Leu Pro His Ile Pro Val Asn Ser Arg
```

-continued

```
                435                 440                 445
Asn Gly Met Leu Met Asp Leu Asn Gly Asp Gly Tyr Leu Glu Trp Leu
    450                 455                 460
Leu Ala Glu Pro Gly Val Ala Gly Arg Tyr Ser Met Asn Pro Asp Lys
465                 470                 475                 480
Ser Trp Ser Gly Phe Val Pro Leu Gln Ala Leu Pro Thr Glu Phe Phe
                485                 490                 495
His Pro Gln Ala Gln Leu Ala Asn Val Thr Gly Ser Gly Leu Thr Asp
            500                 505                 510
Leu Val Met Ile Gly Pro Lys Ser Val Arg Phe Tyr Ala Gly Glu Glu
        515                 520                 525
Ala Gly Phe Lys Arg Ala Cys Glu Val Trp Gln Gln Val Gly Ile Thr
    530                 535                 540
Leu Pro Val Glu Arg Val Asp Lys Lys Glu Leu Val Ala Phe Ser Asp
545                 550                 555                 560
Met Leu Gly Ser Gly Gln Ser His Leu Val Arg Ile Arg His Asp Gly
                565                 570                 575
Val Thr Cys Trp Pro Asn Leu Gly Asn Gly Val Phe Gly Ala Pro Leu
            580                 585                 590
Ala Leu His Gly Phe Thr Ala Ser Glu Arg Glu Phe Asn Pro Glu Arg
        595                 600                 605
Val Tyr Leu Val Asp Leu Asp Gly Ser Gly Ala Ser Asp Ile Ile Tyr
    610                 615                 620
Ala Ser Arg Asp Ala Leu Leu Ile Tyr Arg Asn Leu Ser Gly Asn Gly
625                 630                 635                 640
Phe Ala Asp Pro Val Arg Val Pro Leu Pro Asp Gly Val Arg Phe Asp
                645                 650                 655
Asn Leu Cys Arg Leu Leu Pro Ala Asp Ile Arg Gly Leu Gly Val Ala
            660                 665                 670
Ser Leu Val Leu His Val Pro Tyr Met Ala Pro Arg Ser Trp Lys Leu
        675                 680                 685
Asp Phe Phe Ala Ala Lys Pro Tyr Leu Leu Gln Thr Val Ser Asn Asn
    690                 695                 700
Leu Gly Ala Ser Ser Phe Trp Tyr Arg Ser Thr Gln Tyr Trp
705                 710                 715                 720
Leu Asp Glu Lys Gln Ala Ala Ser Ser Ala Val Ser Ala Leu Pro Phe
                725                 730                 735
Pro Ile Asn Val Val Ser Asp Met His Thr Val Asp Glu Ile Ser Gly
            740                 745                 750
Arg Thr Arg Thr Gln Lys Tyr Thr Tyr Arg His Gly Val Tyr Asp Arg
        755                 760                 765
Thr Glu Lys Glu Phe Ala Gly Phe Gly Arg Ile Asp Thr Trp Glu Glu
    770                 775                 780
Glu Arg Asp Ser Glu Gly Thr Leu Ser Val Ser Thr Pro Pro Val Leu
785                 790                 795                 800
Thr Arg Thr Trp Tyr His Thr Gly Gln Lys Gln Asp Glu Glu Arg Ala
                805                 810                 815
Val Gln Gln Tyr Trp Gln Gly Asp Pro Ala Ala Phe Gln Val Lys Pro
            820                 825                 830
Val Arg Leu Thr Arg Phe Asp Ala Ala Ala Gln Asp Leu Pro Leu
        835                 840                 845
Asp Ser Asn Asn Gly Gln Gln Glu Tyr Trp Leu Tyr Arg Ser Leu Gln
    850                 855                 860
```

```
Gly Met Pro Leu Arg Thr Glu Ile Phe Ala Gly Asp Val Gly Gly Ser
865                 870                 875                 880

Pro Pro Tyr Gln Val Glu Ser Phe Arg Tyr Gln Val Arg Leu Val Gln
                885                 890                 895

Ser Ile Asp Ser Glu Cys Val Ala Leu Pro Met Gln Leu Glu Gln Leu
            900                 905                 910

Thr Tyr Asn Tyr Glu Gln Ile Ala Ser Asp Pro Gln Cys Ser Gln Gln
        915                 920                 925

Ile Gln Gln Trp Phe Asp Glu Tyr Gly Val Ala Ala Gln Ser Val Thr
    930                 935                 940

Ile Gln Tyr Pro Arg Arg Ala Gln Pro Glu Asp Asn Pro Tyr Pro Arg
945                 950                 955                 960

Thr Leu Pro Asp Thr Ser Trp Ser Ser Ser Tyr Asp Ser Gln Gln Met
                965                 970                 975

Leu Leu Arg Leu Thr Arg Gln Arg Gln Lys Ala Tyr His Leu Ala Asp
            980                 985                 990

Pro Glu Gly Trp Arg Leu Asn Ile Pro His Gln Thr Arg Leu Asp Ala
        995                 1000                1005

Phe Ile Tyr Ser Ala Asp Ser Val Pro Ala Glu Gly Ile Ser Ala
    1010                1015                1020

Glu Leu Leu Glu Val Asp Gly Thr Leu Arg Ser Ser Ala Leu Glu
    1025                1030                1035

Gln Ala Tyr Gly Gly Gln Ser Glu Ile Ile Tyr Ala Gly Gly Gly
    1040                1045                1050

Glu Pro Asp Leu Arg Ala Leu Val His Tyr Thr Arg Ser Ala Val
    1055                1060                1065

Leu Asp Glu Asp Cys Leu Gln Ala Tyr Glu Gly Val Leu Ser Asp
    1070                1075                1080

Ser Gln Leu Asn Ser Leu Leu Ala Ser Ser Gly Tyr Gln Arg Ser
    1085                1090                1095

Ala Arg Ile Leu Gly Ser Gly Asp Glu Val Asp Ile Phe Val Ala
    1100                1105                1110

Glu Gln Gly Phe Thr Arg Tyr Ala Asp Glu Pro Asn Phe Phe Arg
    1115                1120                1125

Ile Leu Gly Gln Gln Ser Ser Leu Leu Ser Gly Glu Gln Val Leu
    1130                1135                1140

Thr Trp Asp Asp Asn Phe Cys Ala Val Thr Ser Ile Glu Asp Ala
    1145                1150                1155

Leu Gly Asn Gln Ile Gln Ile Ala Tyr Asp Tyr Arg Phe Val Glu
    1160                1165                1170

Ala Ile Gln Ile Thr Asp Thr Asn Asn Asn Val Asn Gln Val Ala
    1175                1180                1185

Leu Asp Ala Leu Gly Arg Val Val Tyr Ser Arg Thr Trp Gly Thr
    1190                1195                1200

Glu Glu Gly Ile Lys Thr Gly Phe Arg Pro Glu Val Glu Phe Ala
    1205                1210                1215

Thr Pro Glu Thr Met Glu Gln Ala Leu Ala Leu Ala Ser Pro Leu
    1220                1225                1230

Pro Val Ala Ser Cys Cys Val Tyr Asp Ala His Ser Trp Met Gly
    1235                1240                1245

Thr Ile Thr Leu Ala Gln Leu Ser Glu Leu Val Pro Asp Ser Glu
    1250                1255                1260
```

-continued

```
Lys Gln Trp Ser Phe Leu Ile Asp Asn Arg Leu Ile Met Pro Asp
    1265                1270                1275

Gly Arg Ile Arg Ser Arg Gly Arg Asp Pro Trp Ser Leu His Arg
    1280                1285                1290

Leu Leu Pro Pro Ala Val Gly Glu Leu Leu Ser Glu Ala Asp Arg
    1295                1300                1305

Lys Pro Pro His Thr Val Ile Leu Ala Ala Asp Arg Tyr Pro Asp
    1310                1315                1320

Asp Pro Ser Gln Gln Ile Gln Ala Ser Ile Val Phe Ser Asp Gly
    1325                1330                1335

Phe Gly Arg Thr Ile Gln Thr Ala Lys Arg Glu Asp Thr Arg Trp
    1340                1345                1350

Ala Ile Ala Glu Arg Val Asp Tyr Asp Gly Thr Gly Ala Val Ile
    1355                1360                1365

Arg Ser Phe Gln Pro Phe Tyr Leu Asp Asp Trp Asn Tyr Val Gly
    1370                1375                1380

Glu Glu Ala Val Ser Ser Ser Met Tyr Ala Thr Ile Tyr Tyr Tyr
    1385                1390                1395

Asp Ala Leu Ala Arg Gln Leu Arg Met Val Asn Ala Lys Gly Tyr
    1400                1405                1410

Glu Arg Arg Thr Ala Phe Tyr Pro Trp Phe Thr Val Asn Glu Asp
    1415                1420                1425

Glu Asn Asp Thr Met Asp Ser Ser Leu Phe Ala Ser Pro Pro Ala
    1430                1435                1440

Arg

<210> SEQ ID NO 13
<211> LENGTH: 1428
<212> TYPE: PRT
<213> ORGANISM: Serratia entomophila

<400> SEQUENCE: 13

Met Gln Asn His Gln Asp Met Ala Ile Thr Ala Pro Thr Leu Pro Ser
1               5                   10                  15

Gly Gly Gly Ala Val Thr Gly Leu Lys Gly Asp Ile Ala Ala Gly
                20                  25                  30

Pro Asp Gly Ala Ala Thr Leu Ser Ile Pro Leu Pro Val Ser Pro Gly
        35                  40                  45

Arg Gly Tyr Ala Pro Thr Gly Ala Leu Asn Tyr His Ser Arg Ser Gly
    50                  55                  60

Asn Gly Pro Phe Gly Ile Gly Trp Gly Ile Gly Gly Ala Ala Val Gln
65                  70                  75                  80

Arg Arg Thr Arg Asn Gly Ala Pro Thr Tyr Asp Thr Asp Glu Phe
                85                  90                  95

Thr Gly Pro Asp Gly Glu Val Leu Val Pro Ala Leu Thr Ala Ala Gly
            100                 105                 110

Thr Gln Glu Ala Arg Gln Ala Thr Ser Leu Leu Gly Ile Asn Pro Gly
        115                 120                 125

Gly Ser Phe Asn Val Gln Val Tyr Arg Ser Arg Thr Glu Gly Ser Leu
    130                 135                 140

Ser Arg Leu Glu Arg Trp Leu Pro Ala Asp Thr Glu Thr Glu Phe
145                 150                 155                 160

Trp Val Leu Tyr Thr Pro Asp Gly Gln Val Ala Leu Leu Gly Arg Asn
                165                 170                 175
```

-continued

```
Ala Gln Ala Arg Ile Ser Asn Pro Thr Ala Pro Thr Gln Thr Ala Val
            180                 185                 190
Trp Leu Met Glu Ser Ser Val Ser Leu Thr Gly Glu Gln Met Tyr Tyr
        195                 200                 205
Gln Tyr Arg Ala Glu Asp Asp Gly Cys Asp Glu Ala Glu Arg Asp
    210                 215                 220
Ala His Pro Gln Ala Gly Ala Gln Arg Tyr Pro Val Ala Val Trp Tyr
225                 230                 235                 240
Gly Asn Arg Gln Ala Ala Arg Thr Leu Pro Ala Leu Val Ser Thr Pro
                245                 250                 255
Ser Met Asp Ser Trp Leu Phe Ile Leu Val Phe Asp Tyr Gly Glu Arg
            260                 265                 270
Ser Ser Val Leu Ser Glu Ala Pro Ala Trp Gln Thr Pro Gly Ser Gly
        275                 280                 285
Glu Trp Leu Cys Arg Gln Asp Cys Phe Ser Gly Tyr Glu Phe Gly Phe
    290                 295                 300
Asn Leu Arg Thr Arg Arg Leu Cys Arg Gln Val Leu Met Phe His Tyr
305                 310                 315                 320
Leu Gly Val Leu Ala Gly Ser Ser Gly Ala Asn Asp Ala Pro Ala Leu
                325                 330                 335
Ile Ser Arg Leu Leu Leu Asp Tyr Arg Glu Ser Pro Ser Leu Ser Leu
            340                 345                 350
Leu Glu Asn Val His Gln Val Ala Tyr Glu Ser Asp Gly Thr Ser Cys
        355                 360                 365
Ala Leu Pro Ala Leu Ala Leu Gly Trp Gln Thr Phe Thr Pro Pro Thr
    370                 375                 380
Leu Ser Ala Trp Gln Thr Arg Asp Asp Met Gly Lys Leu Ser Leu Leu
385                 390                 395                 400
Gln Pro Tyr Gln Leu Val Asp Leu Asn Gly Glu Gly Val Val Gly Ile
                405                 410                 415
Leu Tyr Gln Asp Ser Gly Ala Trp Trp Tyr Arg Glu Pro Val Arg Gln
            420                 425                 430
Ser Gly Asp Asp Pro Asp Ala Val Thr Trp Gly Ala Ala Ala Leu
        435                 440                 445
Pro Thr Met Pro Ala Leu His Asn Ser Gly Ile Leu Ala Asp Leu Asn
    450                 455                 460
Gly Asp Gly Arg Leu Glu Trp Val Val Thr Ala Pro Gly Val Ala Gly
465                 470                 475                 480
Met Tyr Asp Arg Thr Pro Gly Arg Asp Trp Leu His Phe Thr Pro Leu
                485                 490                 495
Ser Ala Leu Pro Val Glu Tyr Ala His Pro Lys Ala Val Leu Ala Asp
            500                 505                 510
Ile Leu Gly Ala Gly Leu Thr Asp Met Val Leu Ile Gly Pro Arg Ser
        515                 520                 525
Val Arg Leu Tyr Ser Gly Lys Asn Asp Gly Trp Asn Lys Gly Glu Thr
    530                 535                 540
Val Gln Gln Thr Glu Arg Leu Thr Leu Pro Val Pro Gly Val Asp Pro
545                 550                 555                 560
Arg Thr Leu Val Ala Phe Ser Asp Met Ala Gly Ser Gly Gln Gln His
                565                 570                 575
Leu Thr Glu Val Arg Ala Asn Gly Val Arg Tyr Trp Pro Asn Leu Gly
            580                 585                 590
His Gly Arg Phe Gly Gln Pro Val Asn Ile Pro Gly Phe Ser Gln Ser
```

-continued

```
                595                 600                 605
Val Thr Thr Phe Asn Pro Asp Gln Ile Leu Leu Ala Asp Thr Asp Gly
610                 615                 620

Ser Gly Thr Thr Asp Leu Ile Tyr Ala Met Ser Asp Arg Leu Val Ile
625                 630                 635                 640

Tyr Phe Asn Gln Ser Gly Asn Tyr Phe Ala Glu Pro His Thr Leu Leu
                645                 650                 655

Leu Pro Lys Gly Val Arg Tyr Asp Arg Thr Cys Ser Leu Gln Val Ala
                660                 665                 670

Asp Ile Gln Gly Leu Gly Val Pro Ser Leu Leu Leu Thr Val Pro His
                675                 680                 685

Val Ala Pro His His Trp Val Cys His Leu Ser Ala Asp Lys Pro Trp
690                 695                 700

Leu Leu Asn Gly Met Asn Asn Met Gly Ala Arg His Ala Leu His
705                 710                 715                 720

Tyr Arg Ser Ser Val Gln Phe Trp Leu Asp Glu Lys Ala Glu Ala Leu
                725                 730                 735

Ala Ala Gly Ser Ser Pro Ala Cys Tyr Leu Pro Phe Thr Leu His Thr
                740                 745                 750

Leu Trp Arg Ser Val Val Gln Asp Glu Ile Thr Gly Asn Arg Leu Val
                755                 760                 765

Ser Asp Val Leu Tyr Arg His Gly Val Trp Asp Gly Gln Glu Arg Glu
                770                 775                 780

Phe Arg Gly Phe Gly Phe Val Glu Ile Arg Asp Thr Asp Thr Leu Ala
785                 790                 795                 800

Ser Gln Gly Thr Ala Thr Glu Leu Ser Met Pro Ser Val Ser Arg Asn
                805                 810                 815

Trp Tyr Ala Thr Gly Val Pro Ala Val Asp Glu Arg Leu Pro Glu Thr
                820                 825                 830

Tyr Trp Gln Asn Asp Ala Ala Ala Phe Ala Asp Phe Ala Thr Arg Phe
                835                 840                 845

Thr Val Gly Ser Gly Glu Asp Glu Gln Thr Tyr Thr Pro Asp Asp Ser
850                 855                 860

Lys Thr Phe Trp Leu Gln Arg Ala Leu Lys Gly Ile Leu Leu Arg Ser
865                 870                 875                 880

Glu Leu Tyr Gly Ala Asp Gly Ser Ser Gln Ala Asp Ile Pro Tyr Ser
                885                 890                 895

Val Thr Glu Ser Arg Pro Gln Val Arg Leu Val Glu Ala Asn Gly Asp
                900                 905                 910

Tyr Pro Val Val Trp Pro Met Gly Ala Glu Ser Arg Thr Ser Val Tyr
                915                 920                 925

Glu Arg Tyr His Asn Asp Pro Gln Cys Gln Gln Gln Ala Val Leu Leu
                930                 935                 940

Ser Asp Glu Tyr Gly Phe Pro Leu Arg Gln Val Ser Val Asn Tyr Pro
945                 950                 955                 960

Arg Arg Pro Pro Ser Ala Asp Asn Pro Tyr Pro Ala Ser Leu Pro Ala
                965                 970                 975

Thr Leu Phe Ala Asn Ser Tyr Asp Glu Gln Gln Gln Ile Leu Arg Leu
                980                 985                 990

Gly Leu Gln Gln Ser Ser Ala His  His Leu Val Ser Leu  Ser Glu Gly
           995                 1000                1005

His Trp  Leu Leu Gly Leu Ala  Glu Ala Ser Arg Asp  Asp Val Phe
      1010                1015                1020
```

-continued

```
Thr Tyr Ser Ala Asp Asn Val Pro Glu Gly Gly Leu Thr Leu Glu
    1025                1030                1035

His Leu Leu Ala Pro Glu Ser Leu Val Ser Asp Ser Gln Val Gly
    1040                1045                1050

Thr Leu Ala Gly Gln Gln Gln Val Trp Tyr Leu Asp Ser Gln Asp
    1055                1060                1065

Val Ala Thr Val Ala Ala Pro Pro Leu Pro Pro Lys Val Ala Phe
    1070                1075                1080

Ile Glu Thr Ala Val Leu Asp Glu Gly Met Val Ser Ser Leu Ala
    1085                1090                1095

Ala Tyr Ile Val Asp Glu His Leu Glu Gln Ala Gly Tyr Arg Gln
    1100                1105                1110

Ser Gly Tyr Leu Phe Pro Arg Gly Arg Glu Ala Glu Gln Ala Leu
    1115                1120                1125

Trp Thr Gln Cys Gln Gly Tyr Val Thr Tyr Ala Gly Ala Glu His
    1130                1135                1140

Phe Trp Leu Pro Leu Ser Phe Arg Asp Ser Met Leu Thr Gly Pro
    1145                1150                1155

Val Thr Val Thr Arg Asp Ala Tyr Asp Cys Val Ile Thr Gln Trp
    1160                1165                1170

Gln Asp Ala Ala Gly Ile Val Thr Thr Ala Asp Tyr Asp Trp Arg
    1175                1180                1185

Phe Leu Thr Pro Val Arg Val Thr Asp Pro Asn Asp Asn Leu Gln
    1190                1195                1200

Ser Val Thr Leu Asp Ala Leu Gly Arg Val Thr Thr Leu Arg Phe
    1205                1210                1215

Trp Gly Thr Glu Asn Gly Ile Ala Thr Gly Tyr Ser Asp Ala Thr
    1220                1225                1230

Leu Ser Val Pro Asp Gly Ala Ala Ala Leu Ala Leu Thr Ala
    1235                1240                1245

Pro Leu Pro Val Ala Gln Cys Leu Val Tyr Val Thr Asp Ser Trp
    1250                1255                1260

Gly Asp Asp Asp Asn Glu Lys Met Pro Pro His Val Val Val Leu
    1265                1270                1275

Ala Thr Asp Arg Tyr Asp Ser Asp Thr Gly Gln Gln Val Arg Gln
    1280                1285                1290

Gln Val Thr Phe Ser Asp Gly Phe Gly Arg Glu Leu Gln Ser Ala
    1295                1300                1305

Thr Arg Gln Ala Glu Gly Asn Ala Trp Gln Arg Gly Arg Asp Gly
    1310                1315                1320

Lys Leu Val Thr Ala Ser Asp Gly Leu Pro Val Thr Val Ala Thr
    1325                1330                1335

Asn Phe Arg Trp Ala Val Thr Gly Arg Ala Glu Tyr Asp Asn Lys
    1340                1345                1350

Gly Leu Pro Val Arg Val Tyr Gln Pro Tyr Phe Leu Asp Ser Trp
    1355                1360                1365

Gln Tyr Val Ser Asp Asp Ser Ala Arg Gln Asp Leu Tyr Ala Asp
    1370                1375                1380

Thr His Phe Tyr Asp Pro Thr Ala Arg Glu Trp Gln Val Ile Thr
    1385                1390                1395

Ala Lys Gly Glu Arg Arg Gln Val Leu Tyr Thr Pro Trp Phe Val
    1400                1405                1410
```

Val Ser  Glu Asp Glu Asn Asp  Thr Val Gly Leu Asn  Asp Ala Ser
    1415             1420               1425

<210> SEQ ID NO 14
<211> LENGTH: 3132
<212> TYPE: DNA
<213> ORGANISM: Photorhabdus luminescens
<220> FEATURE:
<221> NAME/KEY: exon
<222> LOCATION: (1)..(3132)

<400> SEQUENCE: 14

| | |
|---|---|
| atg agt ccg tct gag act act ctt tat act caa acc cca aca gtc agc<br>Met Ser Pro Ser Glu Thr Thr Leu Tyr Thr Gln Thr Pro Thr Val Ser<br>1               5                   10                  15 | 48 |
| gtg tta gat aat cgc ggt ctg tcc att cgt gat att ggt ttt cac cgt<br>Val Leu Asp Asn Arg Gly Leu Ser Ile Arg Asp Ile Gly Phe His Arg<br>            20                  25                  30 | 96 |
| att gta atc ggg ggg gat act gac acc cgc gtc acc cgt cac cag tat<br>Ile Val Ile Gly Gly Asp Thr Asp Thr Arg Val Thr Arg His Gln Tyr<br>        35                  40                  45 | 144 |
| gat gcc cgt gga cac ctg aac tac agt att gac cca cgc ttg tat gat<br>Asp Ala Arg Gly His Leu Asn Tyr Ser Ile Asp Pro Arg Leu Tyr Asp<br>    50                  55                  60 | 192 |
| gca aag cag gct gat aac tca gta aag cct aat ttt gtc tgg cag cat<br>Ala Lys Gln Ala Asp Asn Ser Val Lys Pro Asn Phe Val Trp Gln His<br>65                  70                  75                  80 | 240 |
| gat ctg gcc ggt cat gcc ctg cgg aca gag agt gtc gat gct ggt cgt<br>Asp Leu Ala Gly His Ala Leu Arg Thr Glu Ser Val Asp Ala Gly Arg<br>                85                  90                  95 | 288 |
| act gtt gca ttg aat gat att gaa ggt cgt tcg gta atg aca atg aat<br>Thr Val Ala Leu Asn Asp Ile Glu Gly Arg Ser Val Met Thr Met Asn<br>            100                 105                 110 | 336 |
| gcg acc ggt gtt cgt cag acc cgt cgc tat gaa ggc aac acc ttg ccc<br>Ala Thr Gly Val Arg Gln Thr Arg Arg Tyr Glu Gly Asn Thr Leu Pro<br>        115                 120                 125 | 384 |
| ggt cgc ttg tta tct gtg agc gag caa gtt ttc aac caa gag agt gct<br>Gly Arg Leu Leu Ser Val Ser Glu Gln Val Phe Asn Gln Glu Ser Ala<br>    130                 135                 140 | 432 |
| aaa gtg aca gag cgc ttt atc tgg gct ggg aat aca acc tcg gag aaa<br>Lys Val Thr Glu Arg Phe Ile Trp Ala Gly Asn Thr Thr Ser Glu Lys<br>145                 150                 155                 160 | 480 |
| gag tat aac ctc tcc ggt ctg tgt ata cgc cac tac gac aca gcg gga<br>Glu Tyr Asn Leu Ser Gly Leu Cys Ile Arg His Tyr Asp Thr Ala Gly<br>                165                 170                 175 | 528 |
| gtg acc cgg ttg atg agt cag tca ctg gcg ggc gcc atg cta tcc caa<br>Val Thr Arg Leu Met Ser Gln Ser Leu Ala Gly Ala Met Leu Ser Gln<br>            180                 185                 190 | 576 |
| tct cac caa ttg ctg gcg gaa ggg cag gag gct aac tgg agc ggt gac<br>Ser His Gln Leu Leu Ala Glu Gly Gln Glu Ala Asn Trp Ser Gly Asp<br>        195                 200                 205 | 624 |
| gac gaa act gtc tgg cag gga atg ctg gca agt gag gtc tat acg aca<br>Asp Glu Thr Val Trp Gln Gly Met Leu Ala Ser Glu Val Tyr Thr Thr<br>    210                 215                 220 | 672 |
| caa agt acc act aat gcc atc ggg gct tta ctg acc caa acc gat gcg<br>Gln Ser Thr Thr Asn Ala Ile Gly Ala Leu Leu Thr Gln Thr Asp Ala<br>225                 230                 235                 240 | 720 |
| aaa ggc aat att cag cgt ctg gct tat gac att gcc ggt cag tta aaa<br>Lys Gly Asn Ile Gln Arg Leu Ala Tyr Asp Ile Ala Gly Gln Leu Lys<br>                245                 250                 255 | 768 |
| ggg agt tgg ttg acg gtg aaa ggc cag agt gaa cag gtg att gtt aag<br> | 816 |

```
Gly Ser Trp Leu Thr Val Lys Gly Gln Ser Glu Gln Val Ile Val Lys
            260                 265                 270 tcc ctg agc tgg tca gcc gca ggt cat aaa ttg cgt gaa gag cac ggt      864
Ser Leu Ser Trp Ser Ala Ala Gly His Lys Leu Arg Glu Glu His Gly
        275                 280                 285 aac ggc gtg gtt acg gag tac agt tat gag ccg gaa act caa cgt ctg      912
Asn Gly Val Val Thr Glu Tyr Ser Tyr Glu Pro Glu Thr Gln Arg Leu
    290                 295                 300 ata ggt atc acc acc cgg cgt gcc gaa ggg agt caa tca gga gcc aga      960
Ile Gly Ile Thr Thr Arg Arg Ala Glu Gly Ser Gln Ser Gly Ala Arg
305                 310                 315                 320 gta ttg cag gat cta cgc tat aag tat gat ccg gtg ggg aat gtt atc     1008
Val Leu Gln Asp Leu Arg Tyr Lys Tyr Asp Pro Val Gly Asn Val Ile
            325                 330                 335 agt atc cat aat gat gcc gaa gct acc cgc ttt tgg cgt aat cag aaa     1056
Ser Ile His Asn Asp Ala Glu Ala Thr Arg Phe Trp Arg Asn Gln Lys
        340                 345                 350 gtg gag ccg gag aat cgc tat gtt tat gat tct ctg tat cag ctt atg     1104
Val Glu Pro Glu Asn Arg Tyr Val Tyr Asp Ser Leu Tyr Gln Leu Met
    355                 360                 365 agt gcg aca ggg cgt gaa atg gct aat atc ggt cag caa agc aac caa     1152
Ser Ala Thr Gly Arg Glu Met Ala Asn Ile Gly Gln Gln Ser Asn Gln
370                 375                 380 ctt ccc tca ccc gtt ata cct gtt cct act gac gac agc act tat acc     1200
Leu Pro Ser Pro Val Ile Pro Val Pro Thr Asp Asp Ser Thr Tyr Thr
385                 390                 395                 400 aat tac ctt cgt acc tat act tat gac cgt ggc ggt aat ttg gtt caa     1248
Asn Tyr Leu Arg Thr Tyr Thr Tyr Asp Arg Gly Gly Asn Leu Val Gln
            405                 410                 415 atc cga cac agt tca ccc gcg act caa aat agt tac acc aca gat atc     1296
Ile Arg His Ser Ser Pro Ala Thr Gln Asn Ser Tyr Thr Thr Asp Ile
        420                 425                 430 acc gtt tca agc cgc agt aac cgg gcg gta ttg agt aca tta acg aca     1344
Thr Val Ser Ser Arg Ser Asn Arg Ala Val Leu Ser Thr Leu Thr Thr
    435                 440                 445 gat cca acc cga gtg gat gcg cta ttt gat tcc ggc ggt cat cag aag     1392
Asp Pro Thr Arg Val Asp Ala Leu Phe Asp Ser Gly Gly His Gln Lys
450                 455                 460 atg tta ata ccg ggg caa aat ctg gat tgg aat att cgg ggt gaa ttg     1440
Met Leu Ile Pro Gly Gln Asn Leu Asp Trp Asn Ile Arg Gly Glu Leu
465                 470                 475                 480 caa cga gtc aca ccg gtg agc cgt gaa aat agc agt gac agt gaa tgg     1488
Gln Arg Val Thr Pro Val Ser Arg Glu Asn Ser Ser Asp Ser Glu Trp
            485                 490                 495 tat cgc tat agc agt gat ggc atg cgg ctg cta aaa gtg agt gaa cag     1536
Tyr Arg Tyr Ser Ser Asp Gly Met Arg Leu Leu Lys Val Ser Glu Gln
        500                 505                 510 cag acg ggc aac agt act caa gta caa cgg gtg act tat ctg ccg gga     1584
Gln Thr Gly Asn Ser Thr Gln Val Gln Arg Val Thr Tyr Leu Pro Gly
    515                 520                 525 tta gag cta cgg aca act ggg gtt gca gat aaa aca acc gaa gat ttg     1632
Leu Glu Leu Arg Thr Thr Gly Val Ala Asp Lys Thr Thr Glu Asp Leu
530                 535                 540 cag gtg att acg gta ggt gaa gcg ggt cgc gca cag gta agg gta ttg     1680
Gln Val Ile Thr Val Gly Glu Ala Gly Arg Ala Gln Val Arg Val Leu
545                 550                 555                 560 cac tgg gaa agt ggt aag ccg aca gat att gac aac aat cag gtg cgc     1728
His Trp Glu Ser Gly Lys Pro Thr Asp Ile Asp Asn Asn Gln Val Arg
            565                 570                 575
```

```
tac agc tac gat aat ctg ctt ggc tcc agc cag ctt gaa ctg gat agc    1776
Tyr Ser Tyr Asp Asn Leu Leu Gly Ser Ser Gln Leu Glu Leu Asp Ser
            580                 585                 590 gaa ggg cag att ctc agt cag gaa gag tat tat ccg tat ggc ggt acg    1824
Glu Gly Gln Ile Leu Ser Gln Glu Glu Tyr Tyr Pro Tyr Gly Gly Thr
        595                 600                 605 gcg ata tgg gcg gcg aga aat cag aca gaa gcc agc tac aaa ttt att    1872
Ala Ile Trp Ala Ala Arg Asn Gln Thr Glu Ala Ser Tyr Lys Phe Ile
610                 615                 620 cgt tac tcc ggt aaa gag cgg gat gcc act gga ttg tat tat tac ggc    1920
Arg Tyr Ser Gly Lys Glu Arg Asp Ala Thr Gly Leu Tyr Tyr Tyr Gly
625                 630                 635                 640 tac cgt tat tat caa cct tgg gtg ggt cga tgg ttg agt gct gat ccg    1968
Tyr Arg Tyr Tyr Gln Pro Trp Val Gly Arg Trp Leu Ser Ala Asp Pro
            645                 650                 655 gcg gga acc gtg gat ggg ctg aat ttg tac cga atg gtg agg aat aac    2016
Ala Gly Thr Val Asp Gly Leu Asn Leu Tyr Arg Met Val Arg Asn Asn
        660                 665                 670 ccc atc aca ttg act gac cat gac gga tta gca ccg tct cca aat aga    2064
Pro Ile Thr Leu Thr Asp His Asp Gly Leu Ala Pro Ser Pro Asn Arg
    675                 680                 685 aat cga aat aca ttt tgg ttt gct tca ttt ttg ttt cgt aaa cct gat    2112
Asn Arg Asn Thr Phe Trp Phe Ala Ser Phe Leu Phe Arg Lys Pro Asp
690                 695                 700 gag gga atg tcc gcg tca atg aga cgg gga caa aaa att ggc aga gcc    2160
Glu Gly Met Ser Ala Ser Met Arg Arg Gly Gln Lys Ile Gly Arg Ala
705                 710                 715                 720 att gcc ggc ggg att gcg att ggc ggt ctt gcg gct acc att gcc gct    2208
Ile Ala Gly Gly Ile Ala Ile Gly Gly Leu Ala Ala Thr Ile Ala Ala
            725                 730                 735 acg gct ggc gcg gct atc ccc gtc att ctg ggg gtt gcg gcc gta ggc    2256
Thr Ala Gly Ala Ala Ile Pro Val Ile Leu Gly Val Ala Ala Val Gly
        740                 745                 750 gcg ggg att ggc gcg ttg atg gga tat aac gtc ggt agc ctg ctg gaa    2304
Ala Gly Ile Gly Ala Leu Met Gly Tyr Asn Val Gly Ser Leu Leu Glu
    755                 760                 765 aaa ggc ggg gca tta ctt gct cga ctc gta cag ggg aaa tcg acg tta    2352
Lys Gly Gly Ala Leu Leu Ala Arg Leu Val Gln Gly Lys Ser Thr Leu
770                 775                 780 gta cag tcg gcg gct ggc gcg gct gcc gga gcg agt tca gcc gcg gct    2400
Val Gln Ser Ala Ala Gly Ala Ala Ala Gly Ala Ser Ser Ala Ala Ala
785                 790                 795                 800 tat ggc gca cgg gca caa ggt gtc ggt gtt gca tca gcc gcc ggg gcg    2448
Tyr Gly Ala Arg Ala Gln Gly Val Gly Val Ala Ser Ala Ala Gly Ala
            805                 810                 815 gta aca ggg gct gtg gga tca tgg ata aat aat gct gat cgg ggg att    2496
Val Thr Gly Ala Val Gly Ser Trp Ile Asn Asn Ala Asp Arg Gly Ile
        820                 825                 830 ggc ggc gct att ggg gcc ggg agt gcg gta ggc acc att gat act atg    2544
Gly Gly Ala Ile Gly Ala Gly Ser Ala Val Gly Thr Ile Asp Thr Met
    835                 840                 845 tta ggg act gcc tct acc ctt acc cat gaa gtc ggg gca gcg gcg ggt    2592
Leu Gly Thr Ala Ser Thr Leu Thr His Glu Val Gly Ala Ala Ala Gly
850                 855                 860 ggg gcg gcg ggt ggg atg atc acc ggt acg caa ggg agt act cgg gca    2640
Gly Ala Ala Gly Gly Met Ile Thr Gly Thr Gln Gly Ser Thr Arg Ala
865                 870                 875                 880 ggt atc cat gcc ggt att ggc acc tat tat ggc tcc tgg att ggt ttt    2688
Gly Ile His Ala Gly Ile Gly Thr Tyr Tyr Gly Ser Trp Ile Gly Phe
            885                 890                 895
```

-continued

```
ggt tta gat gtc gct agt aac ccc gcc gga cat tta gcg aat tac gca    2736
Gly Leu Asp Val Ala Ser Asn Pro Ala Gly His Leu Ala Asn Tyr Ala
        900                 905                 910 gtg ggt tat gcc gct ggt ttg ggt gct gaa atg gct gtc aac aga ata    2784
Val Gly Tyr Ala Ala Gly Leu Gly Ala Glu Met Ala Val Asn Arg Ile
    915                 920                 925 atg ggt ggt gga ttt ttg agt agg ctc tta ggc cgg gtt gtc agc cca    2832
Met Gly Gly Gly Phe Leu Ser Arg Leu Leu Gly Arg Val Val Ser Pro
930                 935                 940 tat gcc gcc ggt tta gcc aga caa tta gta cat ttc agt gtc gcc aga    2880
Tyr Ala Ala Gly Leu Ala Arg Gln Leu Val His Phe Ser Val Ala Arg
945                 950                 955                 960 cct gtc ttt gag ccg ata ttt agt gtt ctc ggc ggg ctt gtc ggt ggt    2928
Pro Val Phe Glu Pro Ile Phe Ser Val Leu Gly Gly Leu Val Gly Gly
                965                 970                 975 att gga act ggc ctg cac aga gtg atg gga aga gag agt tgg att tcc    2976
Ile Gly Thr Gly Leu His Arg Val Met Gly Arg Glu Ser Trp Ile Ser
            980                 985                 990 aga gcg tta agt gct gcc ggt agt ggt ata gat cat gtc gct ggc atg    3024
Arg Ala Leu Ser Ala Ala Gly Ser Gly Ile Asp His Val Ala Gly Met
        995                 1000                1005 att ggt aat cag atc aga ggc agg gtc ttg acc aca acc ggg atc        3069
Ile Gly Asn Gln Ile Arg Gly Arg Val Leu Thr Thr Thr Gly Ile
    1010                1015                1020 gct aat gcg ata gac tat ggc acc agt gct gtg gga gcc gca cga        3114
Ala Asn Ala Ile Asp Tyr Gly Thr Ser Ala Val Gly Ala Ala Arg
    1025                1030                1035 cga gtt ttt tct ttg taa                                            3132
Arg Val Phe Ser Leu
    1040
```

<210> SEQ ID NO 15
<211> LENGTH: 915
<212> TYPE: PRT
<213> ORGANISM: Photorhabdus luminescens

<400> SEQUENCE: 15

```
Met Ser Ser Tyr Asn Ser Ala Ile Asp Gln Lys Thr Pro Ser Ile Lys
1               5                   10                  15

Val Leu Asp Asn Arg Lys Leu Asn Val Arg Thr Leu Glu Tyr Leu Arg
            20                  25                  30

Thr Gln Ala Asp Glu Asn Ser Asp Glu Leu Ile Thr Phe Tyr Glu Phe
        35                  40                  45

Asn Ile Pro Gly Phe Gln Val Lys Ser Thr Asp Pro Arg Lys Asn Lys
    50                  55                  60

Asn Gln Ser Gly Pro Asn Phe Ile Arg Val Phe Asn Leu Ala Gly Gln
65                  70                  75                  80

Val Leu Arg Glu Glu Ser Val Asp Ala Gly Arg Thr Ile Thr Leu Asn
                85                  90                  95

Asp Ile Glu Ser Arg Pro Val Leu Ile Ile Asn Ala Thr Gly Val Arg
            100                 105                 110

Gln Asn His Arg Tyr Glu Asp Asn Thr Leu Pro Gly Arg Leu Leu Ala
        115                 120                 125

Ile Thr Glu Gln Val Gln Ala Gly Glu Lys Thr Glu Arg Leu Ile
    130                 135                 140

Trp Ala Gly Asn Thr Pro Gln Glu Lys Asp Tyr Asn Leu Ala Gly Gln
145                 150                 155                 160
```

-continued

```
Cys Val Arg His Tyr Asp Thr Ala Gly Leu Thr Gln Leu Asn Ser Leu
            165                 170                 175

Ser Leu Ala Gly Val Val Leu Ser Gln Ser Gln Leu Leu Val Asp
        180                 185                 190

Asp Lys Asn Ala Asp Trp Thr Gly Glu Asp Gln Ser Leu Trp Gln Gln
        195                 200                 205

Lys Leu Ser Ser Asp Val Tyr Thr Thr Gln Asn Lys Ala Asp Ala Thr
210                 215                 220

Gly Ala Leu Leu Thr Gln Thr Asp Ala Lys Gly Asn Ile Gln Arg Leu
225                 230                 235                 240

Ala Tyr Asp Val Ala Gly Gln Leu Lys Gly Cys Trp Leu Thr Leu Lys
                245                 250                 255

Gly Gln Ala Glu Gln Val Ile Ile Lys Ser Leu Thr Tyr Ser Ala Ala
                260                 265                 270

Gly Gln Lys Leu Arg Glu Glu His Gly Asn Gly Val Ile Thr Glu Tyr
            275                 280                 285

Ser Tyr Glu Pro Glu Thr Gln Arg Leu Ile Gly Ile Ala Thr Arg Arg
        290                 295                 300

Pro Ser Asp Ala Lys Val Leu Gln Asp Leu Arg Tyr Gln Tyr Asp Pro
305                 310                 315                 320

Val Gly Asn Val Ile Asn Ile Arg Asn Asp Ala Glu Ala Thr Arg Phe
                325                 330                 335

Trp Arg Asn Gln Lys Val Val Pro Glu Asn Ser Tyr Thr Tyr Asp Ser
                340                 345                 350

Leu Tyr Gln Leu Ile Ser Ala Thr Gly Arg Glu Met Ala Asn Ile Gly
            355                 360                 365

Gln Gln Asn Asn Gln Leu Pro Ser Pro Ala Leu Pro Ser Asp Asn Asn
        370                 375                 380

Thr Tyr Thr Asn Tyr Thr Arg Ser Tyr Ser Tyr Asp His Ser Gly Asn
385                 390                 395                 400

Leu Thr Gln Ile Arg His Ser Ser Pro Ala Thr Gln Asn Asn Tyr Thr
                405                 410                 415

Val Ala Ile Thr Leu Ser Asn Arg Ser Asn Arg Gly Val Leu Ser Thr
                420                 425                 430

Leu Thr Thr Asp Pro Asn Gln Val Asp Thr Leu Phe Asp Ala Gly Gly
            435                 440                 445

His Gln Thr Ser Leu Leu Pro Gly Gln Thr Leu Ile Trp Thr Pro Arg
    450                 455                 460

Gly Glu Leu Lys Gln Val Asn Asn Gly Pro Gly Asn Glu Trp Tyr Arg
465                 470                 475                 480

Tyr Asp Ser Asn Gly Met Arg Gln Leu Lys Val Ser Glu Gln Pro Thr
                485                 490                 495

Gln Asn Thr Thr Gln Gln Arg Val Ile Tyr Leu Pro Gly Leu Glu
        500                 505                 510

Leu Arg Thr Thr Gln Ser Asn Ala Thr Thr Glu Glu Leu His Val
            515                 520                 525

Ile Thr Leu Gly Glu Ala Gly Arg Ala Gln Val Arg Val Leu His Trp
        530                 535                 540

Glu Ser Gly Lys Pro Glu Asp Val Asn Asn Gln Leu Arg Tyr Ser
545                 550                 555                 560

Tyr Asp Asn Leu Ile Gly Ser Ser Gln Leu Glu Leu Asp Asn Gln Gly
                565                 570                 575

Gln Ile Ile Ser Glu Glu Glu Tyr Tyr Pro Phe Gly Gly Thr Ala Leu
```

```
                    580                 585                 590
Trp Ala Ala Asn Ser Gln Thr Glu Ala Ser Tyr Lys Thr Ile Arg Tyr
            595                 600                 605

Ser Gly Lys Glu Arg Asp Ala Thr Gly Leu Tyr Tyr Gly Tyr Arg
    610                 615                 620

Tyr Tyr Gln Pro Trp Ala Gly Arg Trp Leu Ser Ala Asp Pro Ala Gly
625                 630                 635                 640

Thr Ile Asp Gly Leu Asn Leu Tyr Arg Met Val Arg Asn Asn Pro Val
                645                 650                 655

Ser Leu Gln Asp Glu Asn Gly Leu Ala Pro Glu Lys Gly Lys Tyr Thr
            660                 665                 670

Lys Glu Val Asn Phe Phe Asp Glu Leu Lys Phe Lys Leu Ala Ala Lys
        675                 680                 685

Ser Ser His Val Val Lys Trp Asn Glu Lys Glu Ser Ser Tyr Thr Lys
    690                 695                 700

Asn Lys Ser Leu Lys Val Val Arg Val Gly Asp Ser Asp Pro Ser Gly
705                 710                 715                 720

Tyr Leu Leu Ser His Glu Glu Leu Leu Lys Gly Ile Glu Lys Ser Gln
                725                 730                 735

Ile Ile Tyr Ser Arg Leu Glu Glu Asn Ser Ser Leu Ser Glu Lys Ser
            740                 745                 750

Lys Thr Asn Leu Ser Leu Gly Ser Glu Ile Ser Gly Tyr Met Ala Arg
        755                 760                 765

Thr Ile Gln Asp Thr Ile Ser Glu Tyr Ala Glu His Lys Tyr Arg
    770                 775                 780

Ser Asn His Pro Asp Phe Tyr Ser Glu Thr Asp Phe Phe Ala Leu Met
785                 790                 795                 800

Asp Lys Ser Glu Lys Asn Asp Tyr Ser Gly Glu Arg Lys Ile Tyr Ala
                805                 810                 815

Ala Met Glu Val Lys Val Tyr His Asp Leu Lys Asn Lys Gln Ser Glu
            820                 825                 830

Leu His Val Asn Tyr Ala Leu Ala His Pro Tyr Thr Gln Leu Ser Asn
        835                 840                 845

Glu Glu Arg Ala Leu Leu Gln Glu Thr Glu Pro Ala Ile Ala Ile Asp
    850                 855                 860

Arg Glu Tyr Asn Phe Lys Gly Val Gly Lys Phe Leu Thr Met Lys Ala
865                 870                 875                 880

Ile Lys Lys Ser Leu Lys Gly His Lys Ile Asn Arg Ile Ser Thr Glu
                885                 890                 895

Ala Ile Asn Ile Arg Ser Ala Ala Ile Ala Glu Asn Leu Gly Met Arg
            900                 905                 910

Arg Thr Ser
        915

<210> SEQ ID NO 16
<211> LENGTH: 960
<212> TYPE: PRT
<213> ORGANISM: Photorhabdus luminescens

<400> SEQUENCE: 16

Met Lys Asn Ile Asp Pro Lys Leu Tyr Gln Lys Thr Pro Thr Val Ser
1               5                   10                  15

Val Tyr Asp Asn Arg Gly Leu Ile Ile Arg Asn Ile Asp Phe His Arg
            20                  25                  30
```

```
Thr Thr Ala Asn Gly Asp Pro Asp Thr Arg Ile Thr Arg His Gln Tyr
         35                  40                  45

Asp Ile His Gly His Leu Asn Gln Ser Ile Asp Pro Arg Leu Tyr Glu
         50                  55                  60

Ala Lys Gln Thr Asn Asn Thr Ile Lys Pro Asn Phe Leu Trp Gln Tyr
 65                  70                  75                  80

Asp Leu Thr Gly Asn Pro Leu Cys Thr Glu Ser Ile Asp Ala Gly Arg
                 85                  90                  95

Thr Val Thr Leu Asn Asp Ile Glu Gly Arg Pro Leu Leu Thr Val Thr
             100                 105                 110

Ala Thr Gly Val Ile Gln Thr Arg Gln Tyr Glu Thr Ser Ser Leu Pro
             115                 120                 125

Gly Arg Leu Leu Ser Val Ala Glu Gln Thr Pro Glu Glu Lys Thr Ser
         130                 135                 140

Arg Ile Thr Glu Arg Leu Ile Trp Ala Gly Asn Thr Glu Ala Glu Lys
145                 150                 155                 160

Asp His Asn Leu Ala Gly Gln Cys Val Arg His Tyr Asp Thr Ala Gly
                 165                 170                 175

Val Thr Arg Leu Glu Ser Leu Ser Leu Thr Gly Thr Val Leu Ser Gln
             180                 185                 190

Ser Ser Gln Leu Leu Ile Asp Thr Gln Glu Ala Asn Trp Thr Gly Asp
         195                 200                 205

Asn Glu Thr Val Trp Gln Asn Met Leu Ala Asp Asp Ile Tyr Thr Thr
         210                 215                 220

Leu Ser Thr Phe Asp Ala Thr Gly Ala Leu Leu Thr Gln Thr Asp Ala
225                 230                 235                 240

Lys Gly Asn Ile Gln Arg Leu Ala Tyr Asp Val Ala Gly Gln Leu Asn
                 245                 250                 255

Gly Ser Trp Leu Thr Leu Lys Gly Gln Thr Glu Gln Val Ile Ile Lys
             260                 265                 270

Ser Leu Thr Tyr Ser Ala Ala Gly Gln Lys Leu Arg Glu Glu His Gly
         275                 280                 285

Asn Asp Val Ile Thr Glu Tyr Ser Tyr Glu Pro Glu Thr Gln Arg Leu
         290                 295                 300

Ile Gly Ile Lys Thr Arg Arg Pro Ser Asp Thr Lys Val Leu Gln Asp
305                 310                 315                 320

Leu Arg Tyr Glu Tyr Asp Pro Val Gly Asn Val Ile Ser Ile Arg Asn
                 325                 330                 335

Asp Ala Glu Ala Thr Arg Phe Trp His Asn Gln Lys Val Met Pro Glu
             340                 345                 350

Asn Thr Tyr Thr Tyr Asp Ser Leu Tyr Gln Leu Ile Ser Ala Thr Gly
         355                 360                 365

Arg Glu Met Ala Asn Ile Gly Gln Gln Ser His Gln Phe Pro Ser Pro
         370                 375                 380

Ala Leu Pro Ser Asp Asn Asn Thr Tyr Thr Asn Tyr Thr Arg Thr Tyr
385                 390                 395                 400

Thr Tyr Asp Arg Gly Gly Asn Leu Thr Lys Ile Gln His Ser Ser Pro
                 405                 410                 415

Ala Thr Gln Asn Asn Tyr Thr Thr Asn Ile Thr Val Ser Asn Arg Ser
             420                 425                 430

Asn Arg Ala Val Leu Ser Thr Leu Thr Glu Asp Pro Ala Gln Val Asp
         435                 440                 445

Ala Leu Phe Asp Ala Gly Gly His Gln Asn Thr Leu Ile Ser Gly Gln
```

```
              450                 455                 460
Asn Leu Asn Trp Asn Thr Arg Gly Glu Leu Gln Gln Val Thr Leu Val
465                 470                 475                 480

Lys Arg Asp Lys Gly Ala Asn Asp Asp Arg Glu Trp Tyr Arg Tyr Ser
                485                 490                 495

Gly Asp Gly Arg Arg Met Leu Lys Ile Asn Glu Gln Gln Ala Ser Asn
            500                 505                 510

Asn Ala Gln Thr Gln Arg Val Thr Tyr Leu Pro Asn Leu Glu Leu Arg
        515                 520                 525

Leu Thr Gln Asn Ser Thr Ala Thr Thr Glu Asp Leu Gln Val Ile Thr
    530                 535                 540

Val Gly Glu Ala Gly Arg Ala Gln Val Arg Val Leu His Trp Glu Ser
545                 550                 555                 560

Gly Lys Pro Glu Asp Ile Asp Asn Asn Gln Leu Arg Tyr Ser Tyr Asp
                565                 570                 575

Asn Leu Ile Gly Ser Ser Gln Leu Glu Leu Asp Ser Glu Gly Gln Ile
            580                 585                 590

Ile Ser Glu Glu Glu Tyr Tyr Pro Tyr Gly Gly Thr Ala Leu Trp Ala
        595                 600                 605

Ala Arg Asn Gln Thr Glu Ala Ser Tyr Lys Thr Ile Arg Tyr Ser Gly
    610                 615                 620

Lys Glu Arg Asp Ala Thr Gly Leu Tyr Tyr Tyr Gly Tyr Arg Tyr Tyr
625                 630                 635                 640

Gln Pro Trp Ile Gly Arg Trp Leu Ser Ser Asp Pro Ala Gly Thr Ile
                645                 650                 655

Asp Gly Leu Asn Leu Tyr Arg Met Val Arg Asn Asn Pro Val Thr Leu
            660                 665                 670

Leu Asp Pro Asp Gly Leu Met Pro Thr Ile Ala Glu Arg Ile Ala Ala
        675                 680                 685

Leu Lys Lys Asn Lys Val Thr Asp Ser Ala Pro Ser Pro Ala Asn Ala
    690                 695                 700

Thr Asn Val Ala Ile Asn Ile Arg Pro Pro Val Ala Pro Lys Pro Ser
705                 710                 715                 720

Leu Pro Lys Ala Ser Thr Ser Ser Gln Pro Thr Thr His Pro Ile Gly
                725                 730                 735

Ala Ala Asn Ile Lys Pro Thr Thr Ser Gly Ser Ser Ile Val Ala Pro
            740                 745                 750

Leu Ser Pro Val Gly Asn Lys Ser Thr Ser Glu Ile Ser Leu Pro Glu
        755                 760                 765

Ser Ala Gln Ser Ser Ser Ser Ser Thr Thr Ser Thr Asn Leu Gln Lys
    770                 775                 780

Lys Ser Phe Thr Leu Tyr Arg Ala Asp Asn Arg Ser Phe Glu Glu Met
785                 790                 795                 800

Gln Ser Lys Phe Pro Glu Gly Phe Lys Ala Trp Thr Pro Leu Asp Thr
                805                 810                 815

Lys Met Ala Arg Gln Phe Ala Ser Ile Phe Ile Gly Gln Lys Asp Thr
            820                 825                 830

Ser Asn Leu Pro Lys Glu Thr Val Lys Asn Ile Ser Thr Trp Gly Ala
        835                 840                 845

Lys Pro Lys Leu Lys Asp Leu Ser Asn Tyr Ile Lys Tyr Thr Lys Asp
    850                 855                 860

Lys Ser Thr Val Trp Val Ser Thr Ala Ile Asn Thr Glu Ala Gly Gly
865                 870                 875                 880
```

-continued

Gln Ser Ser Gly Ala Pro Leu His Lys Ile Asp Met Asp Leu Tyr Glu
                885                 890                 895

Phe Ala Ile Asp Gly Gln Lys Leu Asn Pro Leu Pro Glu Gly Arg Thr
                900                 905                 910

Lys Asn Met Val Pro Ser Leu Leu Asp Thr Pro Gln Ile Glu Thr
                915                 920                 925

Ser Ser Ile Ile Ala Leu Asn His Gly Pro Val Asn Asp Ala Glu Ile
                930                 935                 940

Ser Phe Leu Thr Thr Ile Pro Leu Lys Asn Val Lys Pro His Lys Arg
945                 950                 955                 960

<210> SEQ ID NO 17
<211> LENGTH: 949
<212> TYPE: PRT
<213> ORGANISM: Photorhabdus luminescens

<400> SEQUENCE: 17

Met Lys Asn Ile Asp Pro Lys Leu Tyr Gln His Thr Pro Thr Val Asn
1               5                   10                  15

Val Tyr Asp Asn Arg Gly Leu Thr Ile Arg Asn Ile Asp Phe His Arg
                20                  25                  30

Asp Val Ala Gly Gly Asp Thr Asp Thr Arg Ile Thr Arg His Gln Tyr
            35                  40                  45

Asp Thr Arg Gly His Leu Ser Gln Ser Ile Asp Pro Arg Leu Tyr Asp
        50                  55                  60

Ala Lys Gln Thr Asn Asn Ser Thr Asn Pro Asn Phe Leu Trp Gln Tyr
65                  70                  75                  80

Asn Leu Thr Gly Asp Thr Leu Arg Thr Glu Ser Val Asp Ala Gly Arg
                85                  90                  95

Thr Val Ala Leu Asn Asp Ile Glu Gly Arg Gln Val Leu Ile Val Thr
            100                 105                 110

Ala Thr Gly Ala Ile Gln Thr Arg Gln Tyr Glu Ala Asn Thr Leu Pro
        115                 120                 125

Gly Arg Leu Leu Ser Val Ser Glu Gln Ala Pro Gly Glu Gln Thr Pro
    130                 135                 140

Arg Val Thr Glu His Phe Ile Trp Ala Gly Asn Thr Gln Ala Glu Lys
145                 150                 155                 160

Asp His Asn Leu Ala Gly Gln Tyr Val Arg His Tyr Asp Thr Ala Gly
                165                 170                 175

Val Thr Gln Leu Glu Ser Leu Ser Leu Thr Glu Asn Ile Leu Ser Gln
            180                 185                 190

Ser Arg Gln Leu Leu Ala Asp Gly Gln Glu Ala Asp Trp Thr Gly Asn
        195                 200                 205

Asp Glu Thr Leu Trp Gln Thr Lys Leu Asn Ser Glu Thr Tyr Thr Thr
    210                 215                 220

Gln Ser Thr Phe Asp Ala Thr Gly Ala Leu Leu Thr Gln Thr Asp Ala
225                 230                 235                 240

Lys Gly Asn Met Gln Arg Leu Ala Tyr Asn Val Ala Gly Gln Leu Gln
                245                 250                 255

Gly Ser Trp Leu Thr Leu Lys Asn Gln Ser Glu Gln Val Ile Val Lys
            260                 265                 270

Ser Leu Thr Tyr Ser Ala Ala Gly Gln Lys Leu Arg Glu Glu His Gly
        275                 280                 285

Asn Gly Val Ile Thr Glu Tyr Ser Tyr Glu Pro Glu Thr Leu Arg Leu

-continued

```
              290                 295                 300
Ile Gly Thr Thr Thr Arg Arg Gln Ser Asp Ser Lys Val Leu Gln Asp
305                 310                 315                 320

Leu Arg Tyr Glu His Asp Pro Val Gly Asn Ile Ile Ser Val Arg Asn
                325                 330                 335

Asp Ala Glu Ala Thr Arg Phe Trp Arg Asn Gln Lys Ile Val Pro Glu
                340                 345                 350

Asn Thr Tyr Thr Tyr Asp Ser Leu Tyr Gln Leu Ile Ser Ala Thr Gly
                355                 360                 365

Arg Glu Met Ala Asn Ile Gly Gln Gln Ser Asn Gln Leu Pro Ser Pro
370                 375                 380

Ile Ile Pro Leu Pro Thr Asp Glu Asn Ser Tyr Thr Asn Tyr Thr Arg
385                 390                 395                 400

Ser Tyr Asn Tyr Asp Arg Gly Gly Asn Leu Val Gln Ile Arg His Ser
                405                 410                 415

Ser Pro Ala Ala Gln Asn Asn Tyr Thr Thr Asp Ile Thr Val Ser Asn
                420                 425                 430

Arg Ser Asn Arg Ala Val Leu Ser Ser Leu Thr Ser Asp Pro Thr Gln
                435                 440                 445

Val Glu Ala Leu Phe Asp Ala Gly His Gln Thr Lys Leu Leu Pro
450                 455                 460

Gly Gln Glu Leu Ser Trp Asn Thr Arg Gly Glu Leu Lys Gln Val Thr
465                 470                 475                 480

Pro Val Ser Arg Glu Ser Ala Ser Asp Arg Glu Trp Tyr Arg Tyr Gly
                485                 490                 495

Asn Asp Gly Met Arg Arg Leu Lys Val Ser Glu Gln Gln Thr Gly Asn
                500                 505                 510

Ser Thr Gln Gln Gln Arg Val Thr Tyr Leu Pro Asp Leu Glu Leu Arg
                515                 520                 525

Thr Thr Gln Asn Gly Thr Thr Thr Ser Glu Asp Leu His Ala Ile Thr
                530                 535                 540

Val Gly Ala Ala Gly His Ala Gln Val Arg Val Leu His Trp Glu Thr
545                 550                 555                 560

Thr Pro Pro Ala Gly Ile Asn Asn Gln Leu Arg Tyr Ser Tyr Asp
                565                 570                 575

Asn Leu Ile Gly Ser Ser Gln Leu Glu Leu Asp Asn Ala Gly Gln Ile
                580                 585                 590

Ile Ser Gln Glu Glu Tyr Tyr Pro Phe Gly Gly Thr Ala Leu Trp Ala
                595                 600                 605

Ala Arg Asn Gln Ile Glu Ala Ser Tyr Lys Ile Leu Arg Tyr Ser Gly
                610                 615                 620

Lys Glu Arg Asp Ala Thr Gly Leu Tyr Tyr Gly Tyr Arg Tyr Tyr
625                 630                 635                 640

Gln Pro Trp Val Gly Arg Trp Leu Ser Ala Asp Pro Ala Gly Thr Ile
                645                 650                 655

Asp Gly Leu Asn Leu Tyr Arg Met Val Arg Asn Asn Pro Ser Thr Leu
                660                 665                 670

Val Asp Ile Ser Gly Leu Ala Pro Thr Lys Tyr Asn Ile Pro Gly Phe
                675                 680                 685

Asp Phe Asp Val Glu Ile Asp Glu Gln Lys Arg Ser Lys Leu Lys Pro
                690                 695                 700

Thr Leu Ile Arg Ile Lys Asp Glu Phe Leu His Tyr Gly Pro Val Asp
705                 710                 715                 720
```

```
Lys Leu Leu Glu Glu Lys Lys Pro Gly Leu Asn Val Pro Glu Leu
                725                 730                 735

Phe Asp Arg Gly Pro Ser Glu Asn Gly Val Ser Thr Leu Thr Phe Lys
            740                 745                 750

Lys Asp Leu Pro Ile Ser Cys Ile Ser Asn Thr Glu Tyr Thr Leu Asp
            755                 760                 765

Ile Leu Tyr Asn Lys His Glu Thr Lys Pro Phe Pro Tyr Glu Asn Glu
        770                 775                 780

Ala Thr Val Gly Ala Asp Leu Gly Val Ile Met Ser Val Glu Phe Gly
785                 790                 795                 800

Asn Lys Ser Ile Gly Asn Ala Ser Asp Glu Asp Leu Lys Glu His
                805                 810                 815

Leu Pro Leu Gly Lys Ser Thr Met Asp Lys Thr Asp Leu Pro Asp Leu
                820                 825                 830

Lys Gln Gly Leu Met Ile Ala Glu Lys Ile Lys Ser Gly Lys Gly Ala
                835                 840                 845

Tyr Pro Phe His Phe Gly Ala Ala Ile Ala Val Val Tyr Gly Glu Asp
850                 855                 860

Lys Lys Val Ala Ala Ser Ile Leu Thr Asp Leu Ser Glu Pro Lys Arg
865                 870                 875                 880

Asp Glu Gly Glu Tyr Leu Gln Ser Thr Arg Lys Val Ser Ala Met Phe
                885                 890                 895

Ile Thr Asn Val Asn Glu Phe Arg Gly His Asp Tyr Pro Lys Ser Lys
                900                 905                 910

Tyr Ser Ile Gly Leu Val Thr Ala Glu Lys Arg Gln Pro Val Ile Ser
            915                 920                 925

Lys Lys Arg Ala Asn Pro Glu Glu Ala Pro Ser Ser Ser Arg Asn Lys
            930                 935                 940

Lys Leu His Val His
945

<210> SEQ ID NO 18
<211> LENGTH: 2817
<212> TYPE: DNA
<213> ORGANISM: Photorhabdus luminescens strain W14
<220> FEATURE:
<221> NAME/KEY: exon
<222> LOCATION: (1)..(2817)

<400> SEQUENCE: 18 atg gaa aac att gac cca aaa ctt tat cac cat acg cct acc gtc agt        48
Met Glu Asn Ile Asp Pro Lys Leu Tyr His His Thr Pro Thr Val Ser
1               5                   10                  15 gtt cac gat aac cgt gga cta gct atc cgt aat att agt ttt cac cgc        96
Val His Asp Asn Arg Gly Leu Ala Ile Arg Asn Ile Ser Phe His Arg
            20                  25                  30 act acc gca gaa gca aat acc gat acc cgt att acc cgc cat caa tat       144
Thr Thr Ala Glu Ala Asn Thr Asp Thr Arg Ile Thr Arg His Gln Tyr
        35                  40                  45 aat gcc ggc gga tat ttg aac caa agc att gat cct cgc ctg tat gac       192
Asn Ala Gly Gly Tyr Leu Asn Gln Ser Ile Asp Pro Arg Leu Tyr Asp
    50                  55                  60 gcc aaa cag act aac aac gct gta caa ccg aat ttt atc tgg cga cat       240
Ala Lys Gln Thr Asn Asn Ala Val Gln Pro Asn Phe Ile Trp Arg His
65                  70                  75                  80 aat ttg acc ggc aat atc ctg cga aca gag agc gtc gat gcc ggt cgg       288
Asn Leu Thr Gly Asn Ile Leu Arg Thr Glu Ser Val Asp Ala Gly Arg
```

```
                       85                  90                  95
acg att acc ctc aac gat att gaa ggc cgc ccg gtg ttg acc atc aat      336
Thr Ile Thr Leu Asn Asp Ile Glu Gly Arg Pro Val Leu Thr Ile Asn
                100                 105                 110 gca gcc ggt gtc cgg caa aac cat cgc tac gaa gat aac acc ctg ccc      384
Ala Ala Gly Val Arg Gln Asn His Arg Tyr Glu Asp Asn Thr Leu Pro
            115                 120                 125 ggt cgc ctg ctc gct atc agc gaa caa gga cag gca gaa gag aaa acg      432
Gly Arg Leu Leu Ala Ile Ser Glu Gln Gly Gln Ala Glu Glu Lys Thr
        130                 135                 140 acc gag cgc ctt atc tgg gcc ggc aat acg ccg caa gaa aaa gac cac      480
Thr Glu Arg Leu Ile Trp Ala Gly Asn Thr Pro Gln Glu Lys Asp His
145                 150                 155                 160 aac ctt gcc ggt cag tgc gtc cgc cat tac gat acc gca gga ctc act      528
Asn Leu Ala Gly Gln Cys Val Arg His Tyr Asp Thr Ala Gly Leu Thr
                165                 170                 175 caa ctc aac agc ctt gcc ctg acc ggc gcc gtt cta tca caa tct caa      576
Gln Leu Asn Ser Leu Ala Leu Thr Gly Ala Val Leu Ser Gln Ser Gln
            180                 185                 190 caa ctg ctt acc gat aac cag gat gcc gac tgg aca ggt gaa gac cag      624
Gln Leu Leu Thr Asp Asn Gln Asp Ala Asp Trp Thr Gly Glu Asp Gln
        195                 200                 205 agc ctc tgg caa caa aaa ctg agt agt gat gtc tat atc acc caa agt      672
Ser Leu Trp Gln Gln Lys Leu Ser Ser Asp Val Tyr Ile Thr Gln Ser
210                 215                 220 aac act gat gcc acc ggg gct tta ctg acc cag acc gat gcc aaa ggc      720
Asn Thr Asp Ala Thr Gly Ala Leu Leu Thr Gln Thr Asp Ala Lys Gly
                225                 230                 235                 240 aac att cag cgg ctg gcc tat gat gtg gcc ggg cag cta aaa ggg agt      768
Asn Ile Gln Arg Leu Ala Tyr Asp Val Ala Gly Gln Leu Lys Gly Ser
            245                 250                 255 tgg tta aca ctc aaa ggt cag gcg gaa cag gtg att atc aaa tcg cta      816
Trp Leu Thr Leu Lys Gly Gln Ala Glu Gln Val Ile Ile Lys Ser Leu
        260                 265                 270 acc tac tcc gcc gcc ggg caa aaa tta cgt gaa gag cac ggt aac ggg      864
Thr Tyr Ser Ala Ala Gly Gln Lys Leu Arg Glu Glu His Gly Asn Gly
275                 280                 285 att gtc act gaa tac agc tac gaa ccg gaa acc caa cgg ctt atc ggc      912
Ile Val Thr Glu Tyr Ser Tyr Glu Pro Glu Thr Gln Arg Leu Ile Gly
                290                 295                 300 att acc act cgc cgt cca tca gac gcc aag gtg ttg caa gac cta cgc      960
Ile Thr Thr Arg Arg Pro Ser Asp Ala Lys Val Leu Gln Asp Leu Arg
305                 310                 315                 320 tat caa tat gac cca gta ggc aat gtc att agt atc cgt aat gat gcg     1008
Tyr Gln Tyr Asp Pro Val Gly Asn Val Ile Ser Ile Arg Asn Asp Ala
                325                 330                 335 gaa gcc act cgc ttt tgg cgc aat cag aaa gta gcc ccg gag aat agc     1056
Glu Ala Thr Arg Phe Trp Arg Asn Gln Lys Val Ala Pro Glu Asn Ser
            340                 345                 350 tat acc tac gat tcc ctg tat cag ctt atc agc gcc acc ggg cgc gag     1104
Tyr Thr Tyr Asp Ser Leu Tyr Gln Leu Ile Ser Ala Thr Gly Arg Glu
        355                 360                 365 atg gcc aat atc ggt cag caa agc aac caa ctt ccc tct ccg gcg cta     1152
Met Ala Asn Ile Gly Gln Gln Ser Asn Gln Leu Pro Ser Pro Ala Leu
370                 375                 380 cct tct gat aac aat acc tac acc aac tat act cgc act tat act tat     1200
Pro Ser Asp Asn Asn Thr Tyr Thr Asn Tyr Thr Arg Thr Tyr Thr Tyr
385                 390                 395                 400 gac cgt ggc ggc aat ttg acg aaa att cag cat agt tca cca gcc gcg     1248
```

```
Asp Arg Gly Gly Asn Leu Thr Lys Ile Gln His Ser Ser Pro Ala Ala
            405                 410                 415 caa aat aac tac acg acg gat ata acg gtt tca aat cgc agc aac cgc    1296
Gln Asn Asn Tyr Thr Thr Asp Ile Thr Val Ser Asn Arg Ser Asn Arg
        420                 425                 430 gcg gta ctc agc aca ttg acc gca gat cca act caa gtc gat gcc tta    1344
Ala Val Leu Ser Thr Leu Thr Ala Asp Pro Thr Gln Val Asp Ala Leu
            435                 440                 445 ttt gat gcg gga ggc cat caa acc agc ttg tta tcc ggc caa gtt cta    1392
Phe Asp Ala Gly Gly His Gln Thr Ser Leu Leu Ser Gly Gln Val Leu
    450                 455                 460 act tgg aca ccg cga ggc gaa ttg aaa caa gcc aac aat agc gca gga    1440
Thr Trp Thr Pro Arg Gly Glu Leu Lys Gln Ala Asn Asn Ser Ala Gly
465                 470                 475                 480 aat gag tgg tat cgc tac gat agc aac ggc ata cgc cag cta aaa gtg    1488
Asn Glu Trp Tyr Arg Tyr Asp Ser Asn Gly Ile Arg Gln Leu Lys Val
                485                 490                 495 aat gaa caa caa act cag aat atc ccg caa caa caa agg gta act tat    1536
Asn Glu Gln Gln Thr Gln Asn Ile Pro Gln Gln Gln Arg Val Thr Tyr
            500                 505                 510 cta ccg ggg ctg gaa ata cgt aca acc cag aac aac gcc aca aca aca    1584
Leu Pro Gly Leu Glu Ile Arg Thr Thr Gln Asn Asn Ala Thr Thr Thr
        515                 520                 525 gaa gag tta cac gtt atc aca ctc ggt aaa gcc ggc cgc gcg caa gtc    1632
Glu Glu Leu His Val Ile Thr Leu Gly Lys Ala Gly Arg Ala Gln Val
            530                 535                 540 cga gta ttg cat tgg gag agc ggt aaa cca gaa gat att aat aac aat    1680
Arg Val Leu His Trp Glu Ser Gly Lys Pro Glu Asp Ile Asn Asn Asn
545                 550                 555                 560 cag ctt cgt tac agc tac gat aat ctt att ggc tcc agc caa ctt caa    1728
Gln Leu Arg Tyr Ser Tyr Asp Asn Leu Ile Gly Ser Ser Gln Leu Gln
                565                 570                 575 tta gat agc gac gga caa att atc agt gaa gaa gaa tat tat cca ttt    1776
Leu Asp Ser Asp Gly Gln Ile Ile Ser Glu Glu Glu Tyr Tyr Pro Phe
            580                 585                 590 ggt ggt aca gcg ctg tgg gcg gca agg aat caa acc gaa gcc agc tat    1824
Gly Gly Thr Ala Leu Trp Ala Ala Arg Asn Gln Thr Glu Ala Ser Tyr
        595                 600                 605 aaa acc att cgt tat tct ggt aaa gag cgg gat gtt acc ggg ctg tat    1872
Lys Thr Ile Arg Tyr Ser Gly Lys Glu Arg Asp Val Thr Gly Leu Tyr
    610                 615                 620 tat tat ggc tac cgt tat tac caa ccg tgg gcg ggc aga tgg tta ggt    1920
Tyr Tyr Gly Tyr Arg Tyr Tyr Gln Pro Trp Ala Gly Arg Trp Leu Gly
625                 630                 635                 640 gca gac ccg gca gga acc att gat gga ctg aat tta tat cgc atg gtg    1968
Ala Asp Pro Ala Gly Thr Ile Asp Gly Leu Asn Leu Tyr Arg Met Val
                645                 650                 655 aga aat aac ccg gtg acg caa ttt gat gtt cag gga tta tca ccg gcc    2016
Arg Asn Asn Pro Val Thr Gln Phe Asp Val Gln Gly Leu Ser Pro Ala
            660                 665                 670 aac aga aca gaa gaa gcg ata ata aaa cag ggt tcc ttt acg gga atg    2064
Asn Arg Thr Glu Glu Ala Ile Ile Lys Gln Gly Ser Phe Thr Gly Met
        675                 680                 685 gaa gaa gct gtt tat aaa aaa atg gct aaa cct caa act ttc aaa cgc    2112
Glu Glu Ala Val Tyr Lys Lys Met Ala Lys Pro Gln Thr Phe Lys Arg
    690                 695                 700 caa aga gct atc gct gcc caa aca gag caa gaa gcc cat gaa tca ttg    2160
Gln Arg Ala Ile Ala Ala Gln Thr Glu Gln Glu Ala His Glu Ser Leu
705                 710                 715                 720
```

```
acc aac aac cct agt gta gat att agc cca att aaa aac tac acc aca      2208
Thr Asn Asn Pro Ser Val Asp Ile Ser Pro Ile Lys Asn Tyr Thr Thr
            725                 730                 735 gat agc tca caa att aat gcc gcg ata agg gaa aat cgt att acg cca      2256
Asp Ser Ser Gln Ile Asn Ala Ala Ile Arg Glu Asn Arg Ile Thr Pro
            740                 745                 750 gca gtg gaa agt tta gac gcc aca tta tct tcc cta caa gat aga caa      2304
Ala Val Glu Ser Leu Asp Ala Thr Leu Ser Ser Leu Gln Asp Arg Gln
            755                 760                 765 atg agg gta act tat cgg gtg atg acc tat gta gat aat tcc acg cca      2352
Met Arg Val Thr Tyr Arg Val Met Thr Tyr Val Asp Asn Ser Thr Pro
            770                 775                 780 tcg cct tgg cac tcg cca cag gaa gga aat agt att aat gtt ggt gat      2400
Ser Pro Trp His Ser Pro Gln Glu Gly Asn Ser Ile Asn Val Gly Asp
785                 790                 795                 800 atc gtt tcg gat aac gct tat tta tca aca tcg gcc cat cgt ggt ttt      2448
Ile Val Ser Asp Asn Ala Tyr Leu Ser Thr Ser Ala His Arg Gly Phe
                805                 810                 815 ctg aat ttt gtt cac aaa aaa gaa acc agt gaa act cga tac gtc aag      2496
Leu Asn Phe Val His Lys Lys Glu Thr Ser Glu Thr Arg Tyr Val Lys
            820                 825                 830 atg gca ttt tta acg aat gcg ggt gtc aat gtc cca gca gca tct atg      2544
Met Ala Phe Leu Thr Asn Ala Gly Val Asn Val Pro Ala Ala Ser Met
            835                 840                 845 tat aat aat gct ggc gag gag caa gta ttt aaa atg gat tta aac gat      2592
Tyr Asn Asn Ala Gly Glu Glu Gln Val Phe Lys Met Asp Leu Asn Asp
850                 855                 860 tca aga aaa agc ctt gct gaa aaa tta aaa cta aga gtc agt gga cca      2640
Ser Arg Lys Ser Leu Ala Glu Lys Leu Lys Leu Arg Val Ser Gly Pro
865                 870                 875                 880 caa tcg gga caa gcg gaa ata tta cta cct agg gaa aca cag ttc gaa      2688
Gln Ser Gly Gln Ala Glu Ile Leu Leu Pro Arg Glu Thr Gln Phe Glu
                885                 890                 895 gtt gtt tca atg aaa cat caa ggc aga gat acc tat gta tta ttg caa      2736
Val Val Ser Met Lys His Gln Gly Arg Asp Thr Tyr Val Leu Leu Gln
            900                 905                 910 gat att aac caa tcc gca gcc act cat aga aat gta cgt aac act tac      2784
Asp Ile Asn Gln Ser Ala Ala Thr His Arg Asn Val Arg Asn Thr Tyr
            915                 920                 925 acc ggt aat ttc aaa tca tcc agt gca aat taa                          2817
Thr Gly Asn Phe Lys Ser Ser Ser Ala Asn
            930                 935

<210> SEQ ID NO 19
<211> LENGTH: 1016
<212> TYPE: PRT
<213> ORGANISM: Xenorhabdus nematophilus

<400> SEQUENCE: 19

Met Lys Asn Phe Val His Ser Asn Thr Pro Ser Val Thr Val Leu Asp
1               5                   10                  15

Asn Arg Gly Gln Thr Val Arg Glu Ile Ala Trp Tyr Arg His Pro Asp
            20                  25                  30

Thr Pro Gln Val Thr Asp Glu Arg Ile Thr Gly Tyr Gln Tyr Asp Ala
        35                  40                  45

Gln Gly Ser Leu Thr Gln Ser Ile Asp Pro Arg Phe Tyr Glu Arg Gln
    50                  55                  60

Gln Thr Ala Ser Asp Lys Asn Ala Ile Thr Pro Asn Leu Ile Leu Leu
65                  70                  75                  80
```

```
Ser Ser Leu Ser Lys Lys Ala Leu Arg Thr Gln Ser Val Asp Ala Gly
            85                  90                  95

Thr Arg Val Ala Leu His Asp Val Ala Gly Arg Pro Val Leu Ala Val
           100                 105                 110

Ser Ala Asn Gly Val Ser Arg Thr Phe Gln Tyr Glu Ser Asp Asn Leu
           115                 120                 125

Pro Gly Arg Leu Leu Thr Ile Thr Glu Gln Val Lys Gly Glu Asn Ala
           130                 135                 140

Cys Ile Thr Glu Arg Leu Ile Trp Ser Gly Asn Thr Pro Ala Glu Lys
145                 150                 155                 160

Gly Asn Asn Leu Ala Gly Gln Cys Val Val His Tyr Asp Pro Thr Gly
               165                 170                 175

Met Asn Gln Thr Asn Ser Ile Ser Leu Thr Ser Ile Pro Leu Ser Ile
               180                 185                 190

Thr Gln Gln Leu Leu Lys Asp Asp Ser Glu Ala Asp Trp His Gly Met
               195                 200                 205

Asp Glu Ser Gly Trp Lys Asn Ala Leu Ala Pro Glu Ser Phe Thr Ser
           210                 215                 220

Val Ser Thr Thr Asp Ala Thr Gly Thr Val Leu Thr Ser Thr Asp Ala
225                 230                 235                 240

Ala Gly Asn Lys Gln Arg Ile Ala Tyr Asp Val Ala Gly Leu Leu Gln
               245                 250                 255

Gly Ser Trp Leu Ala Leu Lys Gly Lys Gln Glu Gln Val Ile Val Lys
               260                 265                 270

Ser Leu Thr Tyr Ser Ala Ala Ser Gln Lys Leu Arg Glu Glu His Gly
           275                 280                 285

Asn Gly Ile Val Thr Thr Tyr Thr Tyr Glu Pro Glu Thr Gln Arg Val
           290                 295                 300

Ile Gly Ile Lys Thr Glu Arg Pro Ser Gly His Ala Ala Gly Glu Lys
305                 310                 315                 320

Ile Leu Gln Asn Leu Arg Tyr Glu Tyr Asp Pro Val Gly Asn Val Leu
               325                 330                 335

Lys Ser Thr Asn Asp Ala Glu Ile Thr Arg Phe Trp Arg Asn Gln Lys
               340                 345                 350

Ile Val Pro Glu Asn Thr Tyr Thr Tyr Asp Ser Leu Tyr Gln Leu Val
               355                 360                 365

Ser Val Thr Gly Arg Glu Met Ala Asn Ile Gly Arg Gln Lys Asn Gln
           370                 375                 380

Leu Pro Ile Pro Ala Leu Ile Asp Asn Asn Thr Tyr Thr Asn Tyr Ser
385                 390                 395                 400

Arg Thr Tyr Asp Tyr Asp Arg Gly Gly Asn Leu Thr Arg Ile Arg His
               405                 410                 415

Asn Ser Pro Ile Thr Gly Asn Asn Tyr Thr Thr Asn Met Thr Val Ser
               420                 425                 430

Asp His Ser Asn Arg Ala Val Leu Glu Glu Leu Ala Gln Asp Pro Thr
               435                 440                 445

Gln Val Asp Met Leu Phe Thr Pro Gly Gly His Gln Thr Arg Leu Val
           450                 455                 460

Pro Gly Gln Asp Leu Phe Trp Thr Pro Arg Asp Glu Leu Gln Gln Val
465                 470                 475                 480

Ile Leu Val Asn Arg Glu Asn Thr Thr Pro Asp Gln Glu Phe Tyr Arg
               485                 490                 495

Tyr Asp Ala Asp Ser Gln Arg Val Ile Lys Thr His Ile Gln Lys Thr
```

-continued

```
                500                 505                 510
Gly Asn Ser Glu Gln Ile Gln Arg Thr Leu Tyr Leu Pro Glu Leu Glu
            515                 520                 525

Trp Arg Thr Thr Tyr Ser Gly Asn Thr Leu Lys Glu Phe Leu Gln Val
530                 535                 540

Ile Thr Val Gly Glu Ser Gly Gln Ala Gln Val Arg Val Leu His Trp
545                 550                 555                 560

Glu Thr Gly Lys Pro Ala Asp Ile Ser Asn Asp Gln Leu Arg Tyr Ser
            565                 570                 575

Tyr Gly Asn Leu Ile Gly Ser Ser Gly Leu Glu Leu Asp Ser Asp Gly
            580                 585                 590

Gln Ile Ile Ser Gln Glu Glu Tyr Tyr Pro Tyr Gly Gly Thr Ala Val
            595                 600                 605

Trp Ala Ala Arg Ser Gln Ser Glu Ala Asp Tyr Lys Thr Val Arg Tyr
610                 615                 620

Ser Gly Lys Glu Arg Asp Ala Thr Gly Leu Tyr Tyr Tyr Gly Tyr Arg
625                 630                 635                 640

Tyr Tyr Gln Ser Trp Thr Gly Arg Trp Leu Ser Val Asp Pro Ala Gly
            645                 650                 655

Glu Val Asp Gly Leu Asn Leu Phe Arg Met Cys Arg Asn Asn Pro Ile
            660                 665                 670

Val Phe Ser Asp Ser Asp Gly Arg Phe Pro Gly Gln Gly Val Leu Ala
            675                 680                 685

Trp Ile Gly Lys Lys Ala Tyr Arg Lys Ala Val Asn Ile Thr Thr Glu
690                 695                 700

His Leu Leu Glu Gln Gly Ala Ser Phe Asp Thr Phe Leu Lys Leu Asn
705                 710                 715                 720

Arg Gly Leu Arg Thr Phe Val Leu Gly Val Gly Val Ala Ser Leu Gly
            725                 730                 735

Val Lys Ala Ala Thr Ile Ala Gly Ala Ser Pro Trp Gly Ile Val Gly
            740                 745                 750

Ala Ala Ile Gly Gly Phe Val Ser Gly Ala Val Met Gly Phe Phe Ala
            755                 760                 765

Asn Asn Ile Ser Glu Lys Ile Gly Glu Val Leu Ser Tyr Leu Thr Arg
770                 775                 780

Lys Arg Ser Val Pro Val Gln Val Gly Ala Phe Val Val Thr Ser Leu
785                 790                 795                 800

Val Thr Ser Ala Leu Phe Asn Ser Ser Thr Gly Thr Ala Ile Ser
            805                 810                 815

Ala Ala Thr Ala Val Thr Val Gly Gly Leu Met Ala Leu Ala Gly Glu
            820                 825                 830

His Asn Thr Gly Met Ala Ile Ser Ile Ala Thr Pro Ala Gly Gln Gly
            835                 840                 845

Thr Leu Asp Thr Leu Arg Pro Gly Asn Val Ser Ala Pro Glu Arg Leu
            850                 855                 860

Gly Ala Leu Ser Gly Ala Ile Ile Gly Gly Ile Leu Leu Gly Arg His
865                 870                 875                 880

Gln Gly Ser Ser Glu Leu Gly Glu Arg Ala Ala Ile Gly Ala Met Tyr
            885                 890                 895

Gly Ala Arg Trp Gly Arg Ile Ile Gly Asn Leu Trp Asp Gly Pro Tyr
            900                 905                 910

Arg Phe Ile Gly Arg Leu Leu Leu Arg Arg Gly Ile Ser Ser Ala Ile
            915                 920                 925
```

```
Ser His Ala Val Ser Arg Ser Trp Phe Gly Arg Met Ile Gly Glu
        930             935                 940

Ser Val Gly Arg Asn Ile Ser Glu Val Leu Leu Pro Tyr Ser Arg Thr
945                 950                 955                 960

Pro Gly Glu Trp Val Gly Ala Ala Ile Gly Gly Thr Ala Ala Ala Ala
                965                 970                 975

His His Ala Val Gly Gly Glu Val Ala Asn Ala Ala Ser Arg Val Thr
            980                 985                 990

Trp Ser Gly Phe Lys Arg Ala Phe Asn Asn Phe Phe Phe Asn Ala Ser
        995                 1000                1005

Ala Arg His Asn Glu Ser Glu Ala
        1010            1015

<210> SEQ ID NO 20
<211> LENGTH: 962
<212> TYPE: PRT
<213> ORGANISM: Xenorhabdus bovienii

<400> SEQUENCE: 20

Met Asn Val Phe Asn Pro Thr Leu Tyr Ala Gly Thr Pro Thr Val Thr
1               5                   10                  15

Val Met Asp Asn Arg Gly Leu Ser Val Arg Asp Ile Ala Tyr His Arg
                20                  25                  30

Thr Thr Ala Gly Glu Gln Ala Asp Thr Arg Ile Thr Arg His Gln Tyr
            35                  40                  45

Ser Pro His Asn Phe Leu Ile Glu Ser Ile Asp Pro Arg Leu Phe Asp
        50                  55                  60

Leu Gln Ser Gln Ser Thr Ile Lys Pro Asn Phe Thr Tyr Cys Pro Ala
65                  70                  75                  80

Leu Lys Gly Asp Val Leu Arg Thr Glu Ser Val Asp Ala Gly Gln Thr
                85                  90                  95

Val Ile Leu Ser Asp Ile Glu Gly Arg Pro Leu Leu Asn Ile Ser Ala
            100                 105                 110

Met Gly Val Val Lys His Trp Gln Tyr Glu Glu Ser Thr Leu Pro Gly
        115                 120                 125

Arg Leu Leu Ala Val Ser Glu Arg Lys Asn Glu Ala Ser Thr Pro Gln
130                 135                 140

Ile Ile Glu Arg Phe Ile Trp Ser Gly Asn Ser Pro Ser Glu Lys Asp
145                 150                 155                 160

His Asn Leu Ala Gly Lys Tyr Leu Arg His Tyr Asp Thr Ala Gly Leu
                165                 170                 175

Asn Gln Leu Asn Ala Val Ser Leu Thr Ser Val Asp Leu Ser Gln Ser
            180                 185                 190

Arg Gln Leu Leu Gln Asp Asp Val Thr Ala Asp Trp Ser Gly Ser Asp
        195                 200                 205

Glu Ser Gln Trp Lys Thr Arg Leu Ser Asn Asp Ile Phe Thr Thr Glu
    210                 215                 220

Ile Thr Ala Asp Ala Val Gly Asn Phe Leu Thr Gln Asn Asp Ala Lys
225                 230                 235                 240

Ser Asn Gln Gln Arg Leu Ser Tyr Asp Val Ala Gly Gln Leu Lys Ala
                245                 250                 255

Ser Trp Leu Thr Ile Lys Gly Gln Asn Glu Gln Val Ile Val Asn Ser
            260                 265                 270

Leu Thr Tyr Ser Ala Ala Gly Gln Lys Leu Arg Glu Glu Gln Gly Asn
```

|  | 275 |  |  | 280 |  |  | 285 |  |  |  |  |
|---|---|---|---|---|---|---|---|---|---|---|---|

Gly Val Val Thr Glu Tyr Ser Tyr Glu Ala Gln Thr Trp Arg Leu Ile
    290                         295                           300

Gly Val Thr Ala Tyr Arg Gln Ser Asp Lys Lys Arg Leu Gln Asp Leu
305                        310                        315                        320

Val Tyr Asn Tyr Asp Pro Val Gly Asn Leu Leu Asn Ile Arg Asn Asn
                 325                        330                        335

Ala Glu Ala Thr Arg Phe Trp Arg Asn Gln Ile Val Glu Pro Glu Asn
                 340                        345                        350

His Tyr Ala Tyr Asp Ser Leu Tyr Gln Leu Ile Ser Ala Ser Gly Arg
                 355                        360                        365

Glu Ile Ala Ser Ile Gly Gln Gln Gly Ser Arg Leu Pro Val Pro Ile
    370                         375                           380

Ile Pro Leu Pro Ala Asn Asp Asp Val Tyr Thr Arg Tyr Thr Arg Thr
385                        390                        395                        400

Tyr His Tyr Asp Arg Gly Gly Asn Leu Cys Gln Ile Arg His Cys Ala
                 405                        410                        415

Pro Ala Thr Asp Asn Lys Tyr Thr Thr Lys Ile Thr Val Ser Asn Arg
                 420                        425                        430

Ser Asn Arg Ala Val Trp Asp Thr Leu Thr Thr Asp Pro Ala Lys Val
                 435                        440                        445

Asp Thr Leu Phe Asp His Gly His Gln Leu Gln Leu Gln Ser Gly
    450                         455                         460

Gln Thr Leu Cys Trp Asn Tyr Arg Gly Glu Leu Gln Gln Ile Thr Lys
465                        470                        475                        480

Ile Gln Arg Asp Glu Lys Pro Ala Asp Lys Glu Arg Tyr Arg Tyr Gly
                 485                        490                        495

Val Gly Ala Ala Arg Val Val Lys Ile Ser Thr Gln Ala Gly Gly
                 500                        505                        510

Ser Ser His Val Gln Arg Val Val Tyr Leu Pro Gly Leu Glu Leu Arg
                 515                        520                        525

Thr Thr Gln His Asp Ala Thr Leu Ile Glu Asp Leu Gln Val Ile Ile
    530                         535                           540

Met Gly Glu Ala Gly Arg Ala Gln Val Arg Val Leu His Trp Glu Ile
545                        550                        555                        560

Pro Pro Pro Asp Asn Leu Asn Asn Asp Ser Leu Arg Tyr Ser Tyr Asp
                 565                        570                        575

Ser Leu Met Gly Ser Ser Gln Leu Glu Leu Asp Gly Ala Gly Gln Ile
                 580                        585                        590

Ile Thr Gln Glu Glu Tyr Tyr Pro Tyr Gly Gly Thr Ala Ile Trp Ala
                 595                        600                        605

Ala Arg Asn Gln Thr Glu Ala Asn Tyr Lys Thr Ile Arg Tyr Ser Gly
    610                         615                         620

Lys Glu Arg Asp Ala Thr Gly Leu Tyr Tyr Tyr Gly His Arg Tyr Tyr
625                        630                        635                        640

Gln Pro Trp Leu Gly Arg Trp Leu Ser Ala Asp Pro Ala Gly Thr Val
                 645                        650                        655

Asp Gly Leu Asn Leu Tyr Arg Met Val Arg Asn Asn Pro Ile Thr Tyr
                 660                        665                        670

Arg Asp Ala Asp Gly Leu Ala Pro Ile Gly Asp Lys Ile Ser Glu Gly
                 675                        680                        685

Ile Tyr Glu Pro Glu Leu Arg Val Gly Leu Glu Arg Asp Asp Pro Asn
    690                         695                         700

```
Val Arg Asp Tyr Asp Arg Val Tyr Pro Asp Thr Ala Lys Thr Glu Met
705                 710                 715                 720

Ile Glu Ala Thr Ala Thr Thr Ile Ala Pro Ser Gln Met Leu Ser Ala
                725                 730                 735

His Ala Phe Ala Ser Val Pro Ile Leu Thr Asp Leu Phe Asn Pro Gln
            740                 745                 750

Thr Ala Arg Leu Ser Gln Lys Thr Thr Asp Ile Val Leu Asn Thr Gln
        755                 760                 765

Gly Gly Gly Asp Leu Ile Phe Thr Gly Met Asn Ile Lys Gly Lys Gly
770                 775                 780

Lys Glu Phe Asn Ala Leu Lys Ile Val Asp Thr Tyr Gly Gly Glu Met
785                 790                 795                 800

Pro Asp Ser Lys Thr Ala Ile Ser Ala Tyr Trp Leu Pro Gln Gly Gly
                805                 810                 815

Tyr Thr Asp Ile Pro Ile His Pro Thr Gly Ile Gln Lys Tyr Leu Phe
            820                 825                 830

Thr Pro Ala Phe Ser Gly Cys Thr Leu Ala Val Asp Lys Leu Asn Glu
        835                 840                 845

Asn Thr Leu Arg Ala Tyr His Val Glu Gly Ser Lys Glu Asp Ala Gln
850                 855                 860

Tyr Asn Asn Leu Ala Val Ala Ala His Gly Glu Gly Leu Val Met Ala
865                 870                 875                 880

Met Glu Phe Pro Asp Tyr Gly Phe His Thr Asp Lys Thr Gly Gln Arg
                885                 890                 895

Leu Arg Asn Thr Gln Gly Phe Ala Phe Met Ser Tyr Asn Gln Ser Gln
            900                 905                 910

Lys Lys Trp Glu Ile His Tyr Gln Arg Gln Ala Leu Thr Ser Asn Thr
        915                 920                 925

Gly Ile Met Asn Val Ser Ala Lys Asn Lys Ile Arg Leu Asn Ala Pro
930                 935                 940

Ser His Val Lys Asn Ser Ser Ile Lys Gly Thr Glu Ile Met Thr Thr
945                 950                 955                 960

His Phe

<210> SEQ ID NO 21
<211> LENGTH: 953
<212> TYPE: PRT
<213> ORGANISM: Paenibacillus strain DAS1529

<400> SEQUENCE: 21

Met Lys Met Ile Pro Trp Thr His His Tyr Leu Leu His Arg Leu Arg
1               5                   10                  15

Gly Glu Met Glu Val Lys Pro Met Asn Thr Thr Ser Ile Tyr Arg Gly
            20                  25                  30

Thr Pro Thr Ile Ser Val Val Asp Asn Arg Asn Leu Glu Ile Arg Ile
        35                  40                  45

Leu Gln Tyr Asn Arg Ile Ala Ala Glu Asp Pro Ala Asp Glu Cys Ile
    50                  55                  60

Leu Arg Asn Thr Tyr Thr Pro Leu Ser Tyr Leu Gly Ser Ser Met Asp
65                  70                  75                  80

Pro Arg Leu Phe Ser Gln Tyr Gln Asp Asp Arg Gly Thr Pro Pro Asn
                85                  90                  95

Ile Arg Thr Met Ala Ser Leu Arg Gly Glu Ala Leu Cys Ser Glu Ser
            100                 105                 110
```

```
Val Asp Ala Gly Arg Lys Ala Glu Leu Phe Asp Ile Glu Gly Arg Pro
        115                 120                 125
Val Trp Leu Ile Asp Ala Asn Gly Thr Glu Thr Thr Leu Glu Tyr Asp
130                 135                 140
Val Leu Gly Arg Pro Thr Ala Val Phe Glu Gln Gln Glu Gly Thr Asp
145                 150                 155                 160
Ser Pro Gln Cys Arg Glu Arg Phe Ile Tyr Gly Glu Lys Glu Ala Asp
                165                 170                 175
Ala Gln Ala Asn Asn Leu Arg Gly Gln Leu Val Arg His Tyr Asp Thr
            180                 185                 190
Ala Gly Arg Ile Gln Thr Asp Ser Ile Ser Leu Ala Gly Leu Pro Leu
        195                 200                 205
Arg Gln Ser Arg Gln Leu Leu Lys Asn Trp Asp Pro Gly Asp Trp
    210                 215                 220
Ser Met Asp Glu Glu Ser Ala Trp Ala Ser Leu Leu Ala Ala Glu Ala
225                 230                 235                 240
Tyr Asp Thr Ser Trp Arg Tyr Asp Ala Gln Asp Arg Val Leu Ala Gln
                245                 250                 255
Thr Asp Ala Lys Gly Asn Leu Gln Gln Leu Thr Tyr Asn Asp Ala Gly
            260                 265                 270
Gln Pro Gln Ala Val Ser Leu Lys Leu Gln Gly Gln Ala Glu Gln Arg
        275                 280                 285
Ile Trp Asn Arg Ile Glu Tyr Asn Ala Ala Gly Gln Val Asp Leu Ala
    290                 295                 300
Glu Ala Gly Asn Gly Ile Val Thr Glu Tyr Thr Tyr Glu Glu Ser Thr
305                 310                 315                 320
Gln Arg Leu Ile Arg Lys Lys Asp Ser Arg Gly Leu Ser Ser Gly Glu
                325                 330                 335
Arg Glu Val Leu Gln Asp Tyr Arg Tyr Glu Tyr Asp Pro Val Gly Asn
            340                 345                 350
Ile Leu Ser Ile Tyr Asn Glu Ala Glu Pro Val Arg Tyr Phe Arg Asn
        355                 360                 365
Gln Ala Val Ala Pro Lys Arg Gln Tyr Ala Tyr Asp Ala Leu Tyr Gln
370                 375                 380
Leu Val Ser Ser Ser Gly Arg Glu Ser Asp Ala Leu Arg Gln Gln Thr
385                 390                 395                 400
Ser Leu Pro Pro Leu Ile Thr Pro Ile Pro Leu Asp Asp Ser Gln Tyr
                405                 410                 415
Val Asn Tyr Ala Glu Lys Tyr Ser Tyr Asp Gln Ala Gly Asn Leu Ile
            420                 425                 430
Lys Leu Ser His Asn Gly Ala Ser Gln Tyr Thr Thr Asn Val Tyr Val
        435                 440                 445
Asp Lys Ser Ser Asn Arg Gly Ile Trp Arg Gly Glu Asp Ile Pro
    450                 455                 460
Asp Ile Ala Ala Ser Phe Asp Arg Ala Gly Asn Gln Gln Ala Leu Phe
465                 470                 475                 480
Pro Gly Arg Pro Leu Glu Trp Asp Thr Arg Asn Gln Leu Ser Arg Val
                485                 490                 495
His Met Val Val Arg Glu Gly Gly Asp Asn Asp Trp Glu Gly Tyr Leu
            500                 505                 510
Tyr Asp Ser Ser Gly Met Arg Ile Val Lys Arg Ser Thr Arg Lys Thr
        515                 520                 525
```

-continued

```
Gln Thr Thr Thr Gln Thr Asp Thr Thr Leu Tyr Leu Pro Gly Leu Glu
    530                 535                 540

Leu Arg Ile Arg Gln Thr Gly Asp Arg Val Thr Glu Ala Leu Gln Val
545                 550                 555                 560

Ile Thr Val Asp Glu Gly Ala Gly Gln Val Arg Val Leu His Trp Glu
                565                 570                 575

Asp Gly Thr Glu Pro Gly Gly Ile Ala Asn Asp Gln Tyr Arg Tyr Ser
            580                 585                 590

Leu Asn Asp His Leu Thr Ser Ser Leu Leu Glu Val Asp Gly Gln Gly
        595                 600                 605

Gln Ile Ile Ser Lys Glu Glu Phe Tyr Pro Tyr Gly Gly Thr Ala Leu
    610                 615                 620

Trp Thr Ala Arg Ser Glu Val Glu Ala Ser Tyr Lys Thr Ile Arg Tyr
625                 630                 635                 640

Ser Gly Lys Glu Arg Asp Ala Thr Gly Leu Tyr Tyr Tyr Gly His Arg
                645                 650                 655

Tyr Tyr Met Pro Trp Leu Gly Arg Trp Leu Asn Pro Asp Pro Ala Gly
            660                 665                 670

Met Val Asp Gly Leu Asn Leu Tyr Arg Met Val Arg Asn Asn Pro Ile
        675                 680                 685

Gly Leu Met Asp Pro Asn Gly Asn Ala Pro Ile Asn Val Ala Asp Tyr
    690                 695                 700

Ser Phe Val His Gly Asp Leu Val Tyr Gly Leu Ser Lys Glu Arg Gly
705                 710                 715                 720

Arg Tyr Leu Lys Leu Phe Asn Pro Asn Phe Asn Met Glu Lys Ser Asp
                725                 730                 735

Ser Pro Ala Met Val Ile Asp Gln Tyr Asn Asn Val Ala Leu Ser
            740                 745                 750

Ile Thr Asn Gln Tyr Lys Val Glu Glu Leu Met Lys Phe Gln Lys Asp
        755                 760                 765

Pro Gln Lys Ala Ala Arg Lys Ile Lys Val Pro Glu Gly Asn Arg Leu
    770                 775                 780

Ser Arg Asn Glu Asn Tyr Pro Leu Trp His Asp Tyr Ile Asn Ile Gly
785                 790                 795                 800

Glu Ala Lys Ala Ala Phe Lys Ala Ser His Ile Phe Gln Glu Val Lys
                805                 810                 815

Gly Asn Tyr Gly Lys Asp Tyr Tyr His Lys Leu Leu Leu Asp Arg Met
            820                 825                 830

Ile Glu Ser Pro Leu Leu Trp Lys Arg Gly Ser Lys Leu Gly Leu Glu
        835                 840                 845

Ile Ala Ala Thr Asn Gln Arg Thr Lys Ile His Phe Val Leu Asp Asn
    850                 855                 860

Leu Asn Ile Glu Gln Val Val Thr Lys Glu Gly Ser Gly Gly Gln Ser
865                 870                 875                 880

Ile Thr Ala Ser Glu Leu Arg Tyr Ile Tyr Arg Asn Arg Glu Arg Leu
                885                 890                 895

Asn Gly Arg Val Ile Phe Tyr Arg Asn Asn Glu Arg Leu Asp Gln Ala
            900                 905                 910

Pro Trp Gln Glu Asn Pro Asp Leu Trp Ser Lys Tyr Gln Pro Gly Leu
        915                 920                 925

Arg Gln Ser Ser Ser Arg Val Lys Glu Arg Gly Ile Gly Asn Phe
    930                 935                 940

Phe Arg Arg Phe Ser Met Lys Arg Lys
```

-continued

```
945                 950

<210> SEQ ID NO 22
<211> LENGTH: 930
<212> TYPE: PRT
<213> ORGANISM: Paenibacillus strain DAS1529

<400> SEQUENCE: 22

Met Asn Thr Thr Ser Ile Tyr Arg Gly Thr Pro Thr Ile Ser Val Val
1               5                   10                  15

Asp Asn Arg Asn Leu Glu Ile Arg Ile Leu Gln Tyr Asn Arg Ile Ala
            20                  25                  30

Ala Glu Asp Pro Ala Asp Glu Cys Ile Leu Arg Asn Thr Tyr Thr Pro
        35                  40                  45

Leu Ser Tyr Leu Gly Ser Ser Met Asp Pro Arg Leu Phe Ser Gln Tyr
    50                  55                  60

Gln Asp Asp Arg Gly Thr Pro Pro Asn Ile Arg Thr Met Ala Ser Leu
65                  70                  75                  80

Arg Gly Glu Ala Leu Cys Ser Glu Ser Val Asp Ala Gly Arg Lys Ala
                85                  90                  95

Glu Leu Phe Asp Ile Glu Gly Arg Pro Val Trp Leu Ile Asp Ala Asn
            100                 105                 110

Gly Thr Glu Thr Thr Leu Glu Tyr Asp Val Leu Gly Arg Pro Thr Ala
        115                 120                 125

Val Phe Glu Gln Gln Glu Gly Thr Asp Ser Pro Gln Cys Arg Glu Arg
    130                 135                 140

Phe Ile Tyr Gly Glu Lys Glu Ala Asp Ala Gln Ala Asn Asn Leu Arg
145                 150                 155                 160

Gly Gln Leu Val Arg His Tyr Asp Thr Ala Gly Arg Ile Gln Thr Asp
                165                 170                 175

Ser Ile Ser Leu Ala Gly Leu Pro Leu Arg Gln Ser Arg Gln Leu Leu
            180                 185                 190

Lys Asn Trp Asp Glu Pro Gly Asp Trp Ser Met Asp Glu Glu Ser Ala
        195                 200                 205

Trp Ala Ser Leu Leu Ala Ala Glu Ala Tyr Asp Thr Ser Trp Arg Tyr
    210                 215                 220

Asp Ala Gln Asp Arg Val Leu Ala Gln Thr Asp Ala Lys Gly Asn Leu
225                 230                 235                 240

Gln Gln Leu Thr Tyr Asn Asp Ala Gly Gln Pro Gln Ala Val Ser Leu
                245                 250                 255

Lys Leu Gln Gly Gln Ala Glu Gln Arg Ile Trp Asn Arg Ile Glu Tyr
            260                 265                 270

Asn Ala Ala Gly Gln Val Asp Leu Ala Glu Ala Gly Asn Gly Ile Val
        275                 280                 285

Thr Glu Tyr Thr Tyr Glu Glu Ser Thr Gln Arg Leu Ile Arg Lys Lys
    290                 295                 300

Asp Ser Arg Gly Leu Ser Ser Gly Glu Arg Glu Val Leu Gln Asp Tyr
305                 310                 315                 320

Arg Tyr Glu Tyr Asp Pro Val Gly Asn Ile Leu Ser Ile Tyr Asn Glu
                325                 330                 335

Ala Glu Pro Val Arg Tyr Phe Arg Asn Gln Ala Val Ala Pro Lys Arg
            340                 345                 350

Gln Tyr Ala Tyr Asp Ala Leu Tyr Gln Leu Val Ser Ser Ser Gly Arg
        355                 360                 365
```

-continued

Glu Ser Asp Ala Leu Arg Gln Gln Thr Ser Leu Pro Pro Leu Ile Thr
370                 375                 380

Pro Ile Pro Leu Asp Asp Ser Gln Tyr Val Asn Tyr Ala Glu Lys Tyr
385                 390                 395                 400

Ser Tyr Asp Gln Ala Gly Asn Leu Ile Lys Leu Ser His Asn Gly Ala
            405                 410                 415

Ser Gln Tyr Thr Thr Asn Val Tyr Val Asp Lys Ser Ser Asn Arg Gly
            420                 425                 430

Ile Trp Arg Gln Gly Glu Asp Ile Pro Asp Ile Ala Ala Ser Phe Asp
        435                 440                 445

Arg Ala Gly Asn Gln Gln Ala Leu Phe Pro Gly Arg Pro Leu Glu Trp
450                 455                 460

Asp Thr Arg Asn Gln Leu Ser Arg Val His Met Val Arg Glu Gly
465                 470                 475                 480

Gly Asp Asn Asp Trp Glu Gly Tyr Leu Tyr Asp Ser Ser Gly Met Arg
            485                 490                 495

Ile Val Lys Arg Ser Thr Arg Lys Thr Gln Thr Thr Thr Gln Thr Asp
            500                 505                 510

Thr Thr Leu Tyr Leu Pro Gly Leu Glu Leu Arg Ile Arg Gln Thr Gly
            515                 520                 525

Asp Arg Val Thr Glu Ala Leu Gln Val Ile Thr Val Asp Glu Gly Ala
530                 535                 540

Gly Gln Val Arg Val Leu His Trp Glu Asp Gly Thr Glu Pro Gly Gly
545                 550                 555                 560

Ile Ala Asn Asp Gln Tyr Arg Tyr Ser Leu Asn Asp His Leu Thr Ser
            565                 570                 575

Ser Leu Leu Glu Val Asp Gly Gln Gly Gln Ile Ile Ser Lys Glu Glu
        580                 585                 590

Phe Tyr Pro Tyr Gly Gly Thr Ala Leu Trp Thr Ala Arg Ser Glu Val
        595                 600                 605

Glu Ala Ser Tyr Lys Thr Ile Arg Tyr Ser Gly Lys Glu Arg Asp Ala
610                 615                 620

Thr Gly Leu Tyr Tyr Tyr Gly His Arg Tyr Tyr Met Pro Trp Leu Gly
625                 630                 635                 640

Arg Trp Leu Asn Pro Asp Pro Ala Gly Met Val Asp Gly Leu Asn Leu
                645                 650                 655

Tyr Arg Met Val Arg Asn Asn Pro Ile Gly Leu Met Asp Pro Asn Gly
            660                 665                 670

Asn Ala Pro Ile Asn Val Ala Asp Tyr Ser Phe Val His Gly Asp Leu
            675                 680                 685

Val Tyr Gly Leu Ser Lys Glu Arg Gly Arg Tyr Leu Lys Leu Phe Asn
        690                 695                 700

Pro Asn Phe Asn Met Glu Lys Ser Asp Ser Pro Ala Met Val Ile Asp
705                 710                 715                 720

Gln Tyr Asn Asn Asn Val Ala Leu Ser Ile Thr Asn Gln Tyr Lys Val
                725                 730                 735

Glu Glu Leu Met Lys Phe Gln Lys Asp Pro Gln Lys Ala Ala Arg Lys
            740                 745                 750

Ile Lys Val Pro Glu Gly Asn Arg Leu Ser Arg Asn Glu Asn Tyr Pro
        755                 760                 765

Leu Trp His Asp Tyr Ile Asn Ile Gly Glu Ala Lys Ala Ala Phe Lys
770                 775                 780

Ala Ser His Ile Phe Gln Glu Val Lys Gly Asn Tyr Gly Lys Asp Tyr

-continued 785 790 795 800

Tyr His Lys Leu Leu Leu Asp Arg Met Ile Glu Ser Pro Leu Leu Trp
805 810 815

Lys Arg Gly Ser Lys Leu Gly Leu Glu Ile Ala Ala Thr Asn Gln Arg
820 825 830

Thr Lys Ile His Phe Val Leu Asp Asn Leu Asn Ile Glu Gln Val Val
835 840 845

Thr Lys Glu Gly Ser Gly Gly Gln Ser Ile Thr Ala Ser Glu Leu Arg
850 855 860

Tyr Ile Tyr Arg Asn Arg Glu Arg Leu Asn Gly Arg Val Ile Phe Tyr
865 870 875 880

Arg Asn Asn Glu Arg Leu Asp Gln Ala Pro Trp Gln Glu Asn Pro Asp
885 890 895

Leu Trp Ser Lys Tyr Gln Pro Gly Leu Arg Gln Ser Ser Ser Ser Arg
900 905 910

Val Lys Glu Arg Gly Ile Gly Asn Phe Phe Arg Arg Phe Ser Met Lys
915 920 925

Arg Lys
930

<210> SEQ ID NO 23
<211> LENGTH: 973
<212> TYPE: PRT
<213> ORGANISM: Serratia entomophila

<400> SEQUENCE: 23

Met Ser Thr Ser Leu Phe Ser Ser Thr Pro Ser Val Ala Val Leu Asp
1 5 10 15

Asn Arg Gly Leu Leu Val Arg Glu Leu Gln Tyr Tyr Arg His Pro Asp
20 25 30

Thr Pro Glu Glu Thr Asp Glu Arg Ile Thr Cys His Gln His Asp Glu
35 40 45

Arg Gly Ser Leu Ser Gln Ser Ala Asp Pro Arg Leu His Ala Ala Gly
50 55 60

Leu Thr Asn Phe Thr Tyr Leu Asn Ser Leu Thr Gly Thr Val Leu Gln
65 70 75 80

Ser Val Ser Ala Asp Ala Gly Thr Ser Leu Glu Leu Ser Asp Ala Ala
85 90 95

Gly Arg Ala Phe Leu Ala Val Thr Gly Ala Gly Thr Glu Asp Ala Val
100 105 110

Thr Arg Thr Trp Gln Tyr Glu Asp Asp Thr Leu Pro Gly Arg Pro Leu
115 120 125

Ser Ile Thr Glu Gln Val Thr Gly Glu Ala Ala Gln Ile Thr Glu Arg
130 135 140

Phe Val Tyr Ala Gly Asn Thr Asp Ala Glu Lys Ile Leu Asn Leu Ala
145 150 155 160

Gly Gln Cys Val Ser His Tyr Asp Thr Ala Gly Leu Val Gln Thr Asp
165 170 175

Ser Ile Ala Leu Ser Gly Val Pro Leu Ala Val Thr Arg Gln Leu Leu
180 185 190

Pro Asp Ala Ala Gly Ala Asn Trp Met Gly Glu Asp Ala Ser Ala Trp
195 200 205

Asn Asp Leu Leu Asp Gly Glu Thr Phe Phe Thr Gln Thr His Ala Asp
210 215 220

-continued

```
Ala Thr Gly Ala Val Leu Ser Ile Thr Asp Ala Lys Gly Asn Leu Gln
225                 230                 235                 240

Arg Val Ala Tyr Asp Val Ala Gly Leu Leu Ser Gly Ser Trp Leu Thr
                245                 250                 255

Leu Lys Asp Gly Thr Glu Gln Val Ile Val Ala Ser Leu Thr Tyr Ser
            260                 265                 270

Ala Ala Gly Lys Lys Leu Arg Glu Glu His Gly Asn Gly Val Val Thr
        275                 280                 285

Ser Tyr Ile Tyr Glu Pro Glu Thr Gln Arg Leu Thr Gly Ile Lys Thr
    290                 295                 300

Glu Arg Pro Ser Gly His Val Ala Gly Ala Lys Val Leu Gln Asp Leu
305                 310                 315                 320

Arg Tyr Thr Tyr Asp Pro Val Gly Asn Val Leu Ser Val Asn Asn Asp
                325                 330                 335

Ala Glu Glu Thr Arg Phe Trp Arg Asn Gln Lys Val Val Pro Glu Asn
            340                 345                 350

Thr Tyr Ile Tyr Asp Ser Leu Tyr Gln Leu Val Ser Ala Thr Gly Arg
        355                 360                 365

Glu Met Ala Asn Ala Gly Gln Gln Gly Asn Asp Leu Pro Ser Ala Thr
    370                 375                 380

Ala Pro Leu Pro Thr Asp Ser Ser Ala Tyr Thr Asn Tyr Thr Arg Thr
385                 390                 395                 400

Tyr Arg Tyr Asp Arg Gly Gly Asn Leu Thr Gln Met Arg His Ser Ala
                405                 410                 415

Pro Ala Thr Asn Asn Asn Tyr Thr Thr Asp Ile Thr Val Ser Asp Arg
            420                 425                 430

Ser Asn Arg Ala Val Leu Ser Thr Leu Ala Glu Val Pro Ser Asp Val
        435                 440                 445

Asp Met Leu Phe Ser Ala Gly His Gln Lys His Leu Gln Pro Gly
    450                 455                 460

Gln Ala Leu Val Trp Thr Pro Arg Gly Glu Leu Gln Lys Val Thr Pro
465                 470                 475                 480

Val Val Arg Asp Gly Gly Ala Asp Asp Ser Glu Ser Tyr Arg Tyr Asp
                485                 490                 495

Ala Gly Ser Gln Arg Ile Ile Lys Thr Gly Thr Arg Gln Thr Gly Asn
            500                 505                 510

Asn Val Gln Thr Gln Arg Val Val Tyr Leu Pro Gly Leu Glu Leu Arg
        515                 520                 525

Ile Met Ala Asn Gly Val Thr Glu Lys Glu Ser Leu Gln Val Ile Thr
    530                 535                 540

Val Gly Glu Ala Gly Arg Ala Gln Val Arg Val Leu His Trp Glu Ile
545                 550                 555                 560

Gly Lys Pro Asp Asp Leu Asp Glu Asp Ser Val Arg Tyr Ser Tyr Asp
                565                 570                 575

Asn Leu Val Gly Ser Ser Gln Leu Glu Leu Asp Arg Glu Gly Tyr Leu
            580                 585                 590

Ile Ser Glu Glu Glu Phe Tyr Pro Tyr Gly Gly Thr Ala Val Leu Thr
        595                 600                 605

Ala Arg Ser Glu Val Glu Ala Asp Tyr Lys Thr Ile Arg Tyr Ser Gly
    610                 615                 620

Lys Glu Arg Asp Ala Thr Gly Leu Asp Tyr Tyr Gly Tyr Arg Tyr Tyr
625                 630                 635                 640

Gln Pro Trp Ala Gly Arg Trp Leu Ser Thr Asp Pro Ala Gly Thr Val
```

-continued

```
                    645                 650                 655
Asp Gly Leu Asn Leu Phe Arg Met Val Arg Asn Asn Pro Val Thr Leu
                660                 665                 670
Phe Asp Ser Asn Gly Arg Ile Ser Thr Gly Gln Glu Ala Arg Arg Leu
                675                 680                 685
Val Gly Glu Ala Phe Val His Pro Leu His Met Pro Val Phe Glu Arg
                690                 695                 700
Ile Ser Val Glu Arg Lys Ile Ser Met Ser Val Arg Glu Ala Gly Ile
705                 710                 715                 720
Tyr Thr Ile Ser Ala Leu Gly Glu Gly Ala Ala Ala Lys Gly His Asn
                725                 730                 735
Ile Leu Glu Lys Thr Ile Lys Pro Gly Ser Leu Lys Ala Ile Tyr Gly
                740                 745                 750
Asp Lys Ala Glu Ser Ile Leu Gly Leu Ala Lys Arg Ser Gly Leu Val
                755                 760                 765
Gly Arg Val Gly Gln Trp Asp Ala Ser Gly Val Arg Gly Ile Tyr Ala
                770                 775                 780
His Asn Arg Pro Gly Gly Glu Asp Leu Val Tyr Pro Val Ser Leu Gln
785                 790                 795                 800
Asn Thr Ser Ala Asn Glu Ile Val Asn Ala Trp Ile Lys Phe Lys Ile
                805                 810                 815
Ile Thr Pro Tyr Thr Gly Asp Tyr Asp Met His Asp Ile Ile Lys Phe
                820                 825                 830
Ser Asp Gly Lys Gly His Val Pro Thr Ala Glu Ser Ser Glu Glu Arg
                835                 840                 845
Gly Val Lys Asp Leu Ile Asn Lys Gly Val Ala Glu Val Asp Pro Ser
850                 855                 860
Arg Pro Phe Glu Tyr Thr Ala Met Asn Val Ile Arg His Gly Pro Gln
865                 870                 875                 880
Val Asn Phe Val Pro Tyr Met Trp Glu His Glu His Asp Lys Val Val
                885                 890                 895
Asn Asp Asn Gly Tyr Leu Gly Val Val Ala Ser Pro Gly Pro Phe Pro
                900                 905                 910
Val Ala Met Val His Gln Gly Glu Trp Thr Val Phe Asp Asn Ser Glu
                915                 920                 925
Glu Leu Phe Asn Phe Tyr Lys Ser Thr Asn Thr Pro Leu Pro Glu His
                930                 935                 940
Trp Ser Gln Asp Phe Met Asp Arg Gly Lys Gly Ile Val Ala Thr Pro
945                 950                 955                 960
Arg His Ala Glu Leu Leu Asp Lys Arg Arg Val Met Tyr
                965                 970
```